US012062457B2

(12) United States Patent
Wohlstadter et al.

(10) Patent No.: US 12,062,457 B2
(45) Date of Patent: Aug. 13, 2024

(54) GLOBAL BIO-SURVEILLANCE AND RESPONSE SYSTEM

(71) Applicant: Meso Scale Technologies, LLC., Rockville, MD (US)

(72) Inventors: Jacob N. Wohlstadter, Potomac, MD (US); Michael Vock, Loveland, OH (US); Charles M. Clinton, Burtonsville, MD (US); George Sigal, Rockville, MD (US)

(73) Assignee: MESO SCALE TECHNOLOGIES, LLC, Rockville, MD (US)

( * ) Notice: Subject to any disclaimer, the term of this patent is extended or adjusted under 35 U.S.C. 154(b) by 196 days.

(21) Appl. No.: 17/359,479

(22) Filed: Jun. 25, 2021

(65) Prior Publication Data

US 2021/0407692 A1    Dec. 30, 2021

Related U.S. Application Data

(60) Provisional application No. 63/044,815, filed on Jun. 26, 2020.

(51) Int. Cl.
| | |
|---|---|
| *G16H 50/80* | (2018.01) |
| *G01N 21/76* | (2006.01) |
| *G06Q 50/40* | (2024.01) |
| *G16H 10/40* | (2018.01) |
| *G16H 40/20* | (2018.01) |

(Continued)

(52) U.S. Cl.
CPC ............. *G16H 50/80* (2018.01); *G01N 21/76* (2013.01); *G06Q 50/40* (2024.01); *G16H 10/40* (2018.01); *G16H 40/20* (2018.01); *G16H 40/67* (2018.01); *G16H 50/20* (2018.01)

(58) Field of Classification Search
CPC ........ G16H 50/80; G16H 10/40; G16H 40/20; G16H 40/67; G16H 50/20; G01N 21/76; G01N 21/66; G06Q 50/30; G06Q 10/0631; G06Q 10/087; Y02A 90/10; A61B 5/01;

(Continued)

(56) References Cited

U.S. PATENT DOCUMENTS

| | | | |
|---|---|---|---|
| 2011/0136262 A1 | 6/2011 | Ragavan et al. | |
| 2012/0179585 A1* | 7/2012 | Guzzo | H04Q 9/00 705/28 |

(Continued)

OTHER PUBLICATIONS

"Cloud Computing—Wikipedia", "https://en.wikipedia.org/w/index.php?title=Cloud_computing&oldod=816206558", 2017-25-19, retrieved Feb. 11, 2019.

(Continued)

*Primary Examiner* — Joy Chng
(74) *Attorney, Agent, or Firm* — MEDLER FERRO WOODHOUSE & MILLS PLLC

(57) ABSTRACT

Provided herein are systems, methods, and apparatuses for providing a real-time global bio-surveillance and response solution. The systems and apparatuses may include one or more sentinel subsystems and one or more surge subsystems that each include a real-time, cloud-based, distributed, interconnected set of hardware, software, and/or firmware for comprehensive surveillance, complete detection, and immediate response various to biological, chemical, and/or biochemical anomalies, for example, a new or emerging pathogen or other health condition.

26 Claims, 20 Drawing Sheets

(51) Int. Cl.
*G16H 40/67* (2018.01)
*G16H 50/20* (2018.01)

(58) Field of Classification Search
CPC ............... A61B 5/021; A61B 5/14542; G06K 19/06028; G06K 19/06037; G16B 30/00
USPC ........................................................ 705/2–3
See application file for complete search history.

(56) References Cited

U.S. PATENT DOCUMENTS

2017/0161443 A1* 6/2017 Bassham ................ G16H 40/20
2017/0300641 A1* 10/2017 Qerim .................... G16H 40/67
2018/0308585 A1* 10/2018 Holmes .................. G16Z 99/00

OTHER PUBLICATIONS

Partial International Search Report and Written Opinion issued Oct. 6, 2021 in international Appln. No. PCT/US2021/039268.
International Search Report and Written Opinion issued Jan. 20, 2022, in International Appln. No. PCT/US2021/039268.
Younes Nadin et al.: "Challenges in Laboratory Diagnosis of the Novel Coronavirus SARS-COV-2", Viruses, vol. 12, No. 6, May 26, 2020 (May 26, 2020), p. 582, XP055858980, DOI: 10.3390/v12060582 Retrieved from the Internet: URL:https://www.ncbi.nlm.nih.gov/pmc/articles/PMC7354519/pdf/viruses-12-00582.pdf> abstract; p. 2; sections 2, 3.4.3; table 1.

* cited by examiner

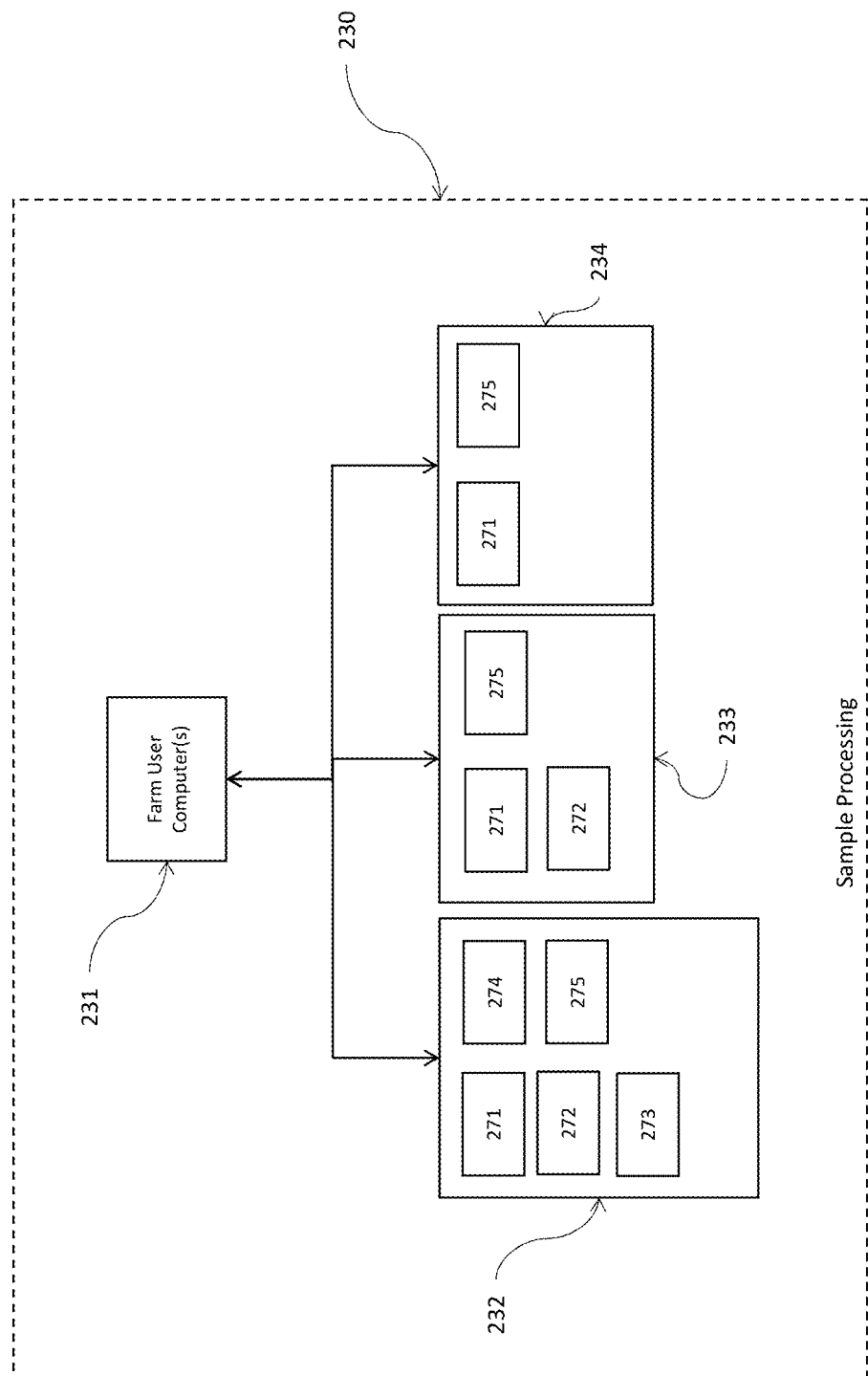

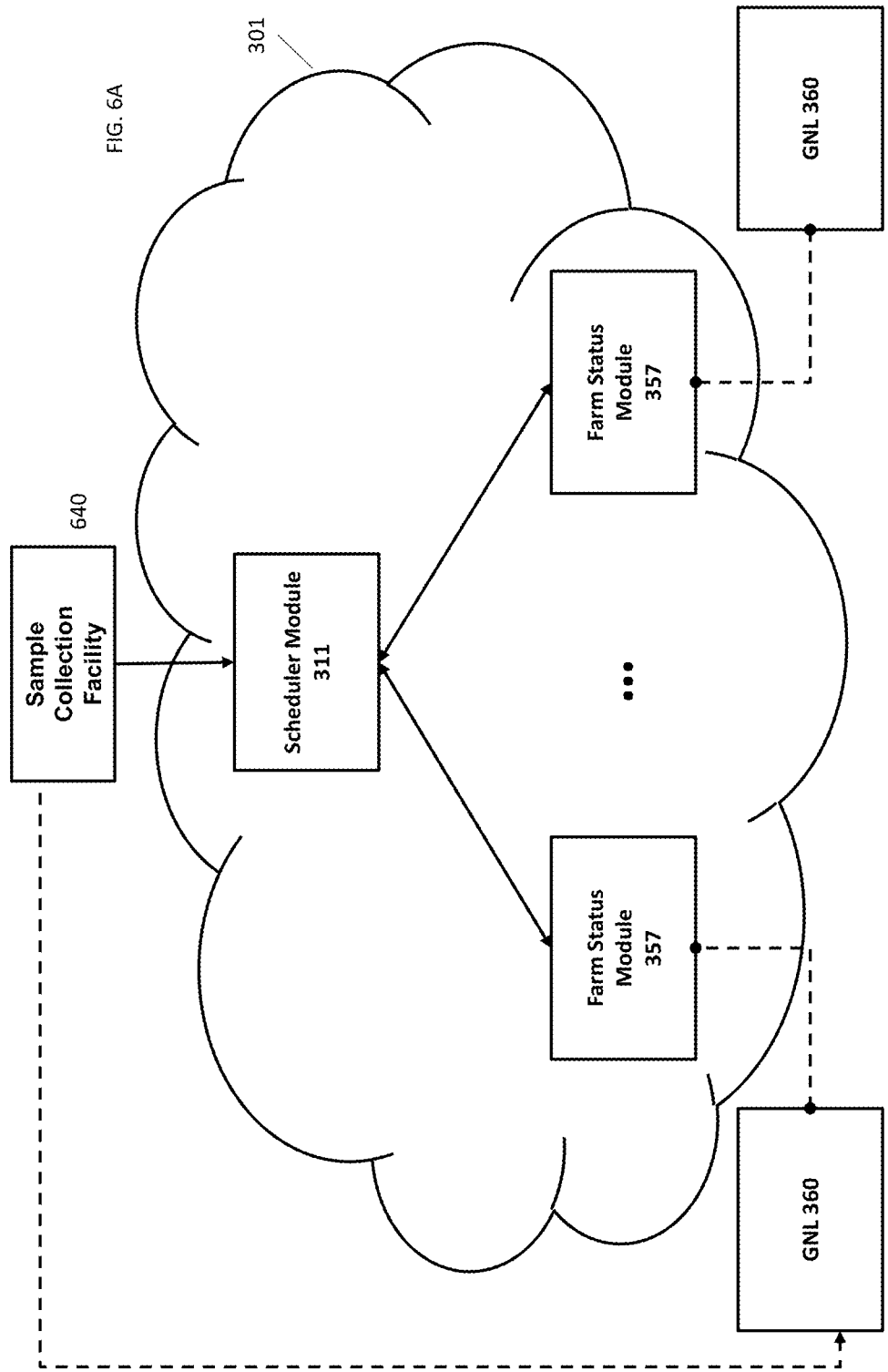

GLOBAL BIO-SURVEILLANCE AND RESPONSE SYSTEM

CROSS-REFERENCE TO RELATED APPLICATIONS

This application claims priority to U.S. provisional application 63/044,815, filed on Jun. 26, 2020, which is hereby incorporated by reference in its entirety.

This application refers to and incorporates by reference in their entirety, the following patent documents: U.S. Application No. PCT/US2014/010016, filed on Jan. 2, 2014; U.S. Application No. PCT/US2014/022948, filed on Mar. 11, 2014; U.S. Application No. PCT/US2014/026010, filed on Mar. 13, 2014; U.S. Application No. PCT/US2015/03092, filed on May 15, 2015; U.S. Application No. PCT/US20/30754, filed on Apr. 30, 2020; U.S. Application No. PCT/US02/20570, filed on Jun. 29, 2002; U.S. Application No. PCT/US03/041241, filed on Dec. 23, 2003; U.S. Application No. PCT/US2006/049049, filed on Dec. 21, 2006; U.S. Application No. PCT/US2010/058913, filed on Dec. 3, 2010; U.S. Application No. PCT/US2014/010182, filed on Jan. 3, 2014; U.S. Application No. PCT/US2016/026242, filed on Apr. 6, 2016; U.S. Application No. PCT/US2016/043755, filed on Jul. 22, 2016; U.S. Application No. PCT/US2017/014360, filed on Jan. 20, 2017; U.S. Application No. PCT/US2019/032567, filed on May 16, 2019; U.S. Application No. 62/954,961, filed on Dec. 30, 2019; U.S. Application No. 63/025,344, filed on May 15, 2020; U.S. Application No. PCT/US2019/042274, filed on Jul. 17, 2019; and U.S. Application No. 62/964,435, filed on Jan. 22, 2020.

TECHNICAL FIELD

The present application relates generally to systems, methods, and apparatuses for providing a real-time global bio-surveillance and response solution.

BACKGROUND

In the face of a biological, chemical, and/or bio-chemical catastrophe, such as a global pandemic, governments, private companies, and private institutions are ill-prepared to quickly detect and mount a rapid and effective response to these events. This is because these entities offer a disparate patchwork of existing public and private clinical diagnostics testing, which is not fully realized or able to respond to a rapidly developing global event or health condition. The current response capabilities of these entities are not able to prevent either the crippling effects these events have on economies, or the resulting dramatic loss of life. Moreover, existing infrastructures are overrun and overburdened, and undertake reactive testing approach; the vast majority of which occurs after the triggering event has occurred.

What is required, thus, are systems, methods, and apparatuses that provide a real-time solution with a centralized infrastructure, that is sufficiently funded, stockpiled and staffed, offering an interconnected web and network of testing devices that routinely test for these catastrophic events, and provide an infrastructure to rapidly ramp up and meet global demand for testing and the development of scientific solutions (assay development, vaccine development, etc.) to combat the events and to protect lives and economies. Other examples exist and the solutions disclosed herein are not limited to the problems discussed above.

BRIEF SUMMARY

Applicants have created systems, methods, and apparatuses (including computer-readable media) for providing a real-time global bio-surveillance and response solution. The systems and apparatuses may include one or more sentinel subsystems and one or more surge subsystems that each include a real-time, cloud-based, distributed, interconnected set of hardware, software, and/or firmware for comprehensive surveillance, complete detection, and immediate response various to biological, chemical, and/or bio-chemical anomalies, for example, a new or emerging pathogen. The methods may include providing one or more tests to assess a health condition, including to detect pathogens, such as infectious agents and toxins, of both natural origin and biowarfare or bioterrorism agents, and host biomarkers of disease, including biomarkers associated with infection and toxemia, and biomarkers associated with radiation exposure (biodosimetry), and providing real-time results across a global network of infrastructure that is adapted to provide the testing for and responses to health conditions. In a non-limiting example, the methods may include providing one or more tests to detect a known, unknown, or emerging pathogen, and in response to detecting an unknown or emerging pathogen, providing real-time results across a global network of infrastructure that is adapted to provide the testing for and responses to the unknown or emerging pathogen. In further embodiments, the methods may include a method of tracking a health condition in a population that includes the steps of providing one or more tests to detect a set of one or more markers relating to said health condition, and providing real-time results across a global network of infrastructure (e.g., a plurality of sentinel surveillance testing systems and a plurality of surge surveillance testing systems) that is adapted to identify and respond to a known, unknown, or emerging risk to health.

A computer readable storage medium storing a program of instructions executable by a machine to perform one or more methods described herein also may be provided.

In an embodiment, a global bio-surveillance and response system is provided. The global bio-surveillance and response system includes a first subsystem configured to perform monitoring of one or more health conditions; a second subsystem configured to perform one or more scientific functions in response to the first subsystem's detection of the one or more health conditions; and a networking platform, wherein the networking platform is configured to communicate information in real-time to and/or from one or both of the first and second subsystems.

In a further embodiment, a method for responding to a known, unknown, or emerging health condition is provided. The method includes providing targeted testing to detect one or more health conditions among a population to obtain targeted results; transmitting the targeted results to a system monitoring subsystem, wherein the targeted results are transmitted in real-time across a distributed network of infrastructure; responsive to the targeted results, performing one or more of the following steps: increasing the rate of testing among the population to detect the presence of the one or more health conditions, and increasing the number of individuals tested among the population to detect the presence of the one or more health conditions.

In a further embodiment, a method of allocating resources within a global bio-surveillance and response system is provided. The method includes receiving information relating to one more available resources of a network of laboratories configured to monitor one or more health conditions in real-time; analyzing the information based at least in part on one or more selection criteria; and routing one or more of equipment, test samples, instruments, supplies, and/or personnel to a selected laboratory among the network of laboratories responsive to analyzing the received information and based on the one or more selection criteria.

In a further embodiment, a method for responding to a health-related triggering event is provided. The method includes providing targeted testing to detect the presence of one or more health conditions among a population exhibiting a defined set of symptoms to obtain targeted testing results; transmitting the targeted testing results in real-time to a distributed infrastructure network; providing one or more scientific detection tools configured to analyze the one or more health conditions responsive to the targeted testing results; and developing a scientific diagnostic tool responsive to analysis of the targeted testing results from the one or more scientific diagnostic tools; and distributing one or more of test equipment, scientific detection tools, and scientific diagnostics tools to at least one location within the network of infrastructure responsive to providing the one or more scientific detection tools or developing the scientific diagnostic tool.

In a further embodiment, a device for managing a global bio-surveillance and response system, comprising at least one processor configured to execute software instructions is provided. The software instructions are configured to provide an information subsystem configured to receive information from at least one subsystem and to facilitate the analysis of the information for providing a response to a health condition in a population; and a command subsystem configured to provide commands to the at least one subsystem for carrying out the response, wherein the information subsystem and the command subsystem are configured to receive real-time communications from the at least one subsystem through a web-based platform.

In a further embodiment, a global bio-surveillance and response system is provided. The system includes a subsystem configured to perform monitoring of one or more health conditions, wherein the subsystem includes a plurality of portable testing devices distributed among a geographical area; a system monitoring subsystem configured to: receive inputs from the subsystem and send outputs to the subsystem in real-time, facilitate analysis of the inputs, and determine the outputs, responsive to the inputs; and a networking platform configured to communicate with a plurality of the portable testing devices in real time.

In a further embodiment, a global bio-surveillance and response system is provided. The system includes a first subsystem configured to perform one or more scientific functions in response to a detection by a second subsystem of one or more health conditions, wherein the subsystem includes a plurality of scientific diagnostic equipment; a system monitoring subsystem configured to: receive inputs from the first subsystem and the second subsystem and sending outputs to the first subsystem and the second subsystem in real-time, and facilitate analysis of the inputs to determine the outputs to send to the first subsystem; and a networking platform, wherein the networking platform is configured to communicate with the scientific diagnostic equipment in real time.

In a further embodiment, a method of minimizing the spread of a health condition in a population is provided. The method includes providing targeted testing to detect one or more health conditions among a population within a geographical area, wherein the health conditions are at least one of biological, chemical, and biochemical; confining the population within that geographical area for a finite period of time responsive to the detection of the one or more health conditions within that geographical area; performing additional testing of individuals within the geographical area within the finite period of time; and allocating additional resources to the geographical area for which the one or more health conditions were detected.

In a further embodiment, a global laboratory network is provided. The network includes a plurality of networked laboratories having a geographical distribution and configured to provide continuous monitoring of populations, targeted testing, and/or scientific functions, wherein each one of the plurality of networked laboratory is configured to communicate with one or more other ones of the plurality of networked laboratories; and a system monitoring subsystem configured to: receive inputs from the plurality of networked laboratories, and send outputs to one or more of the plurality of networked laboratories in real-time, allocate resources among the plurality of networked laboratories based at least in part on the inputs from the or more laboratories.

In a further embodiment, a method of pandemic preparedness is provided. The method includes providing one or more tests to detect a known, unknown, or emerging pathogen; and providing, responsive to detection of an unknown or emerging pathogen, real-time results across a global network of infrastructure, the global network of infrastructure being configured to provide testing for the unknown or emerging pathogen and respond to the unknown or emerging pathogen.

In a further embodiment, a method of tracking a health condition in a population is provided. The method includes providing one or more tests to detect a set of one or more markers relating to the health condition; obtaining results from the one or more tests; and providing the results in real-time across a global network of infrastructure configured to identify and respond to a known, unknown, or emerging risk to health.

Further features as well as the structure and operation of various embodiments are described in detail below with reference to the accompanying drawings.

BRIEF DESCRIPTION OF THE DRAWINGS

The following figures form part of the present specification and are included to further demonstrate certain aspects of the present invention. The invention may be better understood by reference to one or more of these figures in combination with the detailed description of specific embodiments presented herein.

FIG. 2B illustrates portions of the global bio-surveillance and response system in accordance with embodiments hereof.

FIG. 6A illustrates operation of a scheduler module according to embodiments hereof.

DETAILED DESCRIPTION

Figure 1:
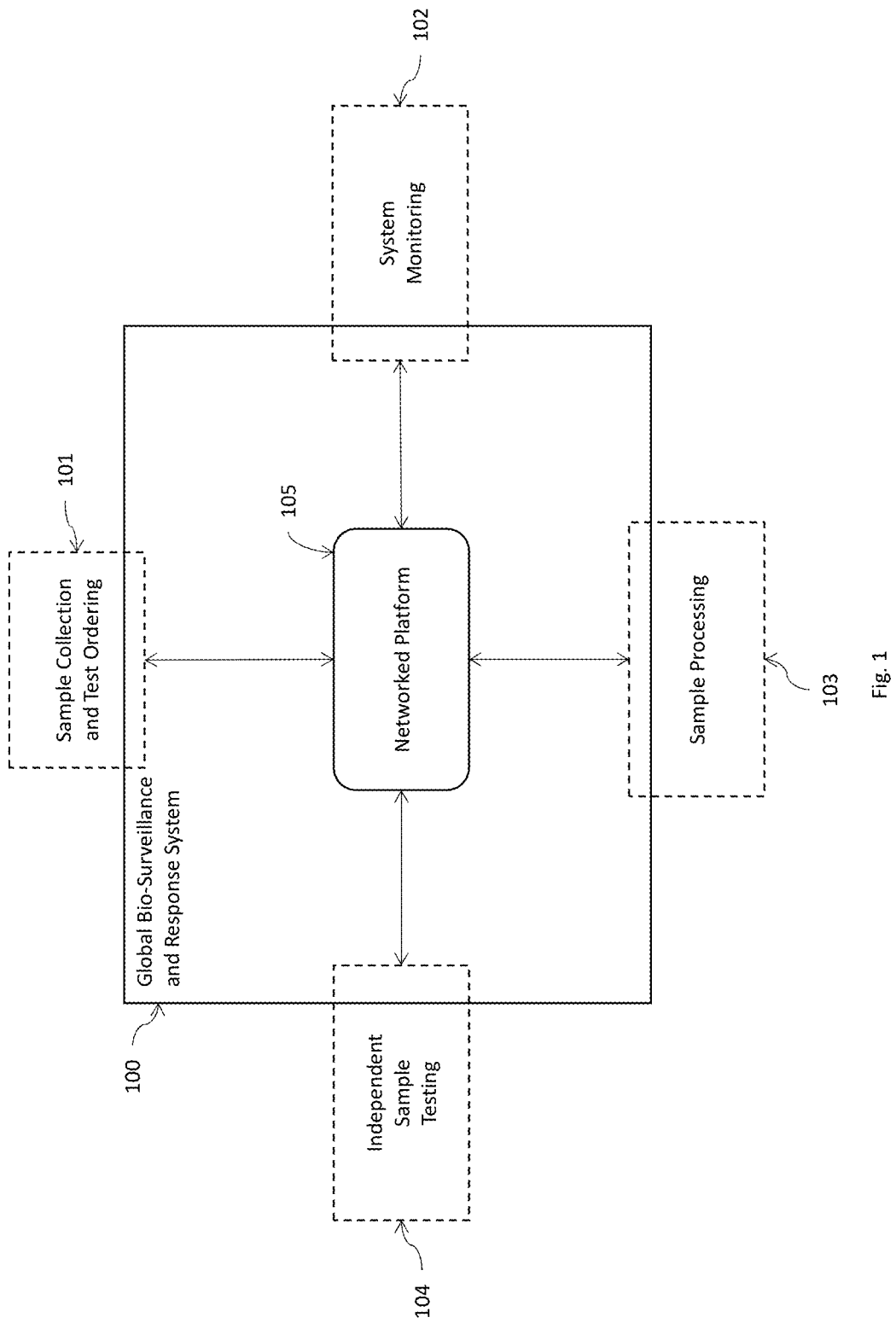
FIG. 1 depicts an embodiment of a global bio-surveillance and response system in accordance with the certain aspects of the disclosure.

Embodiments described herein provide technical solutions to various technical problems via improvements to existing technologies and the creation of wholly new technologies. Among the technical problems addressed by embodiments discussed herein include inefficiencies existing public and private clinical diagnostics testing, which is not fully realized or adequately developed to handle a rapidly developing global event.

Applicants have created systems, methods, and apparatuses for providing a real-time global bio-surveillance and response solution. The systems may include one or more sentinel subsystems (also referred to throughout as "surveillance" or "distributed" subsystems), one or more surge subsystems, one or more networking platforms, and one or more mission control systems. In embodiments, the sentinel subsystem may include a real-time, cloud-based, distributed, interconnected set of hardware, software, and/or firmware, including, for example, instruments, such as cartridge readers, Point of Care (POC) devices, etc., that may be widely and ubiquitously distributed globally to monitor, detect, and report, various biological, chemical, and/or bio-chemical anomalies, such as, for the example, a new, emerging, pathogen. In a non-limiting, illustrative embodiment, the sentinel subsystem may include a large number of dedicated cartridge readers (for example, millions of instruments) that are deployed globally to provide detection and distinction between and among known and unknown and/or new, and/or emerging pathogens. Continuing with this example, the components of the sentinel system, such as test sample readers, may be strategically deployed to cast a wide and fully comprehensive surveillance net to enable early detection, contract tracing, and/or quarantine protocols to stop the spread of a newly detected pathogens. These readers may be strategically deployed to airports and/or transportation hubs, corporations, nursing homes, ambulances, schools and universities, emergency rooms, general practitioner offices, hospitals, pharmacies, urgent care facilities, pediatrician and other doctors' offices, concerts, sporting events, etc. Because the sentinel subsystem may operate in real-time (such as, for example, through cloud-based software), the results may be collected, aggregated, and analyzed instantaneously and on demand, providing an early detection system that is adapted to communicate to and work in conjunction with the surge subsystem. Accordingly, the sentinel subsystem is configured, through the use of the various devices described herein, to provide global, regional, and/or national monitoring of a health condition.

As discussed herein, "a health condition" in embodiments may refer to a condition affecting the health of a portion of a population (local, regional, or global), such as, as for example, an infectious disease, a pathogen, a biochemical thread, a chemical toxin, a biological threat, radiation exposure, TBI incidence, and any other health condition that may affect all or a portion of a population. In embodiments, a health condition may manifest itself through one or more physical symptoms of individuals, such as fever, respiratory complications (e.g., coughing, shortness of breath, difficulty breathing etc.), nausea, headache, chills, muscle aches, body aches, etc.

As used herein, "real-time" and "near real-time" in embodiments may refer to computational and communication operations of networked systems that perform computations and send and receive data as quickly as possible within system limitations. For example, "real-time" communication or sharing of data may refer to the sending of data as it is received and/or obtained, without an intervening long-term storage step. "Real-time" updating may refer to a system that updates data report as the data is received, rather than on a fixed schedule or in batches. It is understood that, due to limitations of computer and networking systems, "real-time" communications are not instantaneous.

The surge subsystem may include a include a real-time, distributed, interconnected set of hardware, software, and/or firmware, including, for example, high and/or ultrahigh throughput testing, sequencing, and/or scientific development instrumentation and equipment—for example, assay development, vaccine development, next generation sequencing (e.g., massively parallel sequencing) capabilities, etc. The instrumentation and/or hardware may include fully integrated, one-stop-shop instruments such as the Parsec™ R 5000 instrument (P5)—for example, as disclosed in U.S. Application No. PCT/US2016/043755, filed on Jul. 22, 2016; U.S. Application No. PCT/US2017/014360, filed on Jan. 20, 2017; and U.S. Application No. 63/025,344, filed on May 15, 2020, each of which is incorporated herein by reference—and/or an interconnected network of instruments and equipment for carrying our scientific testing, experimentation, and assay/vaccine development (e.g., assay readers, washers, plate shakers, incubators, etc.). In other examples, high throughput instruments, such as, for example those disclosed in U.S. Application No. PCT/US2016/026242, filed on Apr. 6, 2016; and U.S. Application No. PCT/US2019/032567, filed on May 16, 2019 each of which is incorporated herein by reference. Other examples of instruments that may be used in the surge subsystem include, for example U.S. Application No. PCT/US02/20570, filed on Jun. 29, 2002; U.S. Application No. PCT/US2006/049049, filed on Dec. 21, 2006; U.S. Application No. PCT/US2014/010182, filed on Jan. 3, 2014; and U.S. Application No. 62/954,961, filed on Dec. 30, 2019 each of which is incorporated herein by reference. In embodiments, one or more of the instruments may be either provided as one or more individual units or devices, or provided in one or more globally networked laboratories (GNLs), also referred to as "farms" in certain embodiments throughout. In non-limiting exemplary embodiments, a farm or GNL may include a group of instruments and/or systems (e.g., 5, 10, 11, etc.) that may be provided at a centralized location (or split between or among multiple centralized locations). In embodiments, these instruments and/or systems may be fully automated, partially automated, and/or manually operated devices.

Using the same example above regarding the detection of a new pathogen, the equipment and instrumentation comprising the surge subsystems may include a real-time, cloud-based network of devices capable of collecting, receiving, and/or analyzing results received in real-time from the one or more sentinel subsystems, and providing a response by producing millions (or hundreds of millions) test per week, screening for antigens, antibodies, nucleic acid tests to address the newly detected pathogen. Accordingly, the surge subsystem is configured, through the use of the various devices described herein, to provide a response to a health condition detected through use of the sentinel subsystem. The surge subsystem is configured to preform one or more scientific functions, including, for example high-throughput sample testing, rapid sequencing of the DNA/RNA of unknown pathogens, probe/primer synthesis for rapid stand-up of plate-based assays (e.g., 96-well ECL plates) and Polymerase Chain reaction (PCR) assays, protein synthesis capabilities to rapidly generate reagents to support immunoassays, rapid assay development; and other laboratory functions appropriate for response to a health condition. In embodiments, the sentinel subsystem and the surge subsystem may include at least some of the same components and devices, operating under different conditions.

The information collected, produced, and/or derived from the one or more sentinel and/or surge subsystems may be fed through and analyzed with the aid of a mission control subsystem. The mission control subsystem is a collection of software (e.g., cloud-based) and hardware configured to gather and present a unified picture of all the activity and results within the sentinel and surge subsystems and among all the deployed instruments in the sentinel network and the surge network, providing a single, unified, easy to use and understand, dashboard to advise operators as to the ongoing operations of these subsystems. The mission control subsystem is further configured to provide and/or facilitate an automated and/or human guided response, through the capabilities of the surge subsystem, to the data and information collected via the sentinel subsystem. In embodiments, the mission control subsystem can be further utilized to track samples (e.g., from point of collection to the point of testing) via the aid of one or more barcodes (e.g., 2D, QR codes), provide changes and modifications to testing protocols, and facilitate efficient load balancing and/or allocation of various resources including, but not limited to, sample testing capacities, instruments, consumables, equipment, supplies, and/or human resources, such as lab operators, and other personnel.

By providing a real-time global bio-surveillance and response solution, the systems, methods, and apparatuses disclosed herein may be deployed across a broad range of applications, in order to immediately detect and quickly respond to catastrophic events. A few non-limiting examples of the applications for which the systems, methods, and apparatuses described herein may be applied to include: facilitating pandemic, epidemic, and/or endemic responses; as an epidemiological infrastructure tool, for biodosimetry testing and/or radiological events, such as a nuclear plant meltdown; and/or for bio/chemical-defense-related events (e.g., localized or global deployment of chemical and/or biological weapons).

Throughout the following disclosure, references are made to various computing devices, such as computers, servers, tablets, mobile devices, etc. Although a specific example (e.g., a server) may be provided to describe a computing device, it is understood that the role of such a computing device may be fulfilled by a different computing device having similar functionality. Accordingly, a computing devices described herein may alternately be configured as a server (e.g., having one or more server blades, processors, etc.), a personal computer (e.g., a desktop computer, a laptop computer, etc.), a mobile device, such as, for example, a smartphone, a tablet computing device, and/or other device that can be programmed. The functionality of computing devices described herein may be implemented via one or more processors associated with the computing devices. Additionally, various other hardware and instrumentation (e.g., assay devices, cartridge readers, and other bioistrumentation devices) include one or more processors and associated hardware for carrying out software functionality as described herein. In other embodiments, the functionality of the processor may be performed by hardware (e.g., through the use of an application specific integrated circuit ("ASIC"), a programmable gate array ("PGA"), a field programmable gate array ("FPGA"), etc.), or any combination of hardware and software. In still further embodiments, the functionality of processors described herein may be carried out via cloud computing resources. Storage devices described herein may include any type of non-transitory computer readable storage medium (or media) and/or non-transitory computer readable storage device. Such computer readable storage media or devices may store computer readable program instructions for causing a processor to carry out one or more methodologies described here. Examples of the computer readable storage medium or device may include, but is not limited to an electronic storage device, a magnetic storage device, an optical storage device, an electromagnetic storage device, a semiconductor storage device, or any suitable combination thereof, for example, such as a computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, but not limited to only those examples. When programmed with the software functionality described herein, the various computing devices may function as special purpose computers.

FIG. 1A illustrates an embodiment of a global bio-surveillance and response system in accordance with the certain aspects of the disclosure. In embodiments, the global bio-surveillance and response system 100 may include a cloud-based system, providing seamless integration of other systems, computers, and software for a global bio-surveillance and response system. Global bio-surveillance and response system 100 may be used in both standard testing (e.g., by a sentinel subsystem) and surge testing (e.g., during a pandemic) modalities. The global bio-surveillance and response system 100 may include various systems, hardware, computers, and software including a sample collection and test ordering subsystem 101, a system monitoring subsystem 102, a sample processing subsystem 103, and an independent sample test subsystem 104. One or more of these subsystems may be connected to one or more of the others through the networked platform 105 (e.g., a cloud platform).

In embodiments, the one or more sentinel (or surveillance) subsystems described herein may include one or more of the independent sample testing subsystem 104, the sample collection and test ordering subsystem 101, and the networked platform 105. The sentinel subsystem may be configured, as described herein, to perform and/or facilitate monitoring of one or more health conditions. In a non-limiting, exemplary embodiment, an independent sample testing subsystem 104 and a sample collection and test ordering subsystem 101 of a sentinel subsystem may include one or more of: distributed sentinel devices (e.g., FIG. 2A, 241); clinical lab operations (e.g., FIG. 2A, 242); clinical data integration computers (e.g., FIG. 2A, 243); test ordering user computers (e.g., FIG. 2A, 209); and one or more of various testing locations (e.g., FIG. 2A, 202-208). In further embodiments, the one or more sentinel subsystems may include one or more of the subsystems and networked platform 105 depicted in the example illustrated by FIG. 1A. In embodiments, the one or more sentinel subsystems may include one or more distributed sentinel devices, as described herein.

In embodiments, the one or more surge subsystems described herein may include one or more of the sample processing subsystem 103, the sample collection and test ordering subsystem 101, and networked platform 105. The surge subsystem, as described herein, may be configured to perform and/or facilitate the performance of one or more scientific and/or research functions in response to the detection of health conditions by the sentinel subsystem. In a non-limiting, exemplary embodiment, the one or more of the sample processing subsystem 103 of a surge subsystem may include one or more of: farm user computers (e.g., FIG. 2A, 231); Tier-1 farm lab operations (e.g., FIG. 2A, 232); Tier-2 farm lab operations (e.g., FIG. 2A, 233); and Tier-3 farm lab operations (e.g., FIG. 2A, 234), etc. In further embodiments, the one or more surge subsystems may include one or more of the subsystems and networked platform 105 depicted in the example illustrated by FIG. 1A. In embodiments, the one or more surge subsystems may include one or more surge surveillance testing systems.

In embodiments, the mission control subsystem described herein may include one or more system monitoring subsystems 102. The system monitoring subsystems 102 may include one or more of mission control user computers 221, monitoring data integration computers 222, and external monitoring systems 223. In further embodiments, the mission control subsystem may further include the networked platform 105.

In embodiments, the operating system on each computer in whole or part in the global bio-surveillance and response system 100 may be Windows, UNIX, Linux, MacOS, iOS, Android, and/or any other commercial, open-source, and/or special-purpose operating system.

Sample collection and testing ordering subsystem 101, illustrated in greater detail below, e.g., 201 in FIG. 2A, may include a collection of one or more servers, desktop computers, laptop computers, tablets, mobile devices, and/or any other computing device of which one or more of those computers may be used in or in connection with global bio-surveillance and response system 100 to perform one or more steps, including placing orders on samples to be tested, sending samples to the appropriate testing location, and reviewing results of the testing. One or more entities may perform one of functions of the sample collection and testing ordering subsystem 101 using the bio-surveillance system 100. The sample collection and testing ordering subsystem 101 is configured to coordinate the collection of samples, ordering of tests, and division of load across the independent sample testing subsystems 104 that make up the sentinel subsystem.

Independent sample testing subsystem 104 illustrated in greater detail below, e.g., 240 in FIG. 2A, may include a collection of one or more servers, desktop computers, laptop computers, tablet, and/or mobile devices of which one or more of those computers, as well as associated bio-instrumentation, which may be used in the global bio-surveillance and response system 100 for various functions, including for reporting sample testing results performed (e.g., in real-time and/or in a time-delayed fashion). One or more entities, e.g., clinicians, technicians, lab operators, etc., may assist in carrying out the functions of independent sample testing subsystem 104, for example, by reporting those results using on or more subsystems or functions of the bio-surveillance system 100. The independent sample testing subsystem 104 is configured to facilitate sample testing, e.g., for pathogens, via bioinstrumentation and one or more entities, such as laboratory or medical personnel.

The sample processing subsystem 103 illustrated in greater detail below, e.g., 230 in FIGS. 2A and 2B, may include a collection of one or more servers, desktop computers, laptop computers, tablet, and/or mobile devices of which one or more of those computers may be used in on or on behalf of bio-surveillance system 100, as well as the collection of bio-instrumentation that may be used to perform testing requested by entities, e.g., clinicians, laboratory technicians, medical and hospital staff, etc., for example, to be performed by the sample collection and testing ordering subsystem 101. One or more entities may perform the functions of the sample processing subsystem 103 using the global bio-surveillance and response system 100 and its relevant subsystems and features.

The system monitoring subsystem 102, illustrated in greater detail below, e.g., 220 in FIG. 2A, may include a collection of one or more servers, desktop computers, laptop computers, tablet, and/or mobile devices of which one or more of those computers may be used in global bio-surveillance and response system 100 for supporting one or more of the monitoring, control, oversight, and review of the operation of and data produced by the bio-surveillance system 100. One or more entities, e.g., operators, clinicians, technicians, medical directors and staff, etc., either internal or external to bio-surveillance system 100, may carry functions within and/or on behalf of bio-surveillance system at 100. For example, those entities, may perform system monitoring (e.g., carry out roles performed by the system monitoring subsystem 102). The system monitoring subsystem 102 is configured to monitor the information and data collected via the sentinel subsystem, provide that information to one or more entities, and facilitate or cause the operation of various functions within the sentinel and surge subsystems, as discussed herein.

Networked platform 105 may be leveraged to bi-directionally (or uni-directionally) connect through computers, networking, and software, one or more all computers and/or other hardware comprising global bio-surveillance and response system 100 in a common computing, software services, and data architecture. In embodiments, data and information may be collected and shared by any computer with associated software of global bio-surveillance and response system 100 wherever a particular computer with associated software in global bio-surveillance and response system 100 may be in the world in a secure way. In embodiments, the networked platform 105 may be hosted by a global public-cloud provider, providing a shared computing environment, for example, Amazon Web Services, Google Cloud, Microsoft Azure, or others. In additional embodiments, the networked platform 105 may be self-hosted by one or more providers of the bio-surveillance system 100, hosted by a private-cloud provider that includes a dedicated computing environment, e.g., Oracle Cloud, IBM Cloud, Rackspace, or others. In further embodiments, networked platform 105 may be hosted on some combination of public-cloud provider, private-cloud provider, and/or self-hosted by one or more providers of bio-surveillance system 100. The networked platform 105 is configured to provide and/or facilitate connectivity between the various subsystems of the global bio-surveillance and response system 100. For example, the networked platform 105 is configured to permit the direction and coordination of the operation of the various subsystems from locations remote from the devices and components that make up the various subsystems.

In embodiments, all communication to/from the networked platform 105 may be accomplished over a secure communication protocol such as https using TL 1.2 or higher to encrypt all communication between sender and receiver, but other secure or unsecure solutions may be implemented as well, such as an unsecure communication protocol (e.g., http) may be used as well. Hardware and other systems, computing devices, etc. may be connected through connected technologies, such as Ethernet for local area network (LAN), metropolitan area network (MAN), and/or wide area network (WAN) configurations, and/or unconnected technologies, such as Wi-Fi, Bluetooth, and/or other like technologies for a distributed LAN. Additionally, in embodiments, the global bio-surveillance and response system 100 may be deployed across a single computer such that all operations of global bio-surveillance and response system 100 may occur on that computer with the only external communication occurring between computers and associated software running outside of global bio-surveillance and response system 100 and global bio-surveillance and response system 100 itself.

As described herein, the global bio-surveillance and response system 100 provides an improvement to existing technologies for facilitating massive cooperation and coordination between health condition response facilities. Current technologies for addressing this technical problem do not address the need to effectively coordinate response actions in the face of an emerging health condition across a large network of facilities. The global bio-surveillance and response system 100 provided herein provides the capability to coordinate, at one or more mission control centers, a health condition response across an entire network, including point of care facilities, sample processing/testing facilities, sample collection facilities, pathogen study facilities, manufacturing facilities, supply chains, inventory warehouses, etc. This type of coordination permits a rapid and fully supplied response to an emerging health condition occurring anywhere by identifying and utilizing all available resources as efficiently as possible.

Figure 2A:
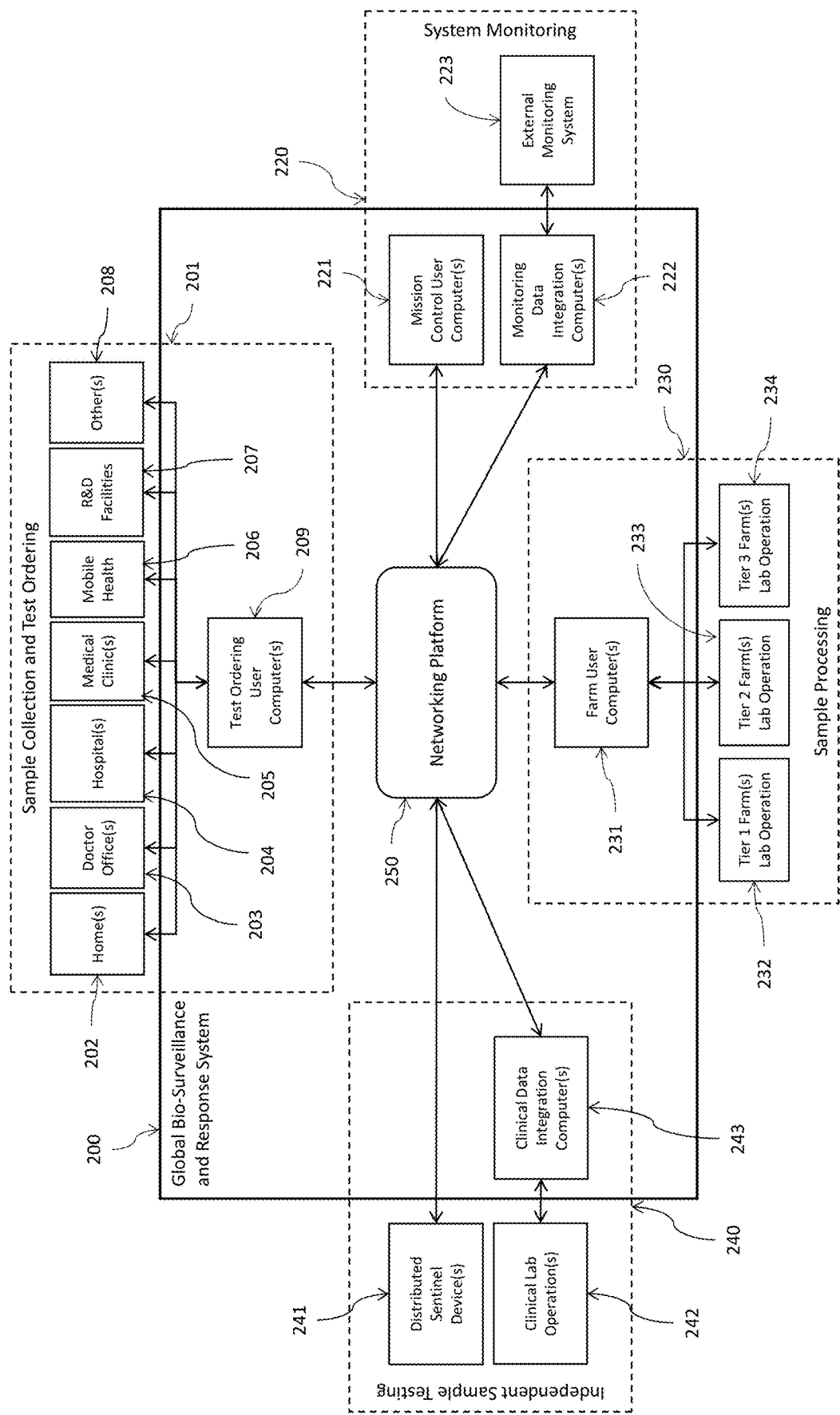
FIG. 2A depicts the system architecture of an embodiment of a global bio-surveillance and response system in accordance with the certain aspects of the disclosure.

FIG. 2A depicts the system architecture of an embodiment of a global bio-surveillance and response system in accordance with the certain aspects of the disclosure. In embodiments, the global bio-surveillance and response system 200 may include a cloud-based system, providing seamless integration of other systems, computers, and bio-instruments that support an integrated and optimized method of executing and reporting sample testing in either a normal or surge testing. The global bio-surveillance and response system 200 may include various systems, hardware, computers, and software that variously make up a sentinel subsystem, a surge subsystem, and a mission control subsystem. For example, the sentinel subsystem may include a sample collection and test ordering subsystem 201, an independent sample testing subsystem 240, and the networking platform 250. The surge subsystem may include the sample collection and test ordering subsystem 201, a sample processing subsystem 230, and the networking platform 250. The mission control subsystem may include the system monitoring subsystem 220 and the networking platform 250. As discussed above, some components, devices, and facilities may be part more than one of the sentinel subsystem, the surge subsystem, and the mission control subsystem.

The sample collection and test ordering subsystem 201, may include one or more test ordering user computers 209 in connection with various collection locations; for example, homes 202, doctor's offices 203, hospitals 204, medical clinics 205, mobile health facilities 206, research and development facilities 207, other testing facilities 208. The sample collection and test ordering subsystem 201 may include a collection of one or more servers, desktop computers, laptop computers, tablets, and/or mobile devices, that may be used in or in connection with the global bio-surveillance and response system 200. In embodiments, one or more test samples and/or test orders may be prepared and sent to the global bio-surveillance and response system 200.

Sample collection and test ordering may occur, for example, at one or more of the identified sample collection locations with one or more of each type of sample collection location providing samples and/or test orders. Although illustrated as separate from each testing location, the testing computers 209 may be incorporated within and/or accessible by any of the testing locations described herein. For example, those locations may include one or more of: an in-home preparation location 202 (e.g., where the sample is prepared by the person being tested (e.g., self-test) or someone helping the person being tested); an in-doctor office location 203 (e.g., preparation is performed by an approved representative of the doctor's office (e.g., the individual's primary care physician, a nurse, other medical professional or paraprofessional, etc.) collecting sample from the person being tested and initiating the test order); a hospital location 204 (e.g., preparation by an approved representative of the hospital collecting sample from the person being tested and initiating the test order); a medical clinic location 205 (e.g., where preparation is performed by an approved representative of the medical clinic collecting sample from the person being tested and initiating the test order—for example, a medical clinical may include one or more of an urgent care facility, specialized testing facility, pharmacy affiliated clinic, and/or any other medical clinic allowed to collect samples and provide a test order through the global bio-surveillance and response system 200); a mobile health location 206 (e.g., preparation by an approved representative of the mobile health entity collecting sample from the person being tested and initiating the test order—for example, a mobile health location may include an ambulance, pop-up testing service supporting efficient public sample collection, and/or any other mobile health entity allowed to collect sample and provide a test order on the global bio-surveillance and response system 200); a research and development facility/location 207 (e.g., preparation by an approved representative of the R&D facility 207 collecting one or more samples to be tested and initiating the test order—for example, the R&D facility/location 207 may include an biopharmaceutical company, biotech company, contract research organization, academic institution, government agency and/or department, public health organization, private health organization, personalized medicine company, translational medicine company, and/or any other R&D facility allowed to collect sample and provide a test orders on the global bio-surveillance and response system 200); and/or any other entity 208 (e.g., entities allowed to collect sample and provide one or more test orders on the global bio-surveillance and response system 200—for example, a nursing home, place of business, sporting and/or entertainment events, commercial stores, homeless facilities, apartment and/or condominium complexes, gated communities, and/or any other locale where people are willing and/or required to be tested. In embodiments, sample collection facilities may be located within or adjacent to sample processing and sample testing facilities, as discussed herein. In embodiments, one or more of the test collection facilities may be a part of a point of care (POC) network, as discussed in greater detail below.

One or more test ordering user computers 209 may provide the user with the ability to interact with the global bio-surveillance and response system 200 via networking platform 250, for example, to place one or more test orders and/or review results of the tests.

In further embodiments, the one or more test ordering user computers 209 may modify testing protocols in real time depending on particular changes observed or other inputs received throughout the global bio-surveillance and response system 200. In a non-limiting example, if test results from one or more sets of samples return particular results, changes in testing protocols (e.g., frequency of testing, which types of tests are to be administrated, how to run the tests, which individuals or groups of individuals should receive additional testing, what geographical locations should receive additional testing, etc.) may be ordered through one or more commands transmitted by the one or more test ordering user computers 209. In certain embodiments, the commands may be administered from a centralized location, or they may be divided among various locations (e.g., transmitted from a region proximate to the location the tests are to be performed). In still further embodiments, these functions described herein regarding these testing protocols may be performed by the system monitoring subsystem 220, or they may be performed through one or more test ordering user computers 209 and the system monitoring subsystem 220 working in concert with one another through networking platform 250.

In embodiments, test ordering computers 209 may provide test ordering instructions bi-directionally. For example, users of the test ordering computers 209 may employ the test ordering computers 209 to order testing kits and to order the testing of collected samples, as discussed below. Further, users of the test ordering computers 209 may employ the test ordering computers 209 to obtain or receive information regarding performing tests and/or sample collection.

The one or more computers may include a server, desktop, laptop, tablet, mobile device, and/or any other computing device running Windows, UNIX, Linux, MacOS, iOS, Android, and/or any other commercial, open-source, and/or special-purpose operating system with the software running on the operating system being either an operating-system native application; a web site accessed via web browser; a hybrid of operating-system native application with an embedded browser providing web content; or one or more independent applications each either being an operating-system native application or web site accessed via web browser.

The system monitoring subsystem 220 may include one or more mission control user computers 221, one or more monitoring data integration computers 222, one or more of which may be in communication with an external monitoring system 223. The system monitoring subsystem 220 may include a collection of one or more servers, desktop computers, laptop computers, tablets, and/or mobile devices provided within and/or connected with one or more computers used in the global bio-surveillance and response system 200. One or more mission control user computers 221 may provide users (for example, through permissions, restricted access, etc.) to view international and/or regional views of testing activity, as well as the overall performance of the global bio-surveillance and response system 200 via networking platform 250. These functions may include, for example, transitioning portions of or all testing capacity in sample processing subsystem 230 to pandemic (e.g., surge) testing, as well as returning to normal (e.g., surveillance or sentinel) testing for portions of or all testing capacity of sample processing system 230. Transitioning from sentinel to surge may be performed according to analyses of independent sample testing data, as discussed in greater detail below. In embodiments, these one or more mission control user computers 221 may additionally provide one or more users with the ability to view operational status of all sample processing subsystems 230 of the global bio-surveillance and response system 200 via cloud platform at 250, as well as remedy inventory, instrument, and/or personnel issues identified at sample processing subsystem 230 via cloud platform at 250. In embodiments, these one or more mission control user computers 221 may further provide one or more users with an integrated view of testing performed with the global bio-surveillance and response system 200.

One or more monitoring data integration computers 222 may provide for data exportation from the global bio-surveillance and response system 200 via cloud platform at 250 to one or more approved external monitoring systems 223 including, for example, health monitoring organizations at the local, county, state, provincial, national, and/or international level; news agencies; insurance provider(s); non-profit or for-profit health organization(s) and/or businesses; data aggregators for published content via web, electronic and/or print dissemination, and/or any other approved interested party.

Monitoring data integration computers 222 may provide de-identified data (DI data) to the external monitoring systems 223. As discussed herein, information and data collected related to one or more health conditions may include identified data (ID data) as well as de-identified data. Identified data may include testing data from one or more patients that includes information sufficient to identify the patient, e.g., social security number, name, date of birth, address, and others. De-identified data may include testing data that is stripped of identification data and contains information relevant only to the health condition testing.

Such information may extend beyond test results and include relevant demographic information (e.g., age, ethnicity) as well as relevant health details (underlying health aspects, weight, etc.). De-identified data may be selected or determined so as to meet appropriate legal and regulatory guidelines with respect to disclosure of patient health information.

Data discussed herein pertaining to patients may be characterized as either identified data (ID Data) or de-identified data (DI Data). ID Data includes one or more personal identifiers (e.g., name, address, social security number, etc.) of the tested individual that provides users and/or the global bio-surveillance and response systems discussed herein with the ability to associate that data (e.g., test results) with the individual who was tested. In contrast DI Data does not provide such indicators, so as to prevent users and/or the global bio-surveillance and response systems discussed herein from ascertaining whom the particular sample was collected from. In certain embodiments, ID Data and/or DI Data may further include additional attribute data, such as general demographic information, geographical information, etc. regarded the tested individual, but these attribute data abstract and/or aggregate individuals' personal identifiers, so that some additional characteristics may be associated with one or more individuals' samples, but so as to not any laws, regulations, policies, user preferences, etc. including those that monitor and regulate privacy and/or data protection concerns (e.g., HIPAA, GDPR, etc.).

In embodiments, DI Data may include information related to one or more individuals without providing personal identifiers described above. That information may include where an individual currently is, where that individual has been and when, with whom the individual has been in close contact with, etc. This may be accomplished through, for example, mobile device GPS tracking, credit card usages, etc. This information may be used, for example, for contact tracing (e.g., where the affected individual and/or a particular disease came from, identifying all of the locations that individual has been to recently, where the disease currently is, where it is spreading to, etc.); quarantine protocols (e.g., isolating some or all individuals within a certain proximity of the affected individual over a period of time as determined by the individuals' cell phones GPS tracking, for example by obtaining a list of all cell phone numbers that were in close proximity, etc.; isolating partially and/or fully insulated groups of individuals (e.g., an entire cruise ship where one or more of its passengers tests positive for a particular health condition, etc.); and/or ordering of additional and/or targeted testing to obtain, etc.

In embodiments, ID Data may be converted to DI data at the local level, e.g., at a sample collection facility and or point of care location. Such local conversion may prevent personalized details from entering the system in the first place. In further embodiments, ID Data is converted to DI data by the global bio-surveillance and response system (e.g., by a results module, as discussed below), as the data is received. In embodiments, the personally identifiable aspects of the ID data are removed and deleted by the results module 310 as they are received, to prevent accidental data breaches.

Given its nature, ID Data may only be shared with certain individuals and/or entities. Using a test sample as an example, ID Data may be shared with the tested individuals themselves, their doctors, and/or other designated individuals, etc. Other individuals and/or entities may also be designated to obtain ID Data including, not limited to, family members, medical facilities for which the individual is a patient, and/or other individuals and/or entities contractually obligated and/or permitted to obtain these data. In contrast, DI Data may be shared with a broader range of individuals and/or entities vis-à-vis ID Data. In a non-limiting example, DI Data may be shared with all individuals and/or entities that are permitted to receive ID Data, plus additional third parties, such as governments (local, state, federal, etc.), health monitoring organizations at the local, county, state, provincial, national, and/or international level; news agencies; insurance provider(s); non-profit or for-profit health organization(s) and/or businesses; data aggregators, etc. In certain embodiments, these data (e.g., as it relates to tests results) may exist in both forms—e.g., as ID Data and as DI Data—and stored separately so that different versions may be shared between and among different individuals and/or entities.

In some examples, the DI Data counterpart to the ID Data may include a version of data that strips away all personal identifies and in other examples, the personal identifiers are abstracted or otherwise obfuscated (e.g., provides the individual's approximate age (e.g., 40-45 years old), ethnicity, nationality, race, etc.). In other examples, two or more sets of ID Data may be combined together and the counterpart DI Data associated with that group of sets may provide an aggregated view of two or more of the individuals' identifying information, without violating any personal privacy and/or data privacy laws or regulations. In other examples, the ID Data, DI Data, or both may include additional information, such as who/what are permitted to receive the data, what may be done with the data, the manner in which it may be used, etc.

The DI Data, given that it may be more broadly distributed, may be particularly useful for various purposes, including, but not limited to the contract-tracing, quarantining, predictive testing, and/or load-balancing aspects of the embodiments described throughout because, for example, distribution of these data is not limited or restricted in the same manner as ID Data. In a non-limiting example, by freely sharing DI Data with health monitoring organizations, governments, etc. (and in turn, having those same organizations, etc. sharing similar data with the global bio-surveillance and response systems discussed herein (e.g., through one or more of the external monitoring system and/or monitor data integration computers (FIG. 2A, 223, 222, respectively)), the global bio-surveillance and response systems may be better informed as to how to best allocate resources globally (or in one more geographically limited regions) in a fluid and dynamic manner (e.g., where is the health condition currently, where is it predicted to grow to, at what rate, etc.). In embodiments, by freely sharing and/or exchanging these DI Data, the global bio-surveillance and response systems may be used as predictive tools to more efficiently load-balance resources (e.g., samples for testing, instruments, consumables, etc.), provide effective contact-tracing mechanisms, and/or better inform quarantine policies and procedures so as to mitigate and/or eliminate the spread of a health condition, such as a newly emerging pathogen that causes disease.

The sample processing subsystem 230, as shown in greater detail in FIG. 2A, may include Tier-1 farm lab operations 232, Tier-2 farm lab operations 233, Tier-3 farm lab operations 234, etc.; one or more of which may be in communication with one or more farm user computers 231. In embodiments, each of the farm lab operations 232, 233, and 234 may include one or more farm user computers located therein. In embodiments, the farm lab operations 232, 233, and 234 may be globally networked laboratories (GNLs), and or may be a part of a point-of-care network, as discussed in greater detail with respect to FIGS. 3A, 3B, 6A, 6C, and 7.

The sample processing subsystem 230 of the global bio-surveillance and response system 200 may include a collection of one or more servers, desktop computers, laptop computers, tablets, and/or mobile devices that may be part of or used in connection with the global bio-surveillance and response system 200, as well as any bio-instrumentation required in the processing of one or more of Tier 1 farm lab operations 232; Tier 2 farm lab operations 233, and/or Tier 3 farm lab operations 234. One or more farm user computers 231 may provide services in the global bio-surveillance and response system 200 via networking platform 250 (for example, through permissions, restricted access, etc.) to allow users to perform one or more of the following functions: view incoming orders and one or more report cards created (e.g., automatically) that is associated with each order; process test results; manage inventory; manage sample library; view and report instrument and personnel operational status, and other features relevant to maintaining a high level of operational status for a farm of the global bio-surveillance and response system 200.

As shown in FIG. 2B and discussed herein, Tier 1 farm lab operations 232 may include bioinstrumentation devices, such as high-throughput sample testing devices 271, sequencing devices 272, probe/primer synthesizing devices 273, assay development devices 274, inventory stockpiles 275, and more. Tier-2 farm lab operations 233 may include high-throughput sample testing devices 271, sequencing devices 272, and inventory stockpiles 275. Tier-3 farm lab operations may include high-throughput sample testing devices 271 and inventory stockpiles 275. Although discussed as discrete examples, various farm labs may have capabilities different than those discussed. For example, some Tier-2 farm labs 232 and/or Tier-3 farm labs 234 may possess or include one or more of the devices and capabilities discussed with respect to higher tier labs. Further details with respect to the different tiered labs are provided below. Further examples of instrumentation and devices associated with each Tier of labs may be found below, e.g., at Table 3.

In further examples, each of the tiered labs among the GNLs 700 may have a broader or narrower set of equipment and services offered as contemplated in the particular example described above. In addition to these labs, one or more depot facilities (e.g., three, but more or fewer are contemplated as well) may be used to stockpile equipment, consumables, etc., such as swabs, sample tubes, and other items needed for testing. Using the example of three, each may be strategically placed geographically (such as for example one in the United States, one in the European Union, and one in Asia, although other locations are contemplated as well). Under surge conditions, supplies may be able to be shipped out via air freight (or any other means of transportation) and distributed to one or more of those labs.

The independent sample testing subsystems 240 may include one or more distributed sentinel devices 241, one or more clinical lab operations 242, which may be in communication with one or more clinical data integration computers 243. One or more of these subsystems may be connected to one or more of the others through networking platform 250. The independent sample testing subsystem 240 may include a collection of one or more servers, desktop computers, laptop computers, tablets, and/or mobile devices that may be used within or in connection with the global bio-surveillance and response system 200, as well as bio-instrumentation required in the sample testing performed by one or more distributed sentinel devices 241 and one or more clinical lab operations 242. One or more functions of independent sample testing subsystem 240 may be performed in homes, doctor's offices, hospital labs, central reference labs, medical clinics, urgent care facilities, specialized testing facilities, pharmacy affiliated clinics, ambulances, mobile testing services; biopharmaceutical companies; biotech companies; contract research organizations; academic institutions; government agencies and/or departments; public health organizations; private health organizations; personalized medicine companies; translational medicine companies; and/or any other clinical entity capable of providing test results for samples to the global bio-surveillance and response system 200. In embodiments, the testing performed via the independent sample testing subsystem 240 may be targeted testing to detect one or more health conditions among a population to obtain targeted results.

One or more distributed sentinel devices 241 may provide their results directly to the global bio-surveillance and response system 200 via networking platform 250 (e.g., in real time) as they are being used in various locations (e.g., homes, doctor's offices, hospital labs, central reference labs, medical clinics, urgent care facilities, specialized testing facilities, pharmacy affiliated clinics, ambulances, mobile testing services; biopharmaceutical companies; biotech companies; contract research organizations; academic institutions; government agencies and/or departments; public health organizations; private health organizations; personalized medicine companies; translational medicine companies; and/or any other entity providing test results from a distributed sentinel device 241. The distributed sentinel devices 241 may include any appropriate type of bioinstrumentation devices, as discussed herein, such as cartridge readers, high-throughput sample testing devices, etc.

One or more clinical data integration computers 243 may include a collection of one or more servers, desktop computers, laptop computers, tablets, and/or mobile devices used within or in connection with the bio-surveillance system at 200. The one or more clinical data integration computers 243 may provide services in the global bio-surveillance and response system 200, and transmit information and data to and from other computers and/or subsystems via networking platform 250, for example, for transmitting data from one or more clinical lab operations 242 to the global bio-surveillance and response system 200 via cloud platform at 250. The one or more clinical data integration computers are configured to integrate sample testing data, for example, in situations where sample data is collected by a bioinstrumentation device and/or system in the clinical lab operation 242 that lacks a direct connection to the networking platform 250. The one or more clinical data integration computers 243 facilitate the provision of sample testing data to other aspects of the global bio-surveillance and response system 200 (e.g., the mission control subsystem) via the networking platform 250.

Figure 3A:
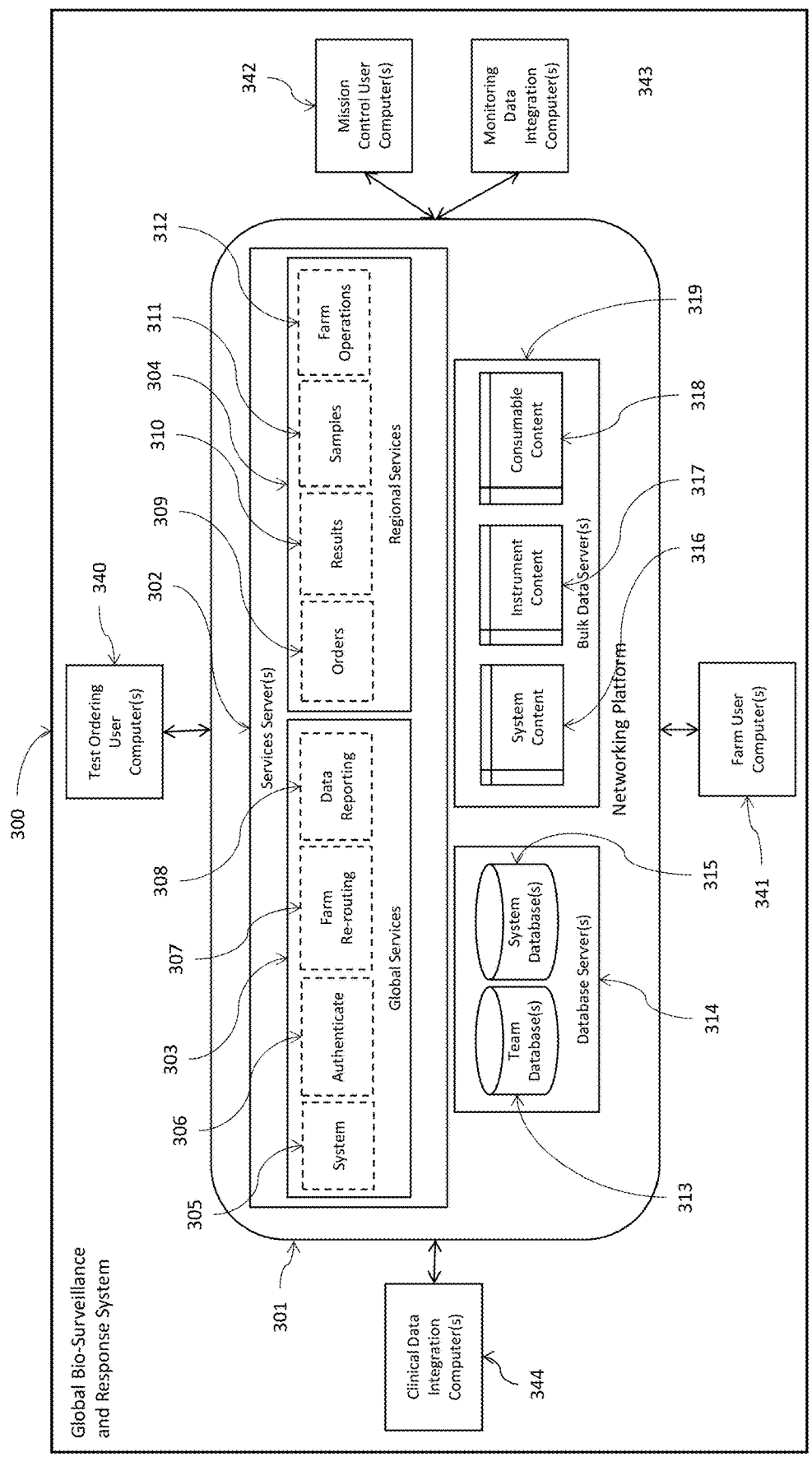
FIG. 3A depicts the system architecture of another embodiment of a global bio-surveillance and response system consistent with embodiments hereof.
Figure 3B:
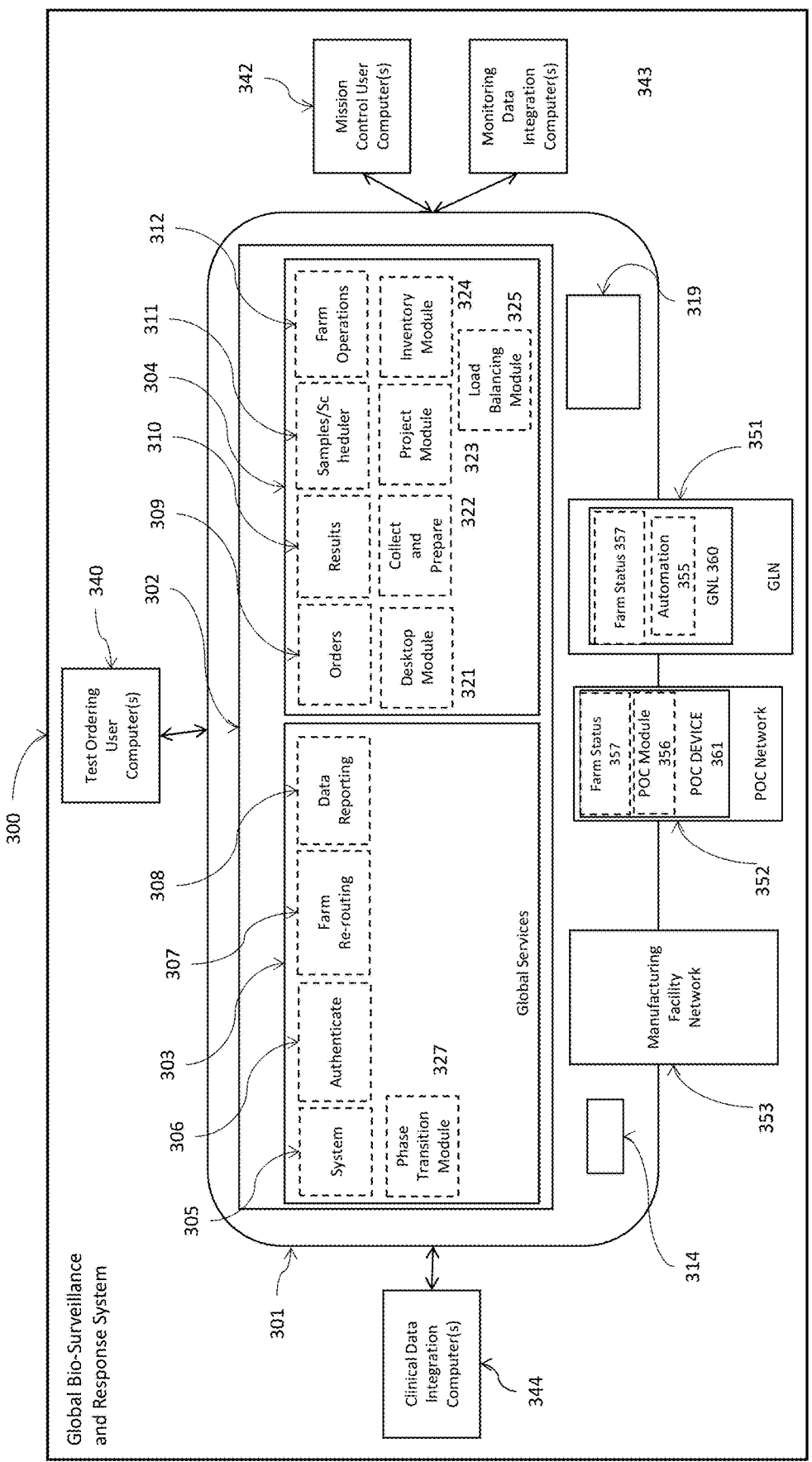
FIG. 3B depicts system architecture of another embodiment of a global bio-surveillance and response system consistent with embodiments hereof.

FIGS. 3A and 3B depict system architectures of further embodiments of a global bio-surveillance and response system in accordance with embodiments described herein. In embodiments, global bio-surveillance and response system 300 may provide a common computing, software services, and data architecture that may allow data to be collected and shared by any computer with associated software of global bio-surveillance and response system 300. Global bio-surveillance and response system 300 may provide these functions irrespective of where one or more computing devices with associated software is located within the world. In embodiments, global bio-surveillance and response system 300 may include networking platform 301, one or more test ordering user computers 340, one or more mission control user computers 342, one or more monitoring data integration computers 343, one or more farm user computers 341, and one or more clinical data integration computers 344. The services provided by the networking platform 301 are configured to integrate the operations of the sentinel subsystem, the surge subsystem, and the mission control subsystem. The global bio-surveillance and response system 300 is illustrated to provide additional details with respect to a system architecture and is understood to include any or all capabilities of the previously discussed global bio-surveillance and response systems 200 and 300.

The global bio-surveillance and response system ("global bio-surveillance and response system") 300 includes software systems, e.g., the networking platform 301, configured to perform various tasks including facilitating communication, data analysis, sample routing and tracking, testing protocol command and control, load balancing, etc., as discussed herein. In further embodiments, the networking platform 301 may form the foundation for security throughout the entire system. As used herein, "routing" may include the various tasks required to ship and/or facilitate the pickup and delivery of an item from a first location to a second location. For example, routing may include engaging a delivery service and scheduling pick-up and delivery of a sample. In embodiments, routing may refer to the printing of shipping labels and payment of shipping charges. Other aspects of shipping, transit, and delivery of items may further be encompassed by the term routing. In embodiments, the software of the networking platform 301 may be divided into various interrelated software modules that may provide a cohesive framework for the development, management, and scheduling of experiments and testing, as well as the analysis of results as test results are submitted by instruments within the network. In embodiments, the networking platform 301 may further include additional various modules working in concert with one another, and the hardware, firmware, and/or software distributed throughout the global bio-surveillance and response system 300, including the following systems and modules.

The networking platform 301 may include one or more services servers 302, which, in embodiments, may be bifurcated into two (or more) subservice servers—e.g., global services server 303 and regional services server 304. As shown in FIGS. 3A and 3B, the global bio-surveillance and response system 300 may include a global services server 303 including one or modules including a system module 305, an authenticate module 306, a farm re-routing module 307, and a data reporting module 308. As shown in FIG. 3A, the regional services server 304 may include one or modules including an orders module 309, a results module 310, a samples module 311, and a farm operations module 312. The networking platform 301 may further include one or more database servers 314, which may include, for example, one or more team databases servers 313 and one or more system databases servers 315. As shown in FIG. 3B, the regional services server 304 may further include desktop module 321, collect and prepare module 322, project module 323, inventory module 324, a load balancing module 325, and a phase transition module 327. The networking platform 301 may further include one or more bulk data servers 319, which may include, for example, one or more system content servers 316, instrument content serves 317, and consumable content servers 318.

In further embodiments, the networking platform 301 may serve as a hub or connection center for a global laboratory network (GLN) 351 comprising a plurality of globally networked laboratories (GNL) 360, a point of care (POC) device network 352 comprising a plurality of networked POC devices 361, and/or a manufacturing facility network 353. Further examples and descriptions of the global laboratory network 351 and the point of care device network 352 can be found below with respect to FIG. 6.

The global bio-surveillance and response system 300 may include one or more services servers 302, which may provide a scalable, robust, and high-performing computing and associated software platform to support services specific to the global bio-surveillance and response system 300. These servers may perform various functions, for example, retrieving, storing, transferring, and/or transforming data associated with the use of global bio-surveillance and response system 300. The one or more database servers 314 may be adapted to provide a scalable, robust, and high-performing computing and associated software platform for one or more structured databases, which may be used for storing and/or retrieving data produced by and/or for users of the bio-surveillance system at 300. Further, one or more of these databases may be used for storing and/or retrieving data produced and/or used by the global bio-surveillance and response system 300 as the system is being prepared for use and/or throughout use, for example, under surge conditions.

The databases described herein may include any database technology, including, for example, relational-based databases (e.g., SQL Server, Oracle, MySQL, Postgres, Aurora, and/or other related relational database technologies). In further embodiments, the databases may be non-relational in nature, e.g., Dynamo DB, Mongo DB, and/or other like non-relational database technologies. In various embodiments, one or more of the bulk data servers 319 may provide a scalable, robust, and high-performing computing and associated software platform for storing and retrieving file-based data provided for use of global bio-surveillance and response system 300 and/or produced through the use of global bio-surveillance and response system 300. The one or more services servers 302 may have associated with them, in certain examples, a logical collection of services organized in global services server 303, which may provide for services across the entire collection of regional deployments of global bio-surveillance and response system 300, and regional services server 304, which may provide services dedicated to a particular deployment region of global bio-surveillance and response system 300.

The global services server 303 may comprise one or more services and or modules, including: system module 305, authenticate module 305, farm re-routing module 307, data reporting module 308, and phase transition module 327. These modules implement various aspects of the sentinel, surge, and mission control subsystems, as described herein. Although the modules of the global services server 303 are described with respect to operation on the global services server 303, they are not so limited. In embodiments, where appropriate, the above-described modules may further operate on the regional services server 304 and/or on specific computing devices associated with the global bio-surveillance and response system 300. For example, aspects of the authenticate module 306 may operate on local computing devices to facilitate access to other aspects of the global bio-surveillance and response system 300 via the networking platform 301.

The system module 305 may include a logical collection of services and software to support administration and non-user-specific functions associated with the use of bio-surveillance system at 300. The system module 305 may include software functionality to support system administration functionality throughout the global bio-surveillance and response system 300. In embodiments, the system module 305 or instantiations thereof may also operate on the regional services server 304.

The authenticate module 306 may include a logical collection of services and software to support access control for the use of global bio-surveillance and response system 300. The authenticate module 306 may include software functionality to support access control functionality throughout the global bio-surveillance and response system 300. For example, access to the networking platform 301 and its various services, through any computing devices associated with the global bio-surveillance and response system 300 may be facilitated via the authenticate module 306. In embodiments, the authenticate module 306 or instantiations thereof may also operate on the regional services server 304 and/or on other computing devices associated with the global bio-surveillance and response system 300.

The farm re-routing module 307 may include a logical collection of services as software supporting re-directing orders (e.g., if a particular order cannot be currently processed within one or more target regions). The farm re-routing module 307 may further perform inventory re-distribution across regional deployments as required to meet testing needs; personnel re-distribution across regional deployments as required to meet testing needs; equipment, parts, and/or instrument re-distribution across regional deployments as required to meet testing needs; and any other additional services to support load balancing of the operational effectiveness and efficiency of various regional deployments, as required, to meet the testing needs for global bio-surveillance and response system 300. For example, the farm re-routing module 307 may be employed to facilitate inventory management across the global laboratory network 351, the POC network 352, and/or the manufacturing facility network 353, as described in further detail below. In particular, the farm re-routing module 307 may communicate with the inventory module 324 and load balancing module 325 of the regional services servers 304 to coordinate inventory management. As discussed below, the inventory module 324 and load balancing module 325 are configured to address inventory management issues across regional deployments of a GLN 351. Accordingly, the farm re-routing module 307 may communicate with inventory modules 324 and load balancing modules 325 associated with various regions to facilitate inventory management across (rather than just within) multiple regions. In embodiments, the farm rerouting module 307 or instantiations thereof may also operate on the regional services server 304 and/or on other computing devices associated with the global bio-surveillance and response system 300.

The data reporting module 308, may include a logical collection of services and software associated with collecting, receiving, and aggregating data (e.g., collected in real time, near real time, archived, or in bulk fashion) from across the various regional deployments of global bio-surveillance and response system 300. The data reporting module may, for example, present data via on one or more of the mission control user computers 342 and/or disseminate data to other computing devices associated with the global bio-surveillance and response system 300 via one or more monitoring data integration computer 343. Further the data reporting module 308 may perform the ingestion of sample test result data from one or more clinical data integration computers 344 and/or any other services associated with data global reporting that might arise. In embodiments, the data reporting module 308 or instantiations thereof may also operate on the regional services server 304 and/or on other computing devices associated with the global bio-surveillance and response system 300.

The phase transition module 327 may include a logical collection of services and software configured to manage transitions between one or more sentinel and surge phases, regionally and globally. The phase transition module 327 is configured to receive health condition data, e.g., deidentified data, from the data reporting module 308 and process the health condition data to make determinations regarding an operational phase of the global bio-surveillance and response system 300. Further details of the operation of the phase transition module 327 are described in greater detail below with respect to FIG. 7. In embodiments, the phase transition module 327 or instantiations thereof may also operate on the regional services server 304 and/or on other computing devices associated with the global bio-surveillance and response system 300.

The regional services server 303 may include one or more services and or modules, including an order module 309, a results module 310, a samples module 311, a farm operations module 312, a desktop module 321, a collect and prepare module 322, a project module 323, an inventory module 324, and/or a load balancing module 325.

The orders module 309 may include one or more services and or modules, including, for example, a logical collection of services and software to support receiving and retrieving sample testing orders for a particular regional deployment via, e.g., one or more test order user computers 340. The orders module 309 is configured to facilitate the receipt of sample testing orders from one or more computing devices associated with the global bio-surveillance and response system 300. Such computing devices may include, e.g., test ordering user computers 340 associated with any sample collection site as well as any devices or systems associated with the sample collection and test ordering subsystem 101. In embodiments, the orders module 309 or instantiations thereof may also operate on the global services server 303 and/or on other computing devices associated with the global bio-surveillance and response system 300.

The results module 310, which may include a logical collection of services and software configured to support receiving sample test results from one or more farm user computers 231/341 (as well as any devices associated with the GLN 351, POC network 352, and any other system or device supporting sample processing), retrieving sample test results from various sample test orders executed on a regional or local deployment of the global bio-surveillance and response system 300, and presenting the results via, e.g., one or more test order user computers 340 and/or any other computing device associated with the sample collection and test ordering subsystem 101, the system monitoring subsystem 102, etc. The results module 310 may be configured to receive deidentified data. In embodiments, the results module 310 or instantiations thereof may also operate on the global services server 303 and/or on other computing devices associated with the global bio-surveillance and response system 300.

The samples module 311, also referred to herein as the scheduler module 311, may include a logical collection of services and software for providing sample ship-to information for sample test orders received via, e.g., the or more test order user computers 340 and/or any other device associated with the sample collection and test ordering subsystem 101, as well as managing receipt, storage, accessioning, and preparation of samples for use in sample testing for global bio-surveillance and response system 300 via, e.g., the one or more farm user computers 341, the GLN 351, and/or any other sample processing system or device associated with the global bio-surveillance and response system 300. The scheduler module 311 is configured to manage, monitor, track, and otherwise handle and coordinate health condition monitoring sample collection as discussed herein. As discussed above, the sample collection and test ordering subsystem 101 includes devices, instrumentation, facilities, and personnel associated with the collection of biological samples. The scheduler module 311 provides instructions to these devices, instrumentation, facilities, and personnel, e.g., in the form of software commands to devices equipped to respond as well as alerts and other instructions to personnel associated with the devices, instrumentation, and facilities. Such instructions are configured to facilitate the collection, shipping, and transport of collected samples to the appropriate sample processing facilities. The scheduler module 311 is further configured to facilitate the shipping and transport of collected samples.

Figure 5:
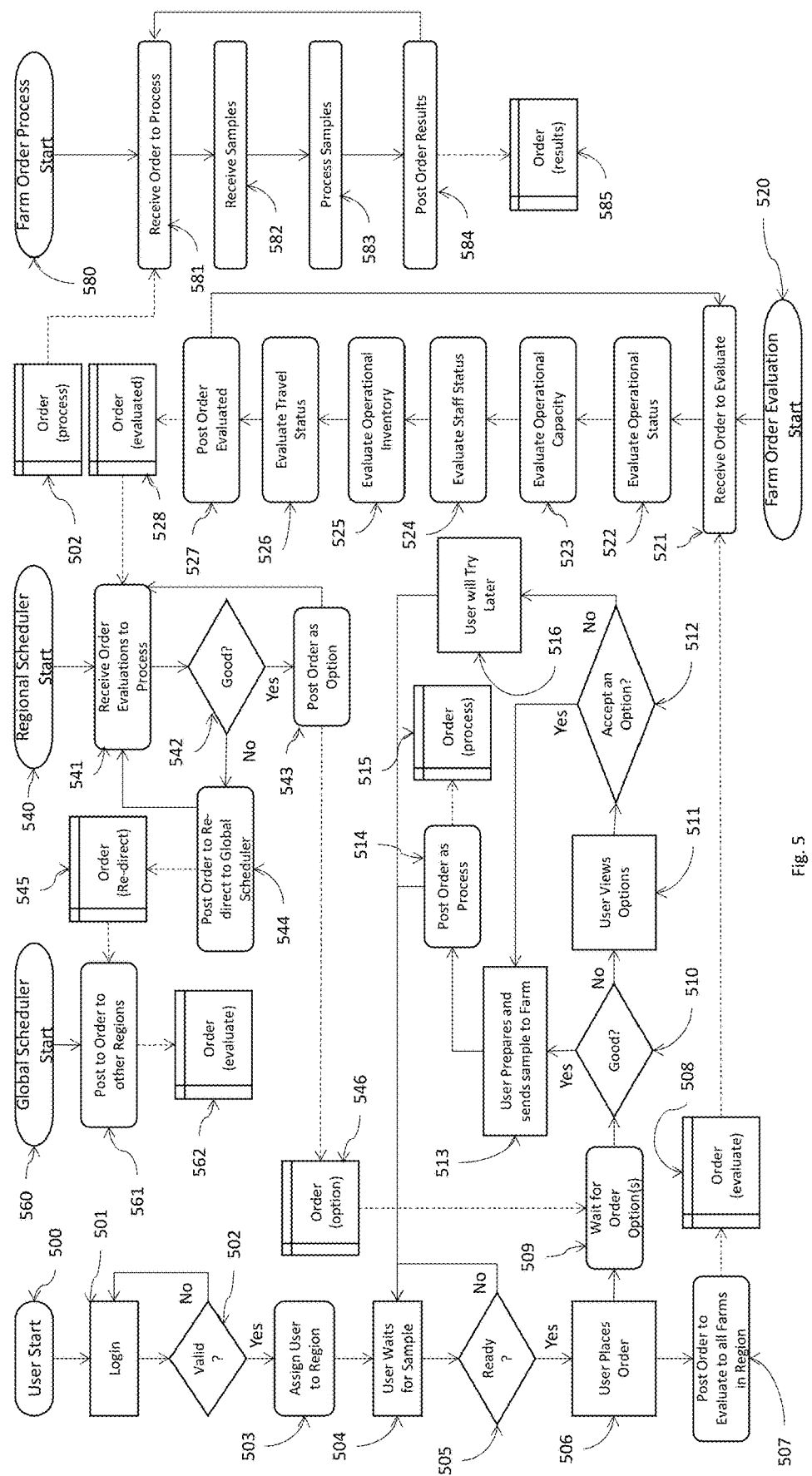
FIG. 5 depicts a non-limiting, illustrative embodiment of various processes of a global bio-surveillance and response system that may be carried out in accordance certain aspects of the disclosure.

The scheduler module 311 may further be configured to facilitate the scheduling of testing across all the instruments of the GLN 351 (e.g., individual instruments, farms of instruments, etc.), directing and/or diverting samples collected in the field to labs with available testing capacity, while balancing sample travel times. The scheduler module 311 may rely on one or more of software, algorithms, artificial intelligence, machine learning, etc. to optimize the routing and load-balancing of these samples. A more detailed discussion of the scheduler module 311 and its functionality is presented below with respect to that global scheduler processes (e.g., 560-562); regional scheduler processes (e.g., 509-585); farm order processes (e.g., 580-585); and/or user processes (e.g., 500-585), as shown in FIG. 5. In embodiments, the scheduler module 311 or instantiations thereof may also operate on the global services server 303 and/or on other computing devices associated with the global bio-surveillance and response system 300.

The farm operations module 312 may include a logical collection of services and software associated with the optimal operation of a sample testing farm in the global bio-surveillance and response system 300 via, e.g., the one or more farm user computers 341. The farm operations module 312 may include functionality for one or more of: inventory monitoring and management for the consumables and supplies that may be necessary for the operation of a sample testing farm; instrument operational status monitoring and management that may be necessary for the operation of a sample testing farm; personnel operational status monitoring and management that may be necessary for a sample testing farm, and any other services that may be deemed necessary for the operation of a sample testing farm. The farm operations module 312 may be configured to communicate with one or more devices from the GLN 351, the POC network 352, etc. In embodiments, the farm operations module 312 or instantiations thereof may also operate on the global services server 303 and/or on other computing devices associated with the global bio-surveillance and response system 300.

The desktop module 321 may include a logical collection of services and software configured to permit users to design experiments that may be distributed (automatically or otherwise, via the networking platform 301) to available instruments (e.g., P5 instruments, instruments associated with the GLN 351, instruments associated with POC network 352, and/or instruments associated with the various farm operations 232, 233, 234, etc.) in concert with the scheduler module 311. The desktop module 321 may further be configured to provide tools to permit the user to analyze data received from various instruments in the global bio-surveillance and response system 300 that was produced in response to the defined experiments. See, e.g., U.S. Application No. PCT/US2019/042274, filed on Jul. 17, 2019, each of which is incorporated herein by reference. Accordingly, the desktop module 321 permits operators and users of the global bio-surveillance and response system 300 to design and implement experiments via remote laboratory and instrumentation locations. In embodiments, the desktop module 321 or instantiations thereof may also operate on the global services server 303 and/or on other computing devices associated with the global bio-surveillance and response system 300.

The collect and prepare module 322 may include a logical collection of services and software configured to provide instructions to users, e.g., operators associated with the GLN 351, the POC network 352, and/or any other bioinstrumentation devices associated with the global bio-surveillance and response system 300 for sample processing. As users design experiments through the desktop module 321 and schedule the same through the scheduling module 311, lab workers and/or other personnel may utilize the collect and prepare module 322 to carry out the previously designed experiments. In embodiments, the collect and prepare module 322 may be operate on a tablet or other mobile or computing device. Based upon selection of an experiment to carry out, the collect and prepare module 322 may, through text, video, audio, and/or pictorial instruction, walk users though the collection of reagents, consumables, samples, and other items needed for the experiment and then instruct those users through the preparation of all samples, reagents, and consumables for the experiment. See, e.g., U.S. Provisional Patent No. 62/964,435, filed Jan. 22, 2020 and PCT/US2021/014379, filed Jan. 21, 2021, both of which are incorporated herein by reference. Accordingly, the collect and prepare module 322 facilitates sample processing by providing the requisite instructions to remote laboratory operators without the requirement for onsite training. Thus, a scientist, for example, working and designing experiments at a university via the desktop module 321, may facilitate the and cause the execution of those experiments at any laboratory within the global bio-surveillance and response system 300 having the appropriate consumables, equipment, and personnel via the scheduler module 311 and the collect and prepare module 322. In embodiments, the collect and prepare module 322 or instantiations thereof may also operate on the global services server 303 and/or on other computing devices associated with the global bio-surveillance and response system 300.

The project module 323 may include a logical collection of services and software configured to enhance collaboration between users of the global bio-surveillance and response system 300. The project module 323 may be used by lab managers, scientists, and/or other personnel to group associated experiments and resulting data into specific projects. Accordingly, data collected by one user may be grouped or associated with related data (e.g., from the same region, from patients of similar demographics, from the same experiment, etc.) from other users to permit collaboration across the entirety of the global bio-surveillance and response system 300. In embodiments, the project module 323 or instantiations thereof may also operate on the regional services server 304 and/or on other computing devices associated with the global bio-surveillance and response system 300.

The inventory module 324 may include a logical collection of services and software configured to track the current inventory of assay kits, consumables, reagents, equipment, personnel, and any other necessary resource at the various laboratories, processing facilities, etc., associated with the global bio-surveillance and response system 300. The inventory module 323 may further be configured to communicate with the manufacturing facility network 353 (including warehousing locations) to track and monitor the current available supply of resources as well as the near-term and long-term availability of resources (e.g., based on projected manufacturing schedules).

The inventory module 324 may operate in coordination with the desktop module 321 and the schedule module 311, for example, to advise experiment creators on what experiments may be run with existing kit and consumable inventory. The inventory module 324 may further provide the capability to automatically order materials not present in local inventory to support planned experiments. Under surge conditions, the inventory module 324 may integrate information from the system monitoring subsystem 102, the sample collection and test ordering subsystem 101, the GLN 351 (Tier 1 and Tier 2, Tier-3, etc. labs), the POC network 352, the manufacturing facility network 353, and data obtained via user devices (e.g., a mobile-based app as described in greater detail below) to direct and/or divert inventory of assay kits, supplies, consumables, and/or any other shippable or transportable resource (including equipment and personnel where appropriate) to maximize testing throughput and efficiency. The inventory module 324 may rely on one or more of software, algorithms, artificial intelligence, machine learning, etc. to optimize the routing and load-balancing of these samples. An example of inventory module 324 operation is provided in greater detail below with respect to FIG. 5 and global scheduler processes (e.g., 560-562); regional scheduler processes (e.g., 509-585); farm order processes (e.g., 580-585); and/or user processes (e.g., 500-585). In embodiments, the inventory module 324 or instantiations thereof may also operate on the global services server 303 and/or on other computing devices associated with the global bio-surveillance and response system 300.

In embodiments, the inventory module 324 and the scheduler module 311 may be configured to perform predictive modeling of anticipated needs to influence sample processing scheduling and inventory routing. For example, with respect to inventory routing, the inventory module 324 may employ machine based learning and/or artificial intelligence techniques as applied to previous data sets to estimate future demand and/or inventory planning. For example, based on previous data, it may be predicted that a new pathogen may spread quickly through certain populations (e.g., college campuses). Detection of a new pathogen in such an area may trigger a response to send additional inventory, instruments, consumables, human resources, etc. to specific laboratories of the GLN 351 close to the area, in anticipation of rapidly increasing caseloads. Similarly, the scheduler module 311 may employ similar techniques in scheduling sample processing. In areas where caseloads are expected to rise rapidly, sample processing scheduling may be based on future predicted loads and thus the processing capacity of neighboring but not local laboratories of the GLN 351 may be employed earlier in the process to maintain a high throughput through the system as the case load ramps up.

The load-balancing module 325 may include a logical collection of services and software configured to balance sample processing loads and inventory loads across the multiple laboratories, POC devices, etc. across the global bio-surveillance and response system 300. The load-balancing module 325 is configured to operate in conjunction with the scheduler module 311 to balance the sample processing load across the various sample processing systems associated with the global bio-surveillance and response system 300 to increase, maximize, and/or optimize the total sample processing throughput. The load-balancing module 325 is configured to operate in conjunction with the inventory module 324 to ensure that inventories are maintained across the sample processing sites associated with the global bio-surveillance and response system 300 to increase, maximize, and/or optimize the total sample processing throughput. In embodiments, the load balancing module 325 or instantiations thereof may also operate on the global services server 303 and/or on other computing devices associated with the global bio-surveillance and response system 300.

In embodiments, the load-balancing module 325 is configured to address the potential tradeoff between queuing samples and transporting samples. For example, a well-staffed and well-stocked GNL 360 of the GLN 351 most proximate to an outbreak location may, initially, appear to be an optimal location for sample routing. As more samples are routed to that GNL 360, queue times may lengthen and supplies may dwindle, which in turn may make other laboratories better locations to receive samples so as to maintain a high throughput across the entire GLN 351.

Real-time algorithms may be employed to balance a sample load across multiple GNLs 360 and across the entirety of the GLN 351. Such algorithms may optionally be backed by human analysts that may make real-time adjustments to the algorithm variables in terms—e.g., based on how long the algorithm allows testing queues to build up at local GNLs 360 before routing sample packages to other network GNLs 360.

In embodiments, the load balancing module 325 may be configured to balance inventory loads, consumables, other equipment, and/or instruments, etc. according to selection criteria including simple ratio/percentage formulas. For example, simple ratios and/or linear formulas may be applied (e.g., if positive test results double for a particular test location, double the amount of test supplies (e.g., swabs, cartridges, etc.) that are typically routed to that location. This may apply to other resources as well—e.g., instruments, personnel, washers, shakers, etc. Accordingly, a load balancing algorithm may be based on a positivity rate at a particular GNL 360.

In embodiments, the load balancing module 325 may be configured to balance inventory loads according to selection criteria including thresholds. For example, when a certain resource drops below a threshold (e.g., fewer than 4 days (during baseline levels of processing) of cartridges remain stockpiled, allocate more to the site. The thresholds themselves may be dynamic and tailored to circumstances through simple formula (if testing has doubled in that site, the threshold is adjusted accordingly (from 4 days to 2 days, etc.). Thresholds may also be adjusted according to a number of samples routed to a site—e.g., if the samples module routes additional samples to a site for processing, the load balancing module 325 may route inventory items to the same site to keep pace.

In embodiments, the load balancing module 325 may be configured to predictively balance sample, consumable, and/or inventory loads across the global bio-surveillance and response system 300. For example, the load balancing module may be configured to project future inventory and future sample processing times according to amounts of inventory and samples routed to one or more of the GNLs 360. For example, a GNL 360 may currently have a high capacity and high inventory, causing the load balancing module 325 to route newly collected samples to this location. Due to shipping transit times, the GNL 360 may continue to show high inventory and fast sample processing times for several days because the shipped samples have not yet arrived for processing. Accordingly, the load balancing module 325 may be configured to project future sample processing times and future inventory needs, routing additional inventory to the well-stocked GNL 360 in anticipation of the arrival of the en-route samples and distributing future samples to different GNLs 360 in anticipation of the arrival of the en-route samples (and associated queue lengthening).

The automation module 355, which may operate on one more computing devices associated with a GNL 360, includes a collection of services and software configured to facilitate the automated, autonomous, and/or semi-autonomous operation of instruments associated with the global bio-surveillance and response system 300. The automation module 355 may operate directly on instruments, such as high throughput instruments, e.g., P5 instruments, may accept experiments from the networking platform 301 (e.g., via the desktop module 321 and the scheduler module 311), run those experiments on samples and kits that are loaded onto the instrument, and submit the resulting data, e.g., through the network platform 311. The automation module 355 may also provide instructional load and unload functionality (e.g., according to the collect and prepare module 322) that walks the user through the necessary steps required to do operate the high-throughput instrument. In embodiments, some or all of the functionality of the automation module 355 may be implemented by the networking platform 301.

The farm status module 357, which may operate on one more computing devices associated with a GNL 360, includes a collection of services and software configured to assess and communicate the operational health of the global bio-surveillance and response system 300. The farm status module 357 may operate to communicate with various automated aspects of a given GNL 360 as well as maintain records and data associated with and indicative of a status of the GNL 360. The farm status module 357 is further configured to apply one or more sets of computational rules to lab status data to determine laboratory evaluation information including a laboratory health score and an estimated time to result, e.g., by a scorecard method as discussed below with respect to FIGS. 6A-6C. The farm status module 357 may further be configured to communicate with the regional services server 304, e.g., the scheduler module 311, to provide scorecard data about an associated laboratory. In embodiments, some or all of the functionality of the farm status module 357 may be implemented by the networking platform 301.

The POC module 356 includes a collection of services and software configured to facilitate the automated, autonomous, and/or semi-autonomous operation of devices and instruments associated with the POC network 352. The POC module 356 may operate directly on one or more POC devices, for example cartridge readers, and may be configured to host the POC device user interface, automate a cartridge processing sequence, and upload results, for example, to the networking platform 301. In embodiments, some or all of the functionality of the POC module 356 may be implemented by the networking platform 301.

The various modules as discussed herein represent collections of services and software configured to provide the functionality described herein. In embodiments, one or more modules may perform, possess, or otherwise exhibit functionality related to other modules as described herein. For example, the load balancing module 325 may perform some of the same inventory management and tracking functionality as described herein with respect to the inventory module 324. Other examples may also occur.

Services servers 302 may be adapted to be an easily scaled computing infrastructure based upon, for example, one or more servers that may include and/or carry out the functions of one or more of the services and/or modules the services servers 302 may provide (e.g., one or more of modules depicted in FIGS. 3A/3B, 305-312, 321-324). In embodiments, the services servers 302 may facilitate a load balancer to equally distribute requests for services (or, in other examples, perform some other, non-equal distribution of requests) across the one or more servers of services servers 302, which may result in the optimization of users' interactions. In embodiments, the load balancing techniques described herein may be implemented through a logical collection of services and/or modules (e.g., one or more of modules depicted in FIGS. 3A/3B, 305-312, 321-324) that employ a RESTful (representational state transfer) design pattern. In these examples, each provided service may be stateless, such that it does not store or hold data. With this configuration, any request made on the service may be fulfilled by any available server the service is deployed on from among the one or more services servers 302 based on demand at the time of request.

To support optimal deployment and operation of the logical collection of services and/or modules (e.g., one or more of modules depicted in FIGS. 3A/3B, 305-312, 321-324) on one or more computers, these services may be built, for example, on one or more distributed-object platforms, e.g., Java Platform Enterprise Edition, which is capable of supporting cross-platform computing architectures; .NET Framework for Windows-only computing architectures; or other distributed-object platforms. In further embodiments, these services and/or modules may include some combination of one or more of these distributed-object platforms.

Figure 4:
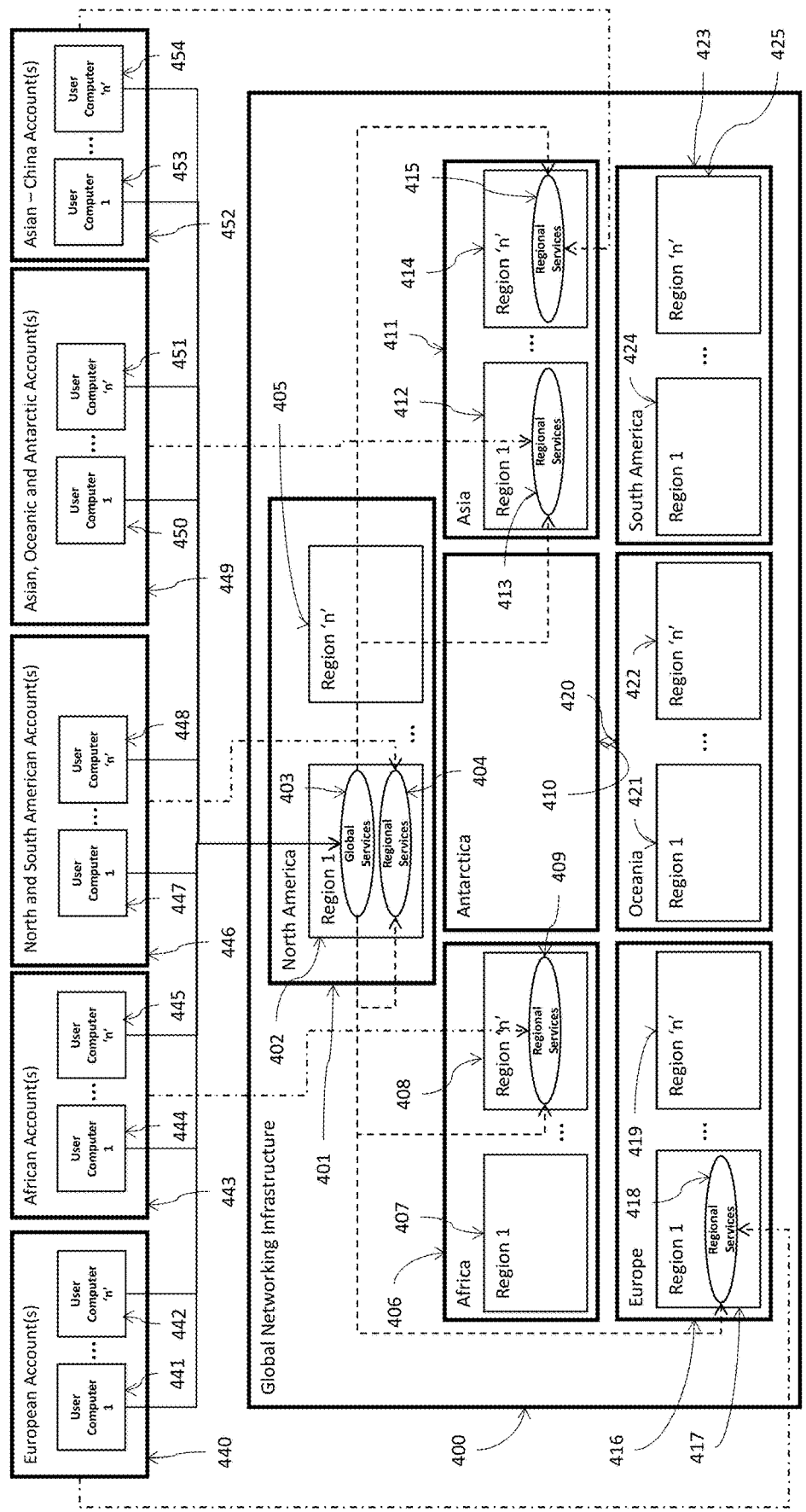
FIG. 4 depicts a non-limiting, illustrative embodiment of an international deployment of a global bio-surveillance and response system in accordance with the certain aspects of the disclosure.

FIG. 4 depicts a non-limiting, illustrative embodiment of an international deployment of a global bio-surveillance and response system in accordance with the certain aspects of the disclosure. In embodiments, international networking infrastructure 400 may be adapted to maintain physical computing installations in various regions on associated continents on the planet. In examples, the international networking infrastructure 400 may be implemented as a cloud networking infrastructure.

International networking infrastructure 400 may have associated with it various accounts (e.g., European Accounts, 440; African Accounts, 443; North and South American Accounts, 446; Asian, Oceanic, and Antarctic Accounts, 449; and Asia-China Accounts, 452). One or more of these accounts may include one or more user computers (e.g., 441, 442, 444, 445, 447, 448, 450, 451, 453, and 454). International networking infrastructure 400 may further cover one or more continents across the world (e.g., North America, 401; Africa, 406, Antarctica, 410; Asia, 411; Europe, 416; South America, 423; and Oceania, 420).

Each continent may be divided into one or more Regions (e.g., 402, 405, 407, 408,412, 414, 417, 419, 421, 422, 424, and 425, etc.). Each region may include one more of global services servers (e.g., 403) and/or regional services servers (e.g., 404, 409, 413, 415, and 418), e.g., as discussed above with respect to FIG. 3 (e.g., 303, 304).

More particularly, in this example, the continents include North America 401, Africa at 406, Antarctica at 410, Asia at 411, Europe at 416, Oceania at 420, and South America at 423. Each continent may include one or more Regions, e.g., North America 401 with Region 1 (402) and Region 'n' (405), with the ellipse between them to denote the potential for any number of regions, with this pattern repeated for each continent, including, for example, those that have physical computing installations, and those that do not (e.g., Antarctica, in this example, does not have a physical computing installations. One or more of these regions may include the computing infrastructure required by method, systems, and apparatuses described herein to deploy software for their operation and use. Which region or set of regions are selected to deploy these systems, methods, and apparatuses, may depend on support, performance, and operational robustness needs and/or constraints, as well as government laws and regulations governing where physical data storage and/or computing must be maintained.

The countries on various continents may each be mapped to regions on the global networking infrastructure 400, for example, based on performance needs and/or government constraints. In this regards, when accounts are created for users residing on various continents, their use of these systems may be directed to the appropriate region on the global networking infrastructure 400 as depicted, for example, by the dotted line. In this non-limiting, exemplary embodiment, the dotted lines are drawn from European Accounts 440 to regional services 418, thus indicating that all European users may be required to use regional services 418. In some embodiments, all users, regardless of where they are located, may login through global services 403 in North America 402 with, for example, their login connecting them to their appropriate region on the global networking infrastructure 400.

To support global connection of, these systems, in this particular embodiment, North America 402 was selected as the "home base" for the system with both global services 403 and regional services 404 deployed to Region 1 402, which may be referred to as Eastern United States as an example. In further embodiments, other continents, global services, regional services, and regions may be selected as well. Global services 403 may be provided by systems in more than one continent and/or more than one region. Additional regional deployments, for example, may be made to Region 'n' 408 in Africa 406 for regional services 409; Region 1 417 in Europe 416 for regional services 418; Region 1 412 in Asia 411 for regional services 413; and Region 'n' 414 in Asia 411 for regional services 415 for China, etc. The final example is provided for illustrative purposes to account for the governmental restrictions on data storage being physically maintained in China proper. The global connection between all deployed regions may be made via global services 403, which may be configured to have awareness of one or more deployed regions as denoted by the dotted line between global services 403, in this particular embodiment, and each of the deployed regions at 404, 409, 413, 415, and 418. In embodiments, each region may perform autonomously from both global services 403, as well as all other deployed regions at 404, 409, 413, 415, and 418, by way of example.

The autonomous operation described herein may provide for optimal (fully or partially) load balancing of global testing, as well as for providing fail-overs via global services 403, for example, when a particular region has encountered problems and/or complications with its receiving sample tests and its testing load due, for example, to factors internal and/or external to a sample testing farm. External factors negatively affecting turnaround of sample testing farm results may include one or more of weather, travel problems, public and/or government unrest, utility failure including internet, natural disasters, and/or any other external disturbances, to name a few. Internal factors negatively affecting turnaround of sample testing farm results may include sample test ordering load, inventory and consumable levels, personnel availability, equipment issues, parts issues, instruments, and/or other internal problems, to name a few. The fail-overs via global services 403 may provide for re-distribution to other regions of orders, samples, inventory, personnel, equipment, parts, instruments, consumables and/or anything else that might be needed to meet the testing demands, for example via the farm re-routing module 307 as described above.

The global users of systems, methods, and apparatuses described herein may be located in a country on any continent on the planet as depicted at, for example, 440, 443, 446, 449, and 452. In one such example, European Accounts 440 may consist of one or more users each using any number of user computers as depicted, for example, by user computer 1 (441) and user computer 'n' (442) with the ellipse between them to denote the potential for any number of computers, with this pattern repeated for each continent. In further embodiments, one or more users of one or more accounts may be in a country different than that assigned to an account, in which case, the one or more users may default, for example, to use the regional services assigned to that particular account.

FIG. 5 depicts a non-limiting, illustrative embodiment of various processes of a global bio-surveillance and response system that may be carried out in accordance certain aspects of the disclosure. In embodiments, the processes disclosed may include, for example, one or more global scheduler processes (e.g., 560-562); regional scheduler processes (e.g., 509-585); farm order processes (e.g., 580-585); and/or user processes (e.g., 500-585).

More particularly, FIG. 5 includes an embodiment of an algorithm by which sample test orders may be processed and routed by the global bio-surveillance and response system. A sample testing user, e.g., a clinician, doctor, home user, etc., that has collected a sample requiring testing may start at 500 logging in to the global bio-surveillance and response system via an appropriate computing device (e.g., a computing devices associated with the sample collection and test ordering subsystem 201, at 501. If a valid login is found at 502, e.g., via a user authentication module 305, the user is assigned the region in which their account is operating. The user may then be required to wait to receive a sample at 504. For example, a user anticipating receipt of a sample (or multiple samples) may use the global bio-surveillance and response system to determine routing for the sample(s) while awaiting the sample. At 505, upon receiving the sample(s), the user may enter their testing order at 506, saving their order at 507. The steps of placing and saving a test order may be implemented, for example, by the order module 309 in operation on a regional services server associated with the user's assigned region.

Having placed an order or orders, the user may wait for instructions as to where to ship the sample for testing at 509. A samples module 311 operating on a regional services server 304 associated with the user's assigned region may evaluate the order, e.g., at 520, described below. Once options for sample processing (e.g., one or more sample processing subsystems 103) are identified as options the user may review the options at 510. As discussed below, the options may be provided with estimated times to result as well as destination laboratory scores. If the primary option is selected, the user may advance to 513 to prepare the sample to send to one or more farms (e.g., Farm Lab Operations 232, 233, 234) using provided instructions and a printed label. If the primary option is not selected at 510, the user may review additional options at 511, choose an option at 512, and/or determine to select an option at a later time at 516. Upon selection of an option and preparation of a sample, the samples module 311 may post the order as a process at 514 and queue the order for processing by a specific farm lab operation (e.g., 232, 233, 234) at 515. The user may then be ready for their next sample order.

In embodiments, preparing samples for shipment may include removing identifying data from the sample. Accordingly, a sample may be shipped for processing without any data identifying the patient from whom the sample was obtained. Identification linking the sample to the patient, e.g., for reporting to the patient, may be maintained locally at the sample collection facility.

At 520, the system, e.g., the samples module 311, may begin a process to evaluate one or more orders that come from the user (or multiple users) and the suitability of various farm operation labs to process the order. In embodiments, the sample module 311 may obtain information related to the farm operation labs from the farm operations module 312. At 521, the system e.g., the samples module 311, may attempt to retrieve orders to evaluate from one or more users, including the user described above. Upon receiving the orders, the samples module 311 may, at 522, for example, evaluate the operational status of the instruments and infrastructure of one or more farms. The one or more farms may be provided with a score between 0 and 100 (100 being best) indicative of its operational status based on, e.g., the current working status of instruments and facilities, and historical operational performance. In further embodiments, the farm order evaluation process at 520 may proceed according to the score-card determination and load balancing method as disclosed below with respect to FIG. 6.

The operational status score can be applied to instruments (e.g., POC devices), equipment (e.g., washers, shakers, etc.), etc. This status could refer to the health of instrument, piece of equipment, etc., which assigns a percentage to each instrument and piece of equipment based its overall health. For example, a new cartridge reader may be assigned a value of 90%-100%, whereas an older one by comparison that will soon require routine maintenance may be assigned a value of 50%-60% (although other values greater or less than are contemplated as well). In another example, if a piece of equipment or instrument is offline or down, it could be assigned a value of 0%, or some other percentage value (e.g., 10%, 20%, etc., although other values greater or less than are contemplated as well), if, for example, an offline instrument is known to be partially or fully operational in a period of time. In an example, if a POC device is offline for 2 days and samples must be run over a 4-day period, a value of 50% could be assigned to that device.

Then, at 523, the system, e.g., the samples module 311, may evaluate the one or more farm's operational capacity scoring between 0 and 100 (100 being best) based on the utilization of the instruments, e.g., the current testing load and availability of instruments at the one or more farm. For this factor, rather than evaluating the status of each instrument, piece of equipment, etc., the farm can be evaluated as a whole. Thus, the total operational capacity can be determined by evaluating one or more of the present and future expected utilization levels of the instruments and equipment within a particular farm. In some examples, equipment and/or instruments that are more heavily utilized (e.g., a state-of-the-art assay analyzer) can be assigned a higher percentage as compared to equipment and/or instruments that are utilized less frequently, thus allowing the system to appropriately weigh and factor these considerations before assigning a score for a farm's operational capacity.

Next the system, e.g., the samples module 311, may evaluate the personnel and/or staffing status at 524 scoring between 0 and 100 (100 being best) based on, for example, working staff, their open time, future scheduling, as well as the available staff's historical capability. Historical capabilities can include, for example, the mean number of annual days of sick leave taken at a particular farm, staff members' overall efficiency while working (e.g., as determined based on performance review, etc.), etc. This factor can further take into consideration additional aspects of staff members' schedules and/or availability. For example, if a particular farm has a significant group of staff members willing and available to accept overtime hours, that farm could be assigned a higher personnel status score as compared to another farm with equal number of available staff members unable to accept those hours. In this sense, the total number of staff members is not only taken into consideration, but also the employees' overall efficiency, health, availability to work, historical work habits, etc. can all be weighed in determining this score.

Next, the system may evaluate the operational inventory at 525 required to process the order scoring between 0 and 100 (100 being best) based on the availability of the inventory to perform the test as well as the inventory historical capability. In examples, the operational inventory can be further broken into several categories including inventory that is presently available to use, such as inventory currently on hand, shipments of additional inventory that is expected to arrive, automatically replenished inventory (e.g., inventory known to be re-ordered automatically when the inventory drops below a certain threshold), etc. For example, if the operational inventory of a farm is being determined over a seven-day period, the system would evaluate and weigh the inventory currently on hand, the inventory expected to arrive in the next several days, and additional inventory that will be replenished as a result of the inventory dropping below a threshold value. In this sense, the operational inventory score, in certain embodiments, will vary depending on the amount of time needed to process the total sample set. For example, in a non-limiting exemplary embodiment, Farm 1 may have a higher operational inventory score as compared to Farm 2 if the selected farm has three days to process the results but Farm 2 may have the higher operational inventory score as compared to Farm 1 if the selected farm has ten days to process the results (e.g., because Farm 2 has a significant replenishment of supplies due to arrive in four days). Other examples are contemplated as well.

Next the system may evaluate travel status at 526 for current travel conditions, weather conditions and forecast, local and/or government unrest, construction, accidents, and historical execution of travel, etc. from order locations scoring between 0 and 100 (100 being best) based on the quality of external condition and historical performance. The travel status can include, for example, travel of supplies from an order location to one or more farms, or it could include personnel travel from their homes to work. In this sense, this factor can evaluate aspects that might potentially hinder available resources (e.g., additional equipment, staffing levels) from being deployed to one or more farms. These aspects may be further defined as short-term (such as, for example, a minor snowstorm), mid-term (natural disaster, such as an earthquake), or long-term (such as, for example, a coup overthrowing a government). The system can weigh and balance each of these factors when computing a travel status score.

After completing the evaluations, the system may calculate its score by weighting and averaging the scores for the one or more farms. The samples module 311 may then establish a time to result for the order and the probability of success hitting the time to result based on historical performance and/or a scorecard, e.g., as determined according to the methods discussed with respect to FIG. 6, and then it may post at 527 the full evaluation report (e.g., scorecard) at 528 to one or more databases within the system, with the goal of optimizing that result. Time to result here may include one or more of the time it takes process samples, time to deliver samples, time to prepare samples, etc. In some examples, the straight mean of one or more of the above factor is calculated, without ascribing weight to any one particular factor. In other example, one or more of the above factors can be weighed first, then averaged to compute the final score. By way of example, a farm located in a location that is highly prone to disruption from natural disaster and civil unrest may place a stronger emphasis on the travel status score than the operational inventory score. Other examples are contemplated as well. Results optimization can be determined on a batch-by-batch basis and/or individual sample basis. Optimization can further include splitting a batch between or among two or more farms.

In embodiments, the samples module 311 may provide, at 527, time to result information and laboratory scorecard information for multiple laboratories as determined according to the scorecard method discussed with respect to FIG. 6. In embodiments, the laboratory evaluation information may be presented according to health score (highest to lowest) with equal scored ordered by time to result (shortest to longest). In embodiments, the laboratory evaluation information may be tiered according to a health score—e.g., 100-95, 95-85, 85-75, etc. Within each tier, the laboratory evaluation information may be ordered by time to result. In further embodiments, laboratory evaluation information may be presented according to time to result with health score a secondary consideration. In further embodiments, all laboratories exceeding a minimum health score may be presented according to time to result. Further options may also be employed according to a user's needs.

Accordingly, the farm order evaluation method 520, as executed by the samples module 311, may evaluate orders to determine an optimal (or best available) farm lab operation to process a testing sample. In embodiments, the samples module 311 may determine a ranked list of farm lab operations according to the above described criteria.

At 540, the regional scheduler may start and at 541 it may wait and receive a plurality of order evaluations to process. The plurality of order evaluations may be based on orders provided by one or more users throughout the region associated with the regional scheduler process executed by the samples module 311. On receiving all order evaluations at 542, the samples module 311 may check the quality of results to ensure that at least one farm may execute each order successfully. If at least one regional farm lab operation is available, at 543 the samples module 311 may obtain the full rank-ordered set of evaluated orders factoring in the time to result and likelihood of success (or scorecard) with the first order evaluation being the suggested farm the user should send their sample to for testing. The rank ordered list may be provided, at 546, to a user awaiting farm lab operation options at 509. If at 542 the samples module 311 determines too low of a likelihood that any of the evaluations may succeed with a specific testing order, the system may post the order to the global services server 303 at 544 for redirection at 545, e.g., by the farm re-routing module 307, for a global scheduling process at 560 to distribute to other regions to handle. The farm re-routing module 307 may then interface with samples modules 311 in operation on one or more other regional services servers 304 for evaluation. In embodiments, the system may have an evolving threshold as to what is too low for success based on historical performance of the region in question.

At 560 of FIG. 5, the global scheduling process, e.g., in operation on the farm re-routing module 307, starts and at 561, may wait for orders that require redirection to other regions posting to regions in closest proximity to the failed region. At 562, a samples module 311 in operation at a regional level may receive the redirected orders and process these via the farm order evaluation process 520.

At 580 of FIG. 5, the farm order process starts and is executed by a farm operations module 312. The farm operations module 312 may wait to receive orders to process. The farm operations module 312 may cause equipment and staff at the farm operations lab to anticipate and wait for the receipt of an order. Based on the test scheduling and order posting at 515, the farm operations module 312 may receive information about an ordered test for processing at 581. After, or in conjunction with, receipt of an order at 581, the farm operations module 312 may receive samples for processing at 582. On receiving samples at 582, the samples may be prepared, e.g., through the use of farm lab operations equipment by farm lab operations personnel. Lab operations personnel may receive instructions for sample preparation from the farm operations module 312 and via computing systems associated with the farm lab operations, e.g., farm user computers, 231/341. The lab personnel, at 583, and via use of the farm lab operation bioinstrumentation devices, may then process the samples on the farm instruments through to the point of executing relevant assays and/or other scientific tests, scientific functions, etc. in the order on the provided, prepared samples. Lab operations personnel may receive instructions for sample processing from the farm operations module 312 and via computing systems associated with the farm lab operations, e.g., farm user computers, 231/341. In embodiments, farm lab operations bioinstrumentation devices may interface and/or communicate directly with the farm operations module 312 to electronically receive instructions to carry out the required processing. Once processing completes at 584 the system may post the order results for the one or more sample processed at 585. Results may be collected and stored regionally, e.g., via the results module 310 in operation on the regional services server 304 and/or collected and stored on a global basis.

In embodiments, the results module 310 may provide the results to the original sample collection facility where the results may be associated with a patient identity and reported to the patient.

In further embodiments, the results module 310 may receive additional patient information (e.g., demographics, health status, reported symptoms, etc.) from the original sample collection facility, associated this additional patient information with the sample results, and report these the system monitoring subsystem 230 to monitor development of one or more health conditions.

Although one or more steps described herein are disclosed as occurring in a particular order for these specifically disclosed embodiments, the order of steps may occur in a variety of sequences. The various steps described herein may be combined with other steps, interlineated with the stated steps, and/or split into multiple steps. Similarly, elements have been described functionally and may be embodied as separate components or may be combined into components having multiple functions.

To further illustrate the features and functions of the systems, methods, and apparatuses described herein, specific examples are provided below in the context of applying the same to the detection of, and response to, a global pandemic. Although the examples described below primarily within the framework of this particular application of these features, the description herein is not so limiting, and may be applied in a variety of other applications as well, including those described above, such as to immediately detect and quickly respond to other, various localized and/or global catastrophic events.

Figure 6B:
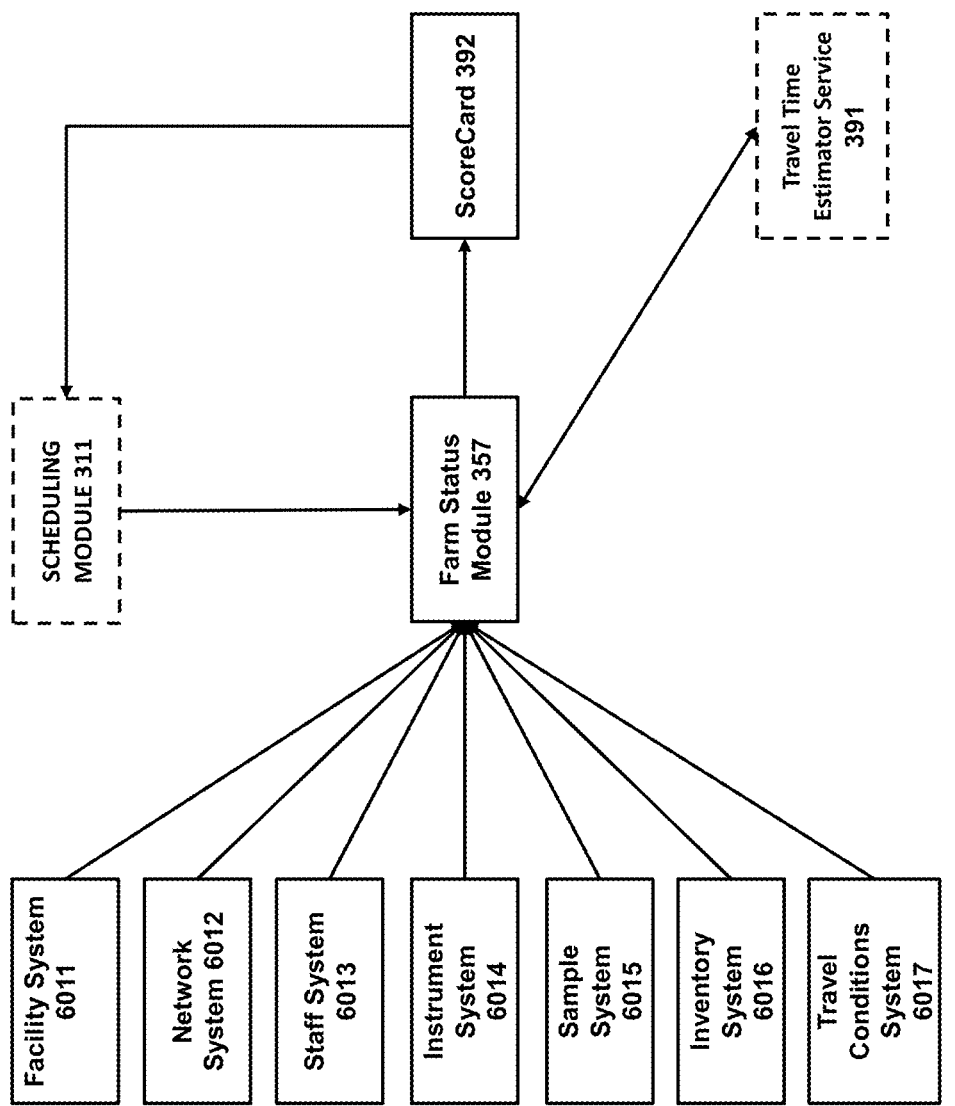
FIG. 6B illustrates operation of a scorecard determination method according to embodiments hereof.
Figure 6C:
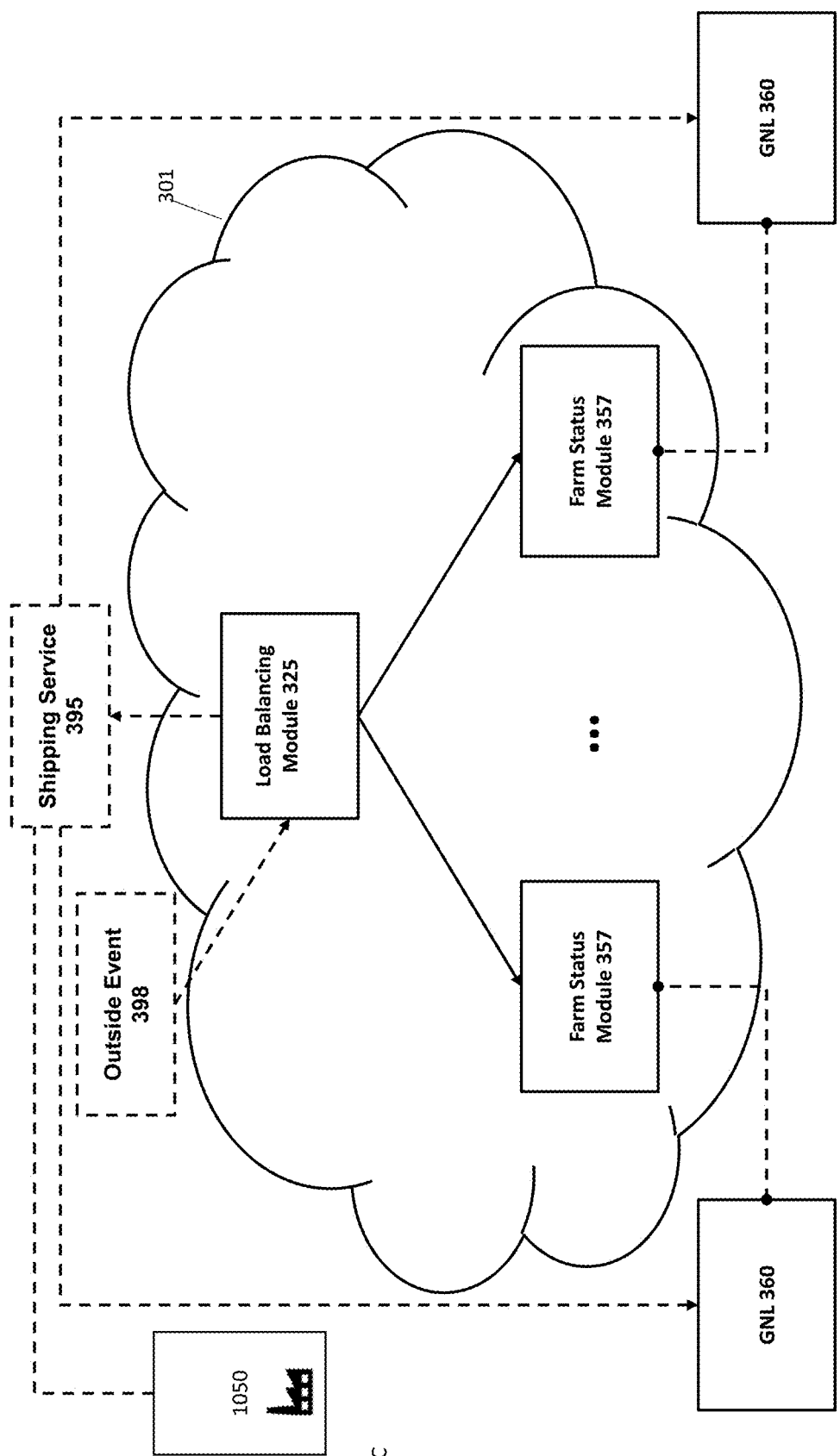
FIG. 6C illustrates operation of a load balancing module according to embodiments hereof.

FIGS. 6A-6C illustrated a scheduling and load-balancing procedure according to a score-card determination method. FIG. 6A illustrates a sample logistical structure coordinating communications and shipments between a sample collection facility 640 and a GNL 360, via the networking platform 301. FIG. 6B illustrates an example logic flow illustrating the creation and provision of a GNL scorecard to the scheduling module 311. FIG. 6C illustrates an inventory load balancing method based on the scorecard determination method described above.

FIG. 6A illustrates the networking platform 301 operating to facilitate communications between a sample collection facility 640 (e.g., any of sample collection facilities 202-208) and globally networked laboratories (GNLs) 360. The networking platform 301 operates to arrange shipments of samples between the sample collection facility 640 and a GNL 360 from among a GLN 351 (not shown). The scheduler module 311 operates in communication with the sample collection facility 640, for example through one or more test ordering user computers (see e.g., FIG. 3A, 340). The scheduler module 311 communicates with the farm status modules 357 associated with the GNLs 360. As discussed above, the farm status modules 357 may operate on the networking platform 301, on computing devices associated with the GNLs 360, and/or partially on each of these systems.

The scheduler module 311 communicates with the farm status modules 357 associated with the GNLs 360 to obtain scorecard information denoting related to aspects of the operational status of the GNL 360. The scheduler module 311 communicates information to the farm status modules 357 including the type of tests to be performed, the number of tests to be performed, and the location of the sample collection facility 640. The farm status modules 357 are configured to determine laboratory evaluation information, which may include a laboratory health score and an estimated time to result. These may be determined based on the operational status, staffing, inventory, etc. of the GNL 360 and the transit time between the requesting sample collection facility 640, an estimated time to result associated with the GNL 360. The farm status modules 357 are further configured to determine a laboratory health score. These are determined according to a GNL 360 scorecard, as described below with respect to FIG. 6B.

As illustrated in FIG. 6B, the farm status module 357 may receive information associated with at least a facility system 6011, a network system 6012, a staff system 6013, an instrument system 6014, a sample system 6015, an inventory system 6016, and a travel conditions system 6017. Each of these systems includes one or more components, the status of which may be provided with a percentage score, for example, from 0-100% (with 100% representing an optimal score). Each component may also be weighted, for example, from 1-100 (with larger numbers representing larger effects), based on the components' effect on overall operational status.

Table 1 provides an example scorecard, showing example scores and weights for a variety of system components. The Table 1 scorecard values are, in turn, determined according to specific parameters for a given GNL 360, for example, according to the parameters provided and shown in Table 2, as discussed further below. The systems, subsystems, and weights shown in Table 1 and Table 2 are by way of example only. Additional or different systems, subsystems, and weights may be used in a GNL 360 scorecard. The farm status module 357 may receive the system information directly from a computing device, sensor, circuit, or other automated device associated with the systems (e.g., devices that monitor hardware and physical plant systems), may receive the system information from other computing devices associated with the GNL 360 (e.g., devices that keep track of human resources and inventory), and/or may receive the system information from a human operator.

In embodiments, the scores for each system (e.g., facility 6011, network 6012, etc.) are determined according to a weighted average of the scores of each subsystem within the system. For example, as shown in Table 1, the weighted average of the Facility 6011 subsystem scores is 90%. The farm status module 357 is configured to determine the weighted average score for each system within the GNL 360.

The overall facility score is determined according to a weighted average of the individual system scores. In embodiments, the individual system scores are provided with weights inversely related to their value. Such a system amplifies the weights of lower scoring (poorer performing) systems. Accordingly, lower system scores are weighted higher and higher system scores are weighted lower.

In one example, the individual system scores are weighted according between 1 and 100 according to each individual system score. A perfect system score of 100% is given a weight of 1. System scores of 0%-99% are weighted according to their own value, according to the Max Weight−(Score*Max Weight). Accordingly, a high system score, e.g., 98% will have a weight of 2, i.e., a low weight. A low system score, e.g., 10%, would have a weight of 90, i.e., a high weight.

Thus, those GNL systems that are low scoring have a higher weight on the overall system scoring than those systems that are high scoring. This approach serves to amplify the signal of an underperforming system. For example, a GNL 360 that shows 100% in all systems except for staffing and is completely unstaffed, i.e., a 0%, would have an overall score of just 6%, indicating that the GNL 360 is in a poor state to provide sample processing results. If the system scores were weighted equally, the GNL 360 would show a score of 86%, indicating readiness to process sample results despite the complete lack of personnel.

In other examples, different methods of inverse weighting may be applied. For example, thresholds may be applied, wherein scores above are threshold are weighted according to an inverse function of their value while scores below a threshold are given a maximum weight. Such a system may be employed, for example, to ensure that any laboratory failing in one system is deemed to fail overall.

Table 1 further illustrates the Total Time to result, as determined by the farm status module 357. The Total Time to Result, in days, is determined according to the completion time in hours and local laboratory conditions. For example, in a GNL that works one 8 hour shift per day, the 22 hour processing time shown in Table 1 will take 2.8 days to complete. Increasing the number of hours per shift or shifts per day will decrease the Total Time to Result. The completion time is determined according to the transit time between the sample collection facility 640 to the GNL 360 combined with the sample processing time. The sample processing for a given number of samples may be determined, e.g., according to lab capability factors, such as the number of instruments, the number of staff, etc., e.g., as shown in Table 2. The transit time may be determined according to information provided by a travel time estimator service 391. The travel time estimator service 391 may be configured to determine a travel time between the GNL 360 and the sample collection facility 640, for example by common carrier, courier, ride-share service, direct delivery, etc. In embodiments, the travel time estimator service 391 may include third-party web- and/or app-based map/traffic software, such as Google Maps, Waze, Apple Maps, etc.

Table 2, as shown below, provides the raw inputs to permit the farm status module 357 to determine the values in the scorecard 392. A user, operator, and/or computing device associated with a GNL 360 may keep track, on a continuous and/or periodic basis, of the Table 2 values that provide the necessary inputs to farm status module 357 in determining the scorecard 392. The values in Table 2 keep track of overall capacity and available capacity of various resources, as well as estimated sample processing times.

Table 1 is produced according to scorecard rules that provide scores based on the resource availability as tracked in Table 2. In embodiments, the Table 1 scorecard values may be determined according to percent of overall capacity remaining. For example, as shown in the examples of Table 1 and Table 2, available storage capacity is at half of overall capacity, providing a 50% score.

The Farm Status Module 357 is further configured to provide a scorecard 392 including all or some of the information shown Tables 1 and 2. The systems, subsystem, weights, and scores depicted in these tables provide non-limiting exemplary embodiments and are provided herein merely for illustrative purposes only. The Farm Status Module 357 may provide a scorecard 392 having at least the Health Score information and the Time to Result information (collectively, laboratory evaluation information) to the scheduling module 311. In embodiments, the scheduling module 311 may automatically schedule sample shipment from the sample collection facility 640 to the GNL 360 according to the Health Score information and the Time to Result information. In further embodiments, the scheduling module 311 may provide the scorecards 392 of multiple laboratories to a user, with or without recommendations, and permit the user to select a GNL 360 for sample processing. In embodiments, the farm status module 357 and the scheduling module 311 may cooperate to facilitate providing all of the information of Tables 1 and 2 to a user to enhance the user's decision making. Referring now to FIG. 5, the results of the scorecard determination by the scheduling module 311 may be provided to a user, e.g., at 546.

TABLE 1

| | LOAD BALANCING SCORECARD - 392 | | |
|---|---|---|---|
| | Least-effect Weighting | 1 | |
| | Most-effect Weighting | 100 | |
| System | Subsystem | Weight | Score |
| Facility - 6011 | Power | 50 | 100% |
| | Backup Generator | 50 | 100% |
| | HVAC | 50 | 100% |
| | Bulk Storage Capacity | 50 | 50% |
| | Refrigeration Capacity | 50 | 100% |
| | Water | 1 | 100% |
| | Lights | 1 | 100% |
| Network - 6012 | Internet | 50 | 60% |
| | Intranet | 50 | 100% |
| | Ethernet Jacks | 50 | 100% |
| | Wi-Fi Access Points | 50 | 100% |
| | Internal Computers | 50 | 100% |
| | Internal Data Storage | 50 | 80% |
| | Cloud Provider | 50 | 100% |
| Staff - 6013 | Available Operators | 50 | 100% |
| Instrument - 6014 | Testing Potential | 50 | 100% |
| | Overcommitted | 1 | 0.0% |
| Sample - 6015 | Storage Capacity | 50 | 80% |
| | Active Capacity | 50 | 0% |
| Inventory - 6016 | Storage Capacity | 50 | 50% |
| | Active Capacity | 50 | 0% |
| | Pipette Tips Size 1 | 50 | 25% |
| | Pipette Tips Size n | 50 | 60% |
| | Labware Type 1 | 50 | 20% |
| | Labware Type n | 50 | 2% |
| | Assay 1 Availability | 50 | 99.78% |
| | Assay 'n' Availability | 50 | 99.78% |

TABLE 1-continued

| | | | |
|---|---|---|---|
| Local Travel Conditions - 6017 | Weather | 50 | 100% |
| | Local Stability | 50 | 100% |
| | Clear of Construction | 50 | 100% |
| Health Score | Facility Score | 10 | 90% |
| | Network Score | 9 | 91% |
| | Staff Score | 1 | 100% |
| | Instrument Score | 2 | 98% |
| | Sample Score | 60 | 40% |
| | Inventory Score | 55 | 45% |
| | Travel Conditions Score | 1 | 100% |
| | Overall Score | | 50% |
| Time to Result | Time to Deliver Samples | | 8.0 hrs |
| | Completion Time | | 22.0 hrs |
| | Total Time to Result | | 2.8 days |

TABLE 2

| System | Subsystem | Capacity | Available | Units |
|---|---|---|---|---|
| Facility | Power | 10 | 10 | |
| | Backup Generator | 500 | 500 | hrs |
| | HVAC | 100 | 100 | |
| | Water | 1 | 1 | binary |
| | Lights | 1 | 1 | binary |
| | Room Temp Storage | 10000 | 5000 | |
| | 4° C. Refrigerator | 1000 | 1000 | |
| | −20° C. Refrigerator | 500 | 500 | |
| | −80° C. Refrigerator | 100 | 100 | |
| | Total Refrigeration | 1600 | 1600 | |
| Network | Internet | 5 | 3 | providers |
| | Intranet | 1 | 1 | binary |
| | Ethernet Jacks | 20 | 20 | |
| | Wi-Fi Access Points | 10 | 10 | |
| | Internal Computers | 8 | 8 | |
| | Internal Data Storage | 1E + 12 | 8E + 11 | bytes |
| | Cloud Provider | 1 | 1 | |
| Staff | Operators | 3 | 3 | |
| | Support | 2 | 2 | |
| | Available for Testing | 3 | 3 | |
| | Time to Prepare Samples | | 8.0 | Hours |
| | Time to Process Samples | | 6.0 | Hours |
| Instrument | P5 1 Plates | 5 | 5 | |
| | P5 2 Plates | 5 | 5 | |
| | P5 3 Plates | 5 | 5 | |
| | P5 4 Plates | 5 | 5 | |
| | P5 5 Plates | 5 | 5 | |
| | P5 6 Plates | 5 | 5 | |
| | P5 7 Plates | 5 | 5 | |
| | P5 8 Plates | 5 | 5 | |
| | P5 9 Plates | 5 | 5 | |
| | P5 10 Plates | 5 | 5 | |
| | Total Plate Capacity | 50 | 50 | |
| Sample | Storage | 500000 | 100000 | kits |
| | Active | 1850 | 1850 | kits |
| | In Queue | 500000 | 0 | kits |
| Inventory | Storage (Kits) | 1000000 | 500000 | kits |
| | Active (Kits) | 50 | 50 | kits |
| | In Queue (Kits) | 1000000 | 0 | kits |
| | Pipette Tips Size 1 | 1000000 | 250000 | |
| | Pipette Tips Size n | 500000 | 300000 | |
| | Labware 1 | 1000000 | 200000 | |
| | Labware n | 1000000 | 20000 | |
| | Assay 1 | 250000 | 249450 | |
| | Assay n | 250000 | 249450 | |

After the scorecard determination process by the farm status module 357 and the scheduler module 311, the results may be provided to a regional scheduler process (see, e.g., FIG. 5, 541) or, for example, as options to an operator at the sample collection site 640 (see, e.g., FIG. 5, 546). An operator at the sample collection site 640, e.g., via a test ordering computer, may select a GNL 360 for sample processing. After selection, the scheduler module 311 notifies operators at the GNL 360 that samples are incoming.

The scheduler 311 further operates to facilitate sample shipping. For example, the scheduler 311 may operate to cause shipping labels to be printed and a pick-up to be scheduled, e.g., via common carrier, at the sample collection facility 640. In further embodiments, the scheduler 311 may contact a ride-share service, courier, and/or other direct delivery carrier to transport the samples to the GNL 360. After processing of the samples at the GNL 360, the results may be provided to the sample collection facility 640 and to all other suitable aspects of the global bio-surveillance and response system, e.g., the results module 310.

FIG. 6C illustrates an example logical structure of a load balancing system including the load balancing module 325 of the networking platform 301. The load balancing module 325 communicates with the farm status modules 357 to facilitate load balancing between the GNLs 360 of the GLN 351 (not shown). Some or all of the functionality described below with respect to the load balancing module 325 may, in embodiments, be performed by the inventory module 324, as discussed above. Accordingly, the described method may be performed by the load balancing module 325 and/or by the load balancing module 325 in conjunction with the inventory module 324.

In embodiments, the load balancing module 325 may periodically query each farm status module 357 to receive the scorecard 392 of the associated GNL 360. The load balancing module 325 may receive the scorecard 392 including inventory information related to the GNL 360. The scorecards 392 may reveal the status of various inventory (sample kits, consumables, swabs, reagents, etc.) across the GNL 351. Based on the current inventory, the anticipated future inventory (i.e., according to tests scheduled by the scheduler module 311), and the current sample processing loads associated with each GNL 360, the load balancing module 325 may operate to ensure adequate inventory supplies at the various GNL 360.

For example, the scorecard 392 of a first GNL 360 along with information about scheduled samples for processing at the GNL 360 may indicate that the first GNL 360 has an oversupply of inventory. Concurrently, similar information from a second GNL 360 may indicate that the second GNL 360 has an undersupply of inventory. Accordingly, the load balancing module 325 may cause the engagement of a shipping service 395 to transfer inventory from the first GNL 360 to the second GNL 360. In further embodiments, the load balancing module 325 may cause the shipping service 395 to transfer inventory from a manufacturing facility 1050 (as described in greater detail below with respect to FIG. 8) or an inventory warehouse to the second GNL 360 (or any other GNL requiring additional inventory.

In embodiments, the load balancing module 325 may further operate to anticipate potential spikes in inventory requirements and allocate resources accordingly. For example, the occurrence of an outside event 398, such as the detection or determination of a health condition, as described herein, may trigger the global bio-surveillance and response system to enter a surge mode, requiring additional testing capacity in one or more regions. In response to such an outside event, the load balancing module 325 may engage the shipping service 395 to transfer inventory and/or supplies from a first GNL 360 outside of a surge region and/or from a manufacturing facility 1050 or warehouse to a second GNL 360 in close proximity to a surge region. Such a transfer may occur before a significant amount of sample processing is required at the second GNL 360, in anticipation of such requests in the future.

Although the examples provided in conjunction with FIGS. 6A-6C illustrate non-limiting, exemplary load-balancing embodiments directed toward load balancing of sample testing specifically, similar load-balance principles can be applied to additional resources as well, for example, distribution of instruments (e.g., POC devices), equipment, consumables, personnel, etc. Moreover, additional sample-testing-based load-balancing methodologies can be employed as well. For example, scheduling module 311 can steer, direct, re-route, etc. samples to one or more particular sample testing locations based on data (such as, for example, de-identified data described in greater detail below) including, by not limited to, rates of changes in testing frequencies, app-based usage rates (e.g., increased activity of users utilizing app-based software to perform self-testing), third-party search results (e.g., increase in users' web-based searches for a particular symptom, pathogen, etc.), aggregated data treads of one or more populations, such as, for example, morbidity rates, mortality rates, hospitalization rates, respirator requirement rates, symptom trends (e.g., average fever of positive individuals), etc. In further embodiments, one or more of these can be used for human resource planning, such as developing staffing schedules, increasing personnel headcount at a particular location or locations, etc.

Figure 7:
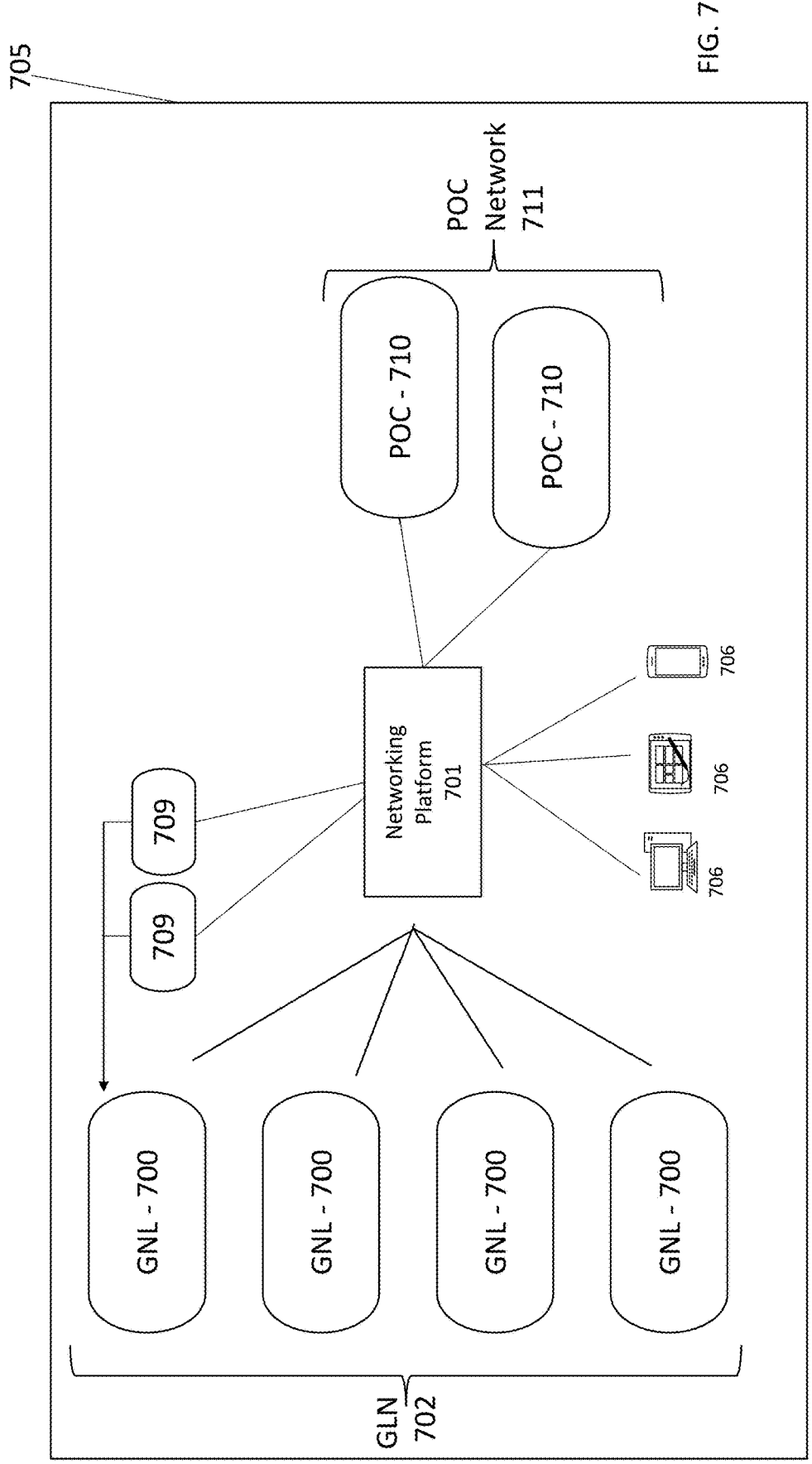
FIG. 7 illustrates a global laboratory network consistent with embodiments hereof.

FIG. 7 illustrates a Global Laboratory Network, (GLN) 702. The GLN 702 may include a network of approximately 1,000 globally networked laboratories (GNL) 700 worldwide (although greater or fewer than 1,000 are contemplated as well) connected through a networking platform 701 similar to that previously described with respect to FIGS. 1, 2, and 3A/3B (e.g., 101, 201, 301). In embodiments, the GNLs 700 may be part of the sample processing subsystem (see, e.g., FIG. 1A, 103), part of the sample collection and test ordering subsystem 101, and/or part of the independent sample testing subsystem 104. Various constituent components of the networking platform are described below with respect to their descriptions as provided in FIGS. 1, 2, and 3A/3B.

Each of the GNLs 700 may be designed to provide routine testing and assay development capabilities to support commercial life science research activities, including, for example, assay and vaccine development, testing capabilities, stockpiling of supplies, consumables, and equipment, etc. In embodiments, during this routine testing, the laboratories may be described as being in "Surveillance Mode," or "Sentinel Mode" in which the testing performed is to screen, for example, for known, unknown, or emerging pathogens. In examples, this testing may be part of the sample collection and test ordering subsystem (see, e.g., FIG. 1A, 101), comprising, for example, one or more instruments from among the one or more distributed sentinel devices (see, e.g., FIG. 2, 241). In certain examples, the one or more distributed sentinel devices can include, for example, point of care ("POC") devices that require a separate instrument and/or analyzers to read the tests, such as, for example, cartridge readers (e.g., swab-based cartridges, serological (e.g., blood)-based cartridges, etc.), or they can include instrument-less devices, such as, for example, lateral flow test devices. Other examples of these devices can include strip testers, swap tests, dip sticks, flow cells, etc. In other embodiments, the one or more distributed sentinel devices can include a mobile device, such as cellular phone with or without additional software (e.g., mobile-based apps) and/or hardware (e.g., breathalyzer attachment hardware to interface with the mobile device via a physical connection, and/or wireless connection (e.g., Bluetooth, NFC, Wi-Fi, etc.)). In this example, the mobile devices themselves (e.g., either with or without the additional software and/or hardware) can be the sentinel devices within the global bio-surveillance and response system 705. Each GNL 700 is adapted to seamlessly and rapidly convert from Surveillance Mode to "Surge Mode," for which the GNL 700 may have the capability to handle a rapid surge (as well as a shift) in its functions (e.g., testing, assay development, etc.) based on one or more triggering events (such as, for example, a disease outbreak, a radiological and/or nuclear event, a bio/chemical-defense-related event, etc.). Because the GNLs 700 may be widely geographically distributed, those GNLs 700 proximate to the outbreak may help to contain, or completely quell, their initial spread. For example, as discussed above, user accounts may be dispersed across the globe. See, e.g., FIG. 4, 440, 443, 446, 449, 452. Under certain conditions, an outbreak may quickly spread beyond its point of origin. Under those circumstances, one or more of the pre-existing GNLs 700 may be equipped to allow for the rapid scale up of testing to fight outbreaks (such as pandemics, epidemic, endemics, etc.). See, e.g., FIG. 1A, 103. Thus, through rapid scale up, the amount of human and economic damage may be sharply limited or curtailed.

In embodiments, the GLN 702 and its constituent GNLs 700 are part of a global bio-surveillance and response system 705 and are connected to each other and to other aspects of the global bio-surveillance and response system 705, e.g., via the networking platform 701, as described herein. The global bio-surveillance and response system 705 may include any or all of the features and functionality of the global bio-surveillance and response systems 100, 200, and 300.

The global bio-surveillance and response system 705 may include various features to provide for the advantages described above with respect to the GLN. For example, in certain, embodiments, the global bio-surveillance and response system 705, may provide continuous monitoring of populations for the presence of an unknown pathogen, for example, through the system monitoring subsystem 220 (see, e.g., FIG. 2, 220, FIG. 1A, 102, FIG. 3, 342).

Because early identification of a pathogen may be key to an effective response to a detected health condition, e.g., biological-, chemical-, and/or biochemical-related outbreak or catastrophe, the GLN 702 may be employed to perform routine epidemiological testing of samples for the presence of a health condition, for example, known respiratory pathogens such as influenza A and B, respiratory syncytial virus (RSV), adenovirus, and coronaviruses, among others. Testing for additional, non-respiratory pathogens may also be performed. During this routine testing (e.g., upper respiratory testing), in embodiments, the GLN 702 may provide additional testing to further examine samples. This may include, for example, retesting and/or additional testing of symptomatic patients that test negative across the test panels (e.g., these samples may indicate that a new pathogen is circulating) or positive results that may require additional information and/or testing to better understand and/or reconcile the patients' result and their symptoms. These samples may be sequenced by next-generation sequencers (e.g., high throughput instruments, etc.) pre-placed into GNLs 700 (or redistributed as needed), allowing rapid identification and response to new pathogens.

The system monitoring subsystem 220 is configured, as described above and with respect to system monitoring subsystems 102 and 342, to receive data from tests performed by the GNLs 700 during a surveillance mode. Coordination and data sharing between multiple GNLs 700 at the mission control level may provide operators with heretofore unavailable insights into an emerging outbreak situation. The rapid receipt of data and information from multiple GNLs 700 may provide a larger picture of an outbreak situation and indicate that a newly identified pathogen, for example, is not occurring as only an isolated case. For example, in a single laboratory setting, one or two patients carrying a newly identified pathogen may be seen as a small localized occurrence. When data are available across multiple GNLs 700 at a central location, e.g., a mission control subsystem associated with the global bio-surveillance and response system 705, the potential severity of a rapidly emerging situation may be better assessed.

If a new health condition is identified, the GLN 702 may be equipped to quickly transition into Surge Mode because the laboratories have the pre-existing capability to handle the increase in testing and other demands, for example, through the sample processing subsystem (see, e.g., FIG. 1A, 103).

As noted above, the GLN 702 has high-throughput testing capabilities. Using a pandemic as an example again specifically, the ability to provide adequate testing capabilities during a pandemic (or imminent pandemic) may be often be problematic, particularly, with the existence of asymptomatic cases. For example, the lack of testing may hamper or dampen efforts to limit the spread of the disease, for researchers to correctly understand mortality rates, and to take steps to safely re-open the global and local economies. In embodiments, the global bio-surveillance and response system 705 may include the GNL 702, a network of GLNs 700 that may provide high-throughput mass testing capability, for direct detection and diagnosis of those individuals affected with a pathogen, as well as testing to determine who has antibodies or other immunities to the pathogen (such as serology-based testing) either through having had the virus or through immunization, and/or it may include nucleic acid-based detection (with or without amplification), or any combinations thereof. Using the example, above, if the GLN 702 includes 1,000 locations, each with 10 testing instruments per lab, nearly 15 million samples may be tested per day, and nearly 105 million samples tested each week. In embodiments, under surge conditions, (e.g., Surge Mode), sample pooling, as discussed below, may also be employed, by pooling, for example, 10 samples together (although greater or fewer samples may be pooled together as well). Under this example, if a pooled sample tests positive, then the individual samples making up the pooled sample may be retested to determine which of the individual samples are positive. Pooling samples in this manner may increase sample testing throughput even further (e.g., up to ten-fold, using the 10-sample example described above. In embodiments, the GLN 702 may be further designed in a manner to provide wide geographical distribution, by establishing large numbers of GNLs 700 in a widespread worldwide distribution. For example, the GNLs 700 of the GLN 702 may be established to pre-position labs across the globe to ensure that wherever there is a disease outbreak (using the pandemic example specifically), a highly capable lab is proximate to the outbreak. Continuing with this example, samples from affected patients may be rapidly transported to the nearest lab for testing. Further examples and discussion of sample pooling may be found in PCT Application Nos. PCT/US2021/030294, filed on Apr. 30, 2021, PCT/US2021/030297, filed on Apr. 30, 2021, and PCT/US2021/030299, filed on Apr. 30, 2021, and U.S. Provisional Patent Application No. 63/214,291, filed Jun. 14, 2021, each of which is incorporated herein by reference.

In embodiments, one of more GNLs 700 among the GLN 702 may be adapted to conduct commercial sample testing on a daily basis (or other frequency as well, hourly, semi-daily, etc.), but still retain to the flexibility to quickly convert to surge testing as needed, for example, in public health emergencies, disease outbreaks, etc. In further embodiments, the global bio-surveillance and response system 705 may provide real-time and/or near real-time global results via the networking platform 701, for example a cloud platform (see, e.g., FIG. 1A, 105). Using a pandemic as an example again, with any disease outbreak, time may be of the essence in detecting the pathogen, sequencing its DNA/RNA, and creating a test for the pathogen. Additionally, if mass sample testing is required, local, state, federal governments, etc. and populations may wish to understand where the outbreak is occurring in as close to real-time as possible. The networking platform 701 of the global bio-surveillance and response system 705 may provide an interconnected network with internet connections or any other electronically based communication systems. For example, the instruments connected via the networking platform 701 may be connected through cloud-enabled software—for example as disclosed in U.S. Application No. PCT/US2019/042274, filed on Jul. 17, 2019, U.S. Application No. 62/964,435, filed on Jan. 22, 2020 and PCT/US2021/014379, filed Jan. 21, 2021, all of which are incorporated herein by reference. This software is capable of establishing a distributed highly capable cloud-based system that may provide data on sample testing in real time. In other examples, the software may not be cloud-based.

In embodiments, the networking platform 701 may be configured to create experiments at key sites that are then pushed out to instruments running within the GLN 700, schedule experiments, and automatically load balance experiments across the GLN 700, real-time upload data from instruments to the cloud and provide the ability for analysts at widely distributed locations to analyze data. The networking platform 701 may further be configured to provide the ability to run algorithms against routine data coming from the instruments to look for the presence of health conditions that may suggest the presence of an unknown pathogen. Moreover, the networking platform 701 may facilitate the tracking of samples from their beginning to end points, along with any intermediate points there between, such as, for example, by scanning a barcode (2D and/or QR code) each time the sample as transported to a new location and/or is deposited with and/or received by each individual and/or entity involved in the transportation, testing, and result reporting of the samples.

In still further embodiments, the global bio-surveillance and response system 705 may include the capability to rapidly identify and sequence emerging pathogens. An example here may include one or more GNLs 700 operating as sentinel sites, for example, operating as a sample collection and test ordering subsystem (see, e.g., FIG. 1A, 101) and/or an independent sample testing subsystem (see, e.g., FIG. 1A, 104), each including the ability to rapidly identify and sequence emerging pathogens (e.g., each may include nucleic acid sequencing capabilities). Utilization of this sequencing capability may be critical if an unknown pathogen is suspected to be present, which may further allow for the rapid identification of the pathogen and movement to initial assays. Various assays may be then utilized for this identification—for example, those assays disclosed in U.S. Application No. PCT/US20/30754, filed on Apr. 30, 2020 (i.e., nucleotide-sequenced assays) and incorporated by reference herein—to quickly run assays and/or other experiments on instruments, such as the P5 instruments.

In still further embodiments, again using the pandemic examples, the GNLs 700 of the GLN 702 may further have the capability to rapidly develop new tests for emerging pathogens. In embodiments, the GNLs 700 may be divided into various tiers (e.g., Tier-1, Tier-2, Tier-3, etc., as described in greater detail below and illustrated in FIG. 2A. Tier-1 labs (see, e.g., FIG. 2A, 232), for example, may include rapid assay development capabilities, thus allowing those labs to quickly develop immunoassays that will be capable of direct detection of the pathogen as well as antibody tests that will be capable of determining if individuals have antibodies to the pathogen either through exposure to the pathogen or through immunization.

In embodiments, the GNLs 700 may include a standardized set of equipment (e.g., state-of-the-art equipment), operating procedures, as well as facilities templates. By standardizing and harmonizing these attributes across one or more of the labs within the GLN 700, consistency throughout the network may be achieved (e.g., results from any one lab will match the results from other labs in the network), which may lead to efficiencies in assay validation. Further, scheduling work at the GNLs 700 may be simplified, as it may not be necessary to query whether a specific lab has the appropriate equipment and personnel to perform a specific test. Standardization may also provide additional benefits under surge conditions, e.g., requiring the training of large numbers of staff members. Through standardization, uniform training programs, videos, material, curricula, etc. may be established and distributed among labs within the network. This standardization may also enable economies of scale such as in equipment acquisition, manufacturing, and facilities construction. Moreover, the GLN 700 may establish and deploy best practices for sample handling, sample processing, pathogen detection, assay development, and quality standards, among many other areas, to further streamline procedures and increase efficiencies among labs.

In still further embodiments, the GNLs 700 may include the capability for sustained surge testing. For example, the GNLs 700 may have the capability of maintaining surge-level testing over long periods of time (e.g., a minimum of 6 months, although longer periods are contemplated as well). To sustain this capability under surge conditions, each lab may include its own inventory of necessary disposable materials, including, e.g., swabs, sample collection containers, reagents, and plasticware, etc. Additionally, the GLN 702 may include stockpiles of supplies at depot facilities strategically placed throughout the globe (e.g., United States, the European Union, Asia, etc., although other locations are contemplated as well). The inventory at individual labs may support surge testing throughout and until additional supplies arrive from one or more of these depots. By stocking supplies at depot locations, the GLN 702 may direct supplies outbound to labs in areas that are most affected (as opposed to relying on individual labs with supply surpluses to ship to others with supply deficiencies). In embodiments, the one or more supply depots may provide enough inventory to cover surge testing until manufacturing may ramp up to fill the demand pipeline.

The GNLs 702 that comprise the GLN 700 may be divided into two or more tiers (see, e.g., sample processing subsystem, FIG. 2A, 230). Using the example of 1,000 global labs above, for example, labs may be designated as Tier-1 (see, e.g., FIG. 2A, 232) or Tier-2 (see, e.g., FIG. 2A, 233) (although additional tiers are contemplated as well (e.g., Tier-3, see, e.g., FIG. 2A, 234). In one embodiment, roughly 10% or 100 of the overall labs may be classified as Tier 1 labs and roughly 90% 900 labs classified as Tier 2 labs. In other examples, these tiers may be divided in different proportions (e.g., 20%/80%, 50%/50%, 5%/95%, etc.). Continuing with this example, the Tier-2 labs may include scientific equipment and/or bioinstrumentation providing high-throughput testing capabilities (such as, for example, by making use of one or more P5 instruments, either as standalone units or in farms) for both routine and surge testing scenarios. Tier-1 labs may include the same testing capabilities as Tier 2 labs, but may include additional scientific equipment and/or bioinstrumentation providing capabilities in rapid assay development. These capabilities may allow Tier 1 labs to quickly develop new assays in response to new disease outbreaks and to then push these new assays out to the Tier 2 labs where most testing will take place. Tier 1 labs may also include certain capabilities to support the commercial mission of private or public corporations, institutions, etc., by including, for example, training and demonstration suites for customer training on assays and equipment and pre-sales demonstration of equipment and assay products utilized by the labs, and made commercially available for purchase or rental. In embodiments, Tier-3 labs can include pop-up and/or mobile testing sites. For example, a Tier-3 lab can include one or more instruments for processing test results, such as assays, for example in a high throughput and/or ultrahigh throughput manner. A Tier-3 lab may include, for example, one or more semi-automated and/or fully automated instruments (such as, for example, the P5 instruments descried herein), that can be set up at a temporary location (e.g., parking lots, sports stadiums, etc.) and subsequently torn down and relocated to another location. In this regard, Tier-3 labs can operate as mobile and/or portable stripped down versions of Tier-2 labs (e.g., fewer total instruments, less throughput capacity, etc.) to provide a rapid response to increase testing needs for remote locations or locations that require additional testing capacity to be provided with a relatively short turnaround time. The instruments in one or more of these labs (e.g., p5 instruments) may be semi- or fully automated. In this regard, individuals, even those with little-to-no training on the instrument, will be able to quickly simply and quickly carry out the necessary functions to perform these tests either through automation, or through simply step-by-step instructions provided (for example in the software running on the instrument itself), etc. Accordingly, in embodiments, the labs are designed to permit users to acquire high quality results with minimal training, irrespective of the user's skill level or capabilities.

In these examples, Tier-1 labs may be the largest, best equipped, and most versatile labs, providing not only high and ultrahigh throughput testing capabilities during surge and non-surge conditions, but also assay development, sequencing capability for rapid sequencing of the DNA/RNA of unknown pathogens, probe/primer synthesis capability for rapid stand-up of plate-based assays (e.g., 96-well ECL plates) and Polymerase Chain reaction (PCR) assays, protein synthesis capabilities to rapidly generate reagents to support immunoassays, and training and demonstration capabilities for equipment and assays.

Tier-2 labs may include scientific equipment and/or bioinstrumentation providing a subset of the capabilities of Tier-1, in particular with a focus on high and ultrahigh throughput testing. In certain embodiments, Tier-2 labs can have the same number or fewer instruments that Tier-1 labs. Moreover, Tier-3 labs may provide the same services as Tier-2 labs but in a more limited fashion (e.g., fewer instruments, lower overall sample testing throughput, etc.), but with the added benefit of being highly mobile and versatile to provide testing services to remote locations and locations that other locations that may require immediate supplemental testing services, for examples, during a surge condition within a confined geographical location.

In further non-limiting, illustrative embodiments, Tier-1 labs may include scientific equipment and/or bioinstrumentation providing high-throughput sample testing capability, sequencing capability for rapid sequencing of the DNA/RNA of unknown pathogens, probe/primer synthesis capability for rapid stand-up of plate-based assays (e.g., 96-well ECL plates) and Polymerase Chain reaction (PCR) assays, protein synthesis capabilities to rapidly generate reagents to support immunoassays, rapid assay development capability; and training and demonstration capabilities for equipment and assays.

In embodiments, the scientific equipment and/or bioinstrumentation providing the capabilities described above may be configured in either a research mode or a clinical mode. In a research mode, the instruments may provide a full suite of features and optionality. Such a mode may be appropriate, for example, for Tier-1 labs and/or Tier-2 and Tier-3 labs in phase 0 sentinel conditions. In a clinical mode, the instruments may provide a limited suite of features and optionality, for example, limited to features and options associated with a specific battery of tests and or sample processing methods. Such a mode may be appropriate, for example, for Tier-2 and Tier-3 labs in an elevated phase surge condition to ensure that the instruments are In further non-limiting, illustrative embodiments, Tier-2 labs may include scientific equipment and/or bioinstrumentation providing high-throughput sample testing capability and sequencing capability for rapid sequencing of the DNA/RNA of unknown pathogens.

In further examples, each of the tiered labs among the GNLs 700 may have a broader or narrower set of equipment and services offered as contemplated in the particular example described above. In addition to these labs, one or more depot facilities (e.g., three, but more or fewer are contemplated as well) may be used to stockpile equipment, consumables, etc., such as swabs, sample tubes, and other items needed for testing. Using the example of three, each may be strategically placed geographically (such as for example one in the United States, one in the European Union, and one in Asia, although other locations are contemplated as well). Under surge conditions, supplies may be able to be shipped out via air freight (or any other means of transportation) and distributed to one or more of those labs.

In further embodiments, one or more of the Tier-1, Tier-2, and/or Tier-3 labs may be utilized to stockpile surpluses as well (e.g., instruments, consumables, equipment, swabs, etc.). In still further embodiments, one more of these labs may include the ability to manufacture additional instruments, consumables, and/or equipment. In a non-limiting example, each Tier-1 lab (and/or Tier-2, Tier-3, etc.) could have the ability to manufacture reagents, test kits, plastics and other materials for microtiter plates (e.g., 6-, 12-, 24-, 48-, 96-, 384- or 1536-well assay plates), etc. In this regard, the labs with these stockpiling and/or manufacturing capabilities may either be partially or fully self-sustaining, such that they would no longer need to rely on external stockpiling depots or other manufacturing facilities (e.g., one or more facilities located within the manufacturing facility network 802) to continue performing their testing functions throughout surge (or other) conditions.

Using the pandemic example again, the GNLs 700 may be dispersed around the globe, pre-placed and operational in advance of a disease outbreak. With this configuration, samples may be collected locally, and thus, proximate to a local lab. This may limit the required amount of transit time for samples and potential for sample degradation due to long transit times. The geographical placement of the labs may be determined from one or more criteria, for example, including one or more of proximity to population centers such as large towns and cities, and proximity to transportation systems. For example, labs may be placed in proximity to modern and well-maintained road networks to aid in the receipt of samples and supplies and/or may be placed in proximity to airports with at least 4,000 ft. runways (or longer or shorter runways necessary to accommodate appropriate aircraft) and instrument approaches to aid in the receipt of samples and supplies. Longer or shorter runways may be used to determine this criterion as well, or other airport metric (e.g., number of outbound flights per day, etc.). Further criteria employed for determination of GNL 700 placement may include adequacy of public utility systems including power, water, and fuel for backup generators (may be based on objective metrics such as amount of infrastructure, capacities, quantity of hardware (e.g., generators, transformers, etc.)), stable and high-speed internet systems to support the IT infrastructure of the labs (may be based on objective metrics, such as, for example, quantity of hardware (e.g., switches, routers, etc.), speed of connections, etc.).

Continuing with these examples, Tier 1 GNLs 700 may typically be placed one per country or one per major metropolitan area (although other numbers of labs per country or metropolitan area are contemplated as well). Tier 2 GNLs 700 may be more widely distributed and placed based on algorithms that consider the above criteria (or additional criteria and/or factors as well), either alone, or in combination with population density.

Continuing with the pandemic example above, GNLs 700 may include various hardware and equipment to provide routine sample testing, surge sample testing, monitoring for unknown pathogens, and rapid assay development, among other objectives. Some non-limiting, illustrative examples of these are shown in Table 3, below.

TABLE 3

| Lab Tier | Function | Subfunction | Equipment | Relevant Specifications and Notes |
|---|---|---|---|---|
| Tier 1 | Training and Demonstration | Training and Demonstration | Q 60 Instrument<br>SQ 120 Instrument<br>S 600 Instrument<br>Parsec R 5000 (P5) Instrument | |
| | Protein Production | Molecular Biology Lab for Plasmid Creation and Scale Up | Pipettes, bacterial incubators, agarose gel units, PCR instruments | Designated lab area |
| | | Rapid Protein Production | BSCs for tissue culture<br>Incubators for mammalian tissue culture<br>Centrifuge<br>AKTA Pure Systems<br>Chromatography Refrigerators<br>$-80°$ C. Refrigerators<br>Pipettes, gel systems, Nanodrop Spec, plate reader | |
| | | Protein and Antibody Conjugation and Characterization | Analytical HPLC<br>DLS Plate Reader<br>Reichert4SPR for antibody affinity measurements<br>Conjugation Centrifuges | |
| | General Storage | General Reagent Storage | Walk in $-20/4°$ C. Refrigerators (25' × 25' 4° C. and 15' × 25' $-20°$ C.) | |
| | General Storage | General Kit Storage | General Warehouse | |
| Tier 1 and Tier 2 | Sample Testing | Sequencing of Unknown Pathogens | MiSeq | Requires two designed lab areas for instrument and sample prep |
| | | DNA/RNA Synthesis for assays (nucleic acid) | CodexDNA BioXp 3200 or Biolytic ABI 3900 | Requires dedicated laboratory area |
| | | Sample Storage | $-80°$ C. Freezer | 30,000 samples × 8 freezers = 240,000 samples |
| | | Sample Decapping | Decapper 550 | Need a minimum capability to reformat 14,800 tubes to plates in 24-hour cycles to keep up with 10 P5 systems. Assume 30 seconds to decap 10 tubes. |
| | | Sample Formatting- Tubes to 96 well plates | Tecan Fluent, Hamilton VANTAGE, or Pipetting System | Need a minimum capability to reformat 14,800 samples from tubes to plates in 24-hour cycles to keep up with 10 P5 systems. Assume six minutes per 96 well plate for reformatting. |
| | | Sample Testing | Parsec R 5000 | Total of 14,800 samples per day in surge conditions |
| | General Storage | General Reagent Storage | Walk in $-20/4°$ C. Refrigerators (25' × 25' 4° C. and 15' × 25' $-20°$ C.) | |
| | General Storage | General Kit Storage | General Warehouse | |

In embodiments, the GNLs 700 may include high throughput instruments, such as P5 instruments to allow for ultrahigh throughput testing. Using this instrument as an example, the P5 may be used as a general-purpose automated system that may provide sample-to-answer processing for biological, chemical, and/or biochemical testing and analysis, such as electrochemiluminescence (ECL) immunoassays (although assays and/or other tests are contemplated as well). Each GNL 700 in the GLN 702 may include, for example, at least ten P5 instruments, although other numbers of these instruments are contemplated as well. Using ten instruments as an example, each lab may test up to approximately 15,000 samples per day or up to 105,000 sample per week in a fully automated manner, assuming 96-well test plates (although other types of consumables may be used as well, e.g., 384-well plates, etc.). A specific example is provided below in the Table 2, below.

TABLE 5

| Plates per run | Runs per day | Samples per plate | Number of instruments per lab | Total Number of Labs | Total Tests Per Day | Total Tests Per Week |
|---|---|---|---|---|---|---|
| 5 | 4 | 37 (duplicate) | 10 | 1,000 | 7.4M | 51.8M |
| 5 | 4 | 74 (singlicate) | 10 | 1,000 | 14.8M | 103.6M |

Additional advantages and/or key features of the P5 as used in the GLN 702 may include, for example, batch processing of up to five (5) 96-well assay plates at a time, high-throughput, using the specific example above, time to result for all 5 plates is between 6 and 7 hours depending on the assay protocol, completely automated system, which may allow lower-skilled personnel to be quickly trained to run large numbers of samples with in-process quality checks, results may be automatically uploaded to the networking platform 701 using software, to allow data from geographically distributed instruments to be observed in real time from any location with internet access. In other examples, the software does not necessarily need to be cloud-based, e.g., through the networking platform 701.

Continuing with the pandemic example above, the GNLs 700 may include the ability to test serum, plasma, urine, saliva, nasal swab samples present in swab sample containers, cerebrospinal fluid, cell supernatants, fecal samples, etc. For periods of non-surge conditions, for example, various equipment may be made available in the labs. For example, sample containers may be provided in advance to one or more customers. Those containers may include, for example, a barcoded tube or other sample collection device, order information, biohazard bags, a shipping label, appropriate cold shipping materials, etc. The labs may further include the capability of being compatible with various customer-specific sample containers as well. Further, the labs may include the capability of handing samples contained in cryotubes, 96-well plates, 386-well plates, and milliliter containers, etc.

In embodiments, under initial surge conditions during a pandemic, for example, samples may be swab based samples (although other types are contemplated as well) and assays may be focused on direct detection of a pathogen. As the outbreak proceeds, samples may include a mix of swab and blood samples (or other samples), as testing shifts to direct detection (e.g., determining whether the patient is currently infected) and/or antibody/serological testing (e.g., determining whether the patient has already recovered and/or if the immunization worked). To provide the highest sample testing throughput, sample collection containers may be standardized for various types of samples, such as nasal and blood samples (although others are contemplated as well).

As discussed above, the global bio-surveillance and response system 705 may further incorporate user devices 706. User devices 706 may include, for example, smart phones, tablets, computers, smart watches, and/or other consumer devices capable of running user software. In embodiments, using the pandemic example again, under surge conditions, the GNLs 700 may be equipped to efficiently collect samples and provide test results back to patients, e.g., via the user devices 706. This may be accomplished, for example, with an application-based approach to pairing samples to individuals and routing results back to the individuals when available. Applications, software, and/or apps may be made available on major mobile platforms and/or other operating systems, such as iOS, Android, Windows, Linux, etc. The user device applications, software, etc., as discussed below are adapted to configure a user device as a special purpose computer to carry out the functionality discussed below.

The user device 706 solution may include one or more of the following functionality and/or features. Users may have the ability to download the app or software prior to having a sample taken. Users may register themselves (and, family members, relatives, etc. as necessary) in the app, accept any legal or privacy notices (such as consent to have results submitted via the app), and set their preferred language, etc. The app or software may have features to accommodate multiple family (or other related) members if more than individual is sharing the computing device (e.g., mobile phone or other mobile device) running the app. Prior to a sample being taken, the user may use their mobile device to scan a barcode (such as a 2D barcode or QR code) on the sample collection tube. The app may provide feedback to the user that the barcode scan was successful and may communicate that barcode to the networking platform 701, along with time, date, location information, etc. for the sample collection. As a backup, a copy of the sample tube barcode may be torn off the tube and handed to the patient. This extra barcode may be used as a backup in if the primary pairing between the app and the tube barcode was not successful. The user or medical professional may collect the specimen from the individual and place the swab into the sample collection container. If samples are being taken from multiple individuals sharing a single mobile device, the app may step the user through each member of the family, pairing a unique sample tube barcode for each family member. The collected sample may be shipped or couriered to the closest lab within the GLN 702 that has the ability to quickly test the sample (or, in other embodiments, to another lab or labs depending on the overall time to result for processing the sample sets, the overall health of those labs, and/or the health of one or more aspects within each lab (e.g., operational status of the facility, robustness of necessary utilities, inventory currently stockpiled, etc.), etc.). When the sample arrives at the lab, the barcode on the sample tube may be scanned, the tube decapped, and placed into the lab's sample handling equipment. All subsequent movement of the sample through lab may be specifically traced according to various aspects of the global bio-surveillance and response system 705 as described herein. Results may be uploaded in real time, near real time, in archived batches, etc., through the networking platform 701. In further embodiments, the user may receive a notification, or, for example, an e-mail, on their device that results are available through their device's operating system, e.g., the iOS, Android, Windows notification systems.

In further embodiments, one or more of these tests may be self-administered by the individual to be tested (e.g., from their home or other location) and the processing and result reporting may be either partially or fully automated. In a non-limiting example, an individual would obtain a sample collection tube (e.g., may be requested via a mobile device to be delivered directly to the individual to be tested). The sample collection tube could include one or more barcodes (e.g., 2D barcode, QR code, etc.). The individuals could scan the code, for example, with their mobile device, which could result in one or more of the following: providing the individual instructions with how to self-administer the test and/or ship the collection tube to a testing facility; provide instructional videos relating to the same; associate the collection tube with the individual; providing options for the manner in which the individual will receive the results (e.g., through the same mobile devices, telephonically, via email, etc.); etc. In other embodiments, the results may be directly returned to individual, or they may be transmitted to one or more third parties first, such as the individual's primary care physician, allowing the physician to determine when, how, and/or in what manner to report the results back to the individual. In other embodiments, the results may be reported along parallel paths, such as, for example, to the individuals directly and to their physicians.

The user may unlock their mobile device (user device 706) and use the software to receive the results, which may, for example, be clearly color coded and/or include text that provides the results of the tests for the individual and/or additional family members, presented in the language selected by that user when registering the software. The use of the sample collection software may be used to produce critical data for enhancing testing efficiency and disease outbreak monitoring.

Additional uses of data collected through use of the user devices 706 may include the following. Each use of the software during (or even preceding) sample collection may provide geographical-use data that may be used by officials at the local, national, and world level to monitor the disease's geographical progression, e.g., through the system monitoring subsystem 220. Individuals that test positive may be monitored via their mobile device's location to ensure that they remain within the confines of quarantine or are located at health care facilities. For individuals that test negative, their mobile device may become a passport (the passport may be time-limited) that will allow them to move freely about or to attend events, etc. For individuals that test positive, their mobile device may display an indication reporting the same until a particular point in time, e.g., the disease should have run its course, vaccine development, etc. The software may interact with biometric devices such as a watch that monitors fever, or other vital that may provide an indication of infection.

The geographic and time/date information provided by the software may be used by the GLN for one or more of the following. To deploy and/or allocate appropriate resources, including, for example, increasing the staffing of labs receiving in-bound samples to adequately handle surge capabilities, to steer samples in real time to other nearby labs to load balance sample testing and to prevent the closest geographic labs from becoming overwhelmed, to steer supplies in real time to labs that will have incoming samples; and to set staffing schedules at local labs to accommodate the expected influx of samples. Additional uses for the aforementioned data (e.g., geographical-use data, geographic and time/date information, etc.) are described, for example, in conjunction with the description of identified and de-identified data throughout the disclosure.

In embodiments, during surge conditions, samples may be collected at sample collection sites 709, (see, e.g., FIG. 2A, 202-208), which may further include drive-through or walk-up testing sites, although other means of collections are contemplated as well. Such sample collection sites 709 may work in conjunction with the networking platform 701 of the global bio-surveillance and response system 705, to route samples to one or more GNLs 700 within the GLN 702 (e.g., according to instructions provided by the scheduler module 311). Each site may group 185 samples into a one or more shipping containers (e.g., 185 samples per container, although greater or fewer samples may be included in each). This particular number of samples represents the number of samples that may be executed in a single run (consisting of five plates) on a P5 instrument when running in duplicate, although greater of fewer samples may be alternatively included in each shipping container. Using 185 samples, however, may increase efficiencies of the labs based on instrument runtime and throughput.

Each sample collection site 709 may include one or more shipping label printers connected to the networking platform 701 of the global bio-surveillance and response system 705. Each time a sample set is completed (e.g., 185 samples as per the example used above), lab operators and/or other personnel at the sample collection site may request a shipping label, e.g., through the software running on a computing device (e.g., a test ordering user computer 209, 340) associated with the GNL 700. The networking platform 701 (e.g., via the load balancing module 325 and scheduler module 311) may operate to evaluate available GNLs 700 and determine routing for the sample, e.g., according to the methods described above with respect to FIG. 5. This monitoring may be used to allow the software to select an appropriate GNL 700 (e.g., based on the methods as described with respect to FIG. 5) and print a shipping label for that GNL for routing the sample (or samples). In these examples, the software may spread the sample testing out among the GNLs 700 of the GLN 702 to minimize the turnaround time to obtaining results.

In embodiments, the networking platform 701 may include, among other modules discussed herein, a load-balancing module 325 (see, e.g., FIG. 3B) configured to balance sample, consumable, instrument, and inventory loads and/or requirements across the multiple GNLs 700 of the GLN 702. In embodiments, the load-balancing module 325 is configured to address the potential tradeoffs between queuing samples, sample transit times, available inventory, inventory resupply, and/or instrument distribution/re-distribution among the GLN 702.

In embodiments, the load balancing module 325, within the global bio-surveillance and response system 705 may be configured to minimize workload on the operators at the sample collection sites, who are responsible for placing samples into shipping boxes, printing and affixing labels to sample containers and/or shipping containers, etc. The sample containers may be grouped according to the lab sites listed on the shipping labels and placed into biohazard bags, which in turn may be placed into boxes that may include a shipping label and a unique identifier, such as a 2D barcode, QR code, etc.

There are multiple options for transport of these sample packages to the labs. In an embodiment, standard shipping and/or logistics companies may be employed. In other embodiments, ride share services may be utilized to shuttle samples to and/or from testing labs, leveraging the under-utilization of these services during surge conditions (such as an outbreak, pandemic, etc.).

In an embodiment using a ride share service as an example, the process may include one or more of the following steps, and may be facilitated by software associated with the global bio-surveillance and response system 705, for example, the samples module 311. In an embodiment, operators may print shipping labels (e.g., through shipping label printers associated with one or more of the user devices 706, as discussed above) at appropriate times, such as when an over box is full and and/or the samples have reached the end of their collection sample run. The user device 706 may be configured to automatically notify one or more ride share services that the package is ready to be picked up, delivered, etc. One or more local drivers within the one or more ride share service networks may accept the shipment request on the mobile device and drive to the sample collection site.

At the sample collection site 709, one or more over boxes that are destined for the same laboratory site may be loaded into the ride-share vehicle and the driver may scan the identifier (e.g., 2D barcode, QR code, etc.) on the over box. The driver may employ a user device, such as a mobile device, configured to scan the identifier and identify a destination for the samples box. In embodiments, the destination may include one or more GNLs 700 equipped for sample processing. A navigation system associated with the driver's user device may generate a time-optimized route to the destination GNL 700 and may also monitor the driver's progress to the testing lab. The user device of the driver is further configured to pair the shipment specifically with a driver upon scanning. The over box identifier may then be scanned again when the shipment arrives at the destination GNL 700. At the destination GNL 700, a receiver may employ a user device 706 configured to scan the sample identifier and signify receipt of the samples, triggering an electronic payment to the driver.

In embodiments, these identifiers and/or barcodes may be used to track samples and/or test results at every stage of the process. Using the self-administered test example above, once the user scans the barcode, that sample collection tube and the resulting sample the individual provides will be linked to that user. The identifiers and/or barcode will further be used to track the movement of the sample at every stage it is rescanned. For example, if a courier (e.g., ride share) picks up the sample, the barcode will be first scanned, those reporting to the global bio-surveillance and response system 705 the location, time, etc. of that sample. As the sample, travels to/from a testing facilities (e.g., Tier-1 farm 232), this information will be subsequently recorded each time it scanned (e.g., using the ride-share example, if the sample must be flown to its testing facility, the ride-share courier would scan the identifier and/or barcode once the sample is received at the airport, etc.). Scanning could continue (thus tracking the sample throughout the entire process) up until the sample is received. Additional scans may be performed (either at the beginning and end of the test, or throughout intermediate steps of the test) to allow the global bio-surveillance and response system 705 to track the sample until the tests are complete and the results have been returned to the tested individual and/or other individual and/or entity who is intended to receive the results.

Although other approaches may be employed, the global bio-surveillance and response system 705 configured to leverage ride-share services may provide specific advantages by taking advantage of a transportation network that may be underutilized during conditions requiring a surge approach. For example, ride-share network drivers may be seeking additional work and economic compensation during a surge scenario.

A similar approach may be applied for local transportation of supplies to laboratories from the point where supplies arrive from the depots, e.g., airports. The global bio-surveillance and response system 705, e.g., the networking platform 701, may send out information to a user device 706, e.g., a user device 706 of a ride-share service drive, that supplies are ready to be picked up and transported to a lab. When the driver scans the barcode on the supplies with the user device 706, the user device 706 is configured to display a route to the lab. Payment to the driver may occur when the supplies were scanned in at the target lab. Drivers that have shipments which were scanned at the origination point, but not scanned in at the destination lab within an appropriate period may be flagged and further investigated and/or reprimanded (e.g., kicked off the network and not eligible for transportation of any new shipments) depending on the reasons why the delivery was unsuccessful.

Figure 8:
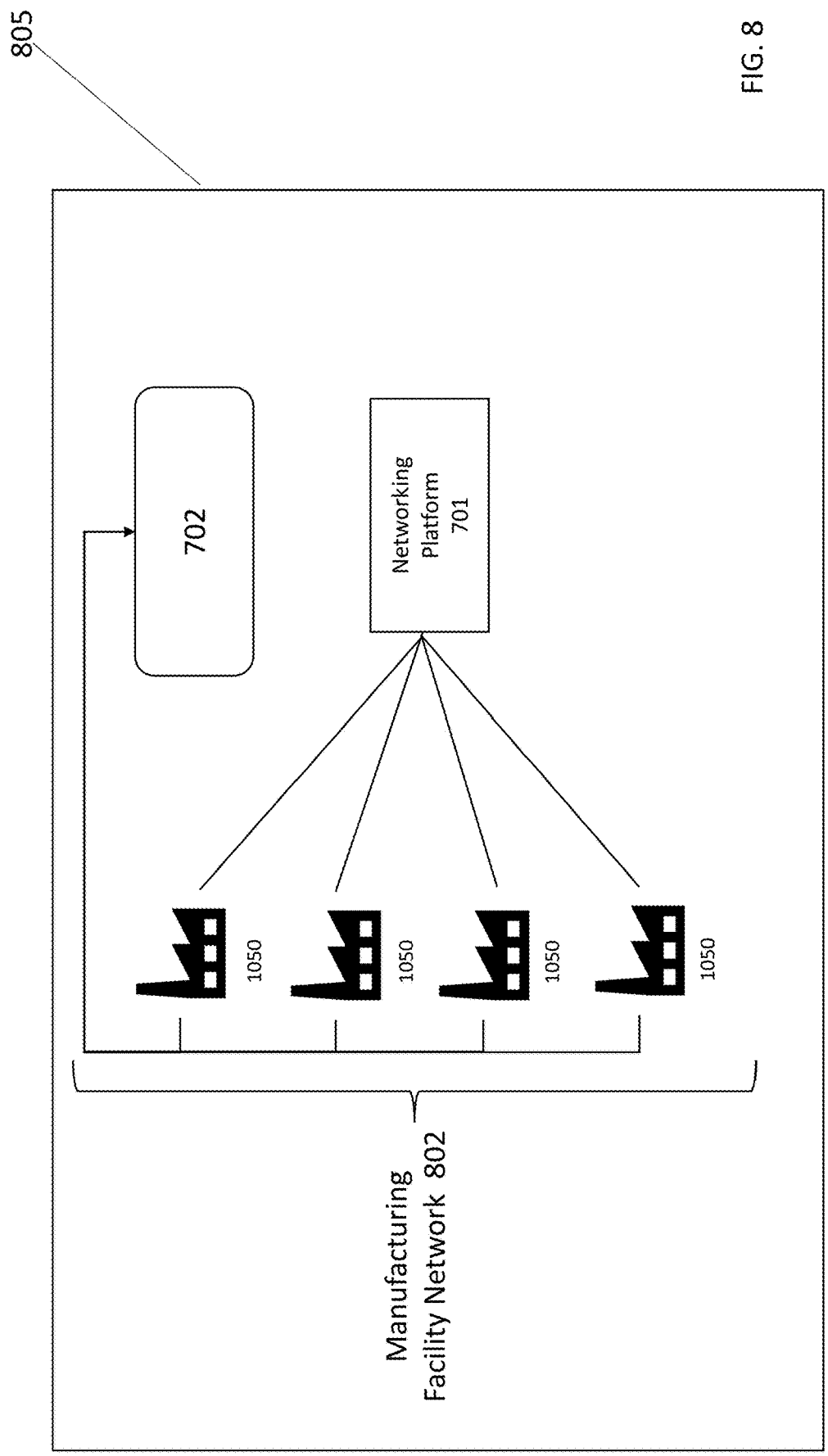
FIG. 8 illustrates a manufacturing facility network consistent with embodiments hereof.

FIG. 8 illustrates a manufacturing facility network of a global bio-surveillance and response system consistent with embodiments hereof. The manufacturing facilities 1050 are arranged in a manufacturing facility network 802 as part of the global bio-surveillance and response system 805. The global bio-surveillance and response system 805 may include any or all of the same features of the global bio-surveillance and response systems as discussed above, e.g., with respect to FIGS. 2, 3A/3B, and 7. In embodiments, six or more major manufacturing facilities 1050 (although greater or fewer are contemplated as well) may be provided, located, for example, in the U.S., E.U., and Asia. Using the pandemic example again, the manufacturing facilities 1050 may be capable of manufacturing high volumes of assay test kits and other consumables, that will be needed during a disease outbreak. The manufacturing facilities 1050 may also serve as depot facilities (as described in greater detail above) to stockpile important components (e.g., equipment, consumables, additional instruments, etc.) that may be required during the early phases of a disease outbreak. Stockpiling may allow the global bio-surveillance and response system to provide adequate time for manufacturing systems to ramp up to full production. In an example, three sites may be located in the United States and three may be located outside the United States (although other geographical arrangements may be contemplated as well). See, e.g., global scheduler processes (e.g., 560-562); regional scheduler processes (e.g., 509-585); farm order processes (e.g., 580-585); and/or user processes (e.g., 500-585).

The manufacturing facilities 1050 of the manufacturing facility network 802 may be interconnected via the networking platform 701. The above-discussed software systems of the networking platform 701, e.g., the inventory module 324 and the load balancing module 325, are configured to coordinate inventory supply throughout the GLN 702 (and other physical locations associated with the global bio-surveillance and response system 805). The networking platform 701 is configured to provide inventory ordering, manufacturing instructions, and shipping instructions to computer systems and personnel associated with the manufacturing facilities 1050. The manufacturing facilities are configured to manufacture the inventory and supplies according to orders and instruction from the networking platform 701 and to distribute the necessary supplies to the GLN 702 and the POC device network 711.

In embodiments, the manufacturing facility network 802 and manufacturing facilities 1050 may provide various functions including one or more of the following, manufacturing large volumes of assay kits and/or other consumables (e.g., plates, reagents, etc.) for the GLN 702, manufacturing large volumes of cartridges for POC devices 710, storing large quantities of generic testing components and testing components that may be rapidly adapted to support the early phases of a disease outbreak.

In embodiments, the manufacturing facility network 802 may be further configured with the following capabilities. These capabilities may provide particular advantage during a pandemic or other disease outbreak or in conditions leading up to a pandemic or disease outbreak. For example, the manufacturing facilities 1050 may each include one or more of the following capabilities. Each facility 1050 may be configured with the ability to rapidly react to the initial phases of a testing surge. Each facility 1050 may include stockpiles of test kit components and other consumables that may be rapidly converted to products that may be used test for one or more target pathogens (for example, utilizing the phased approach set forth above). In a non-limiting example, the facilities may stockpile approximately 17 million assay plates to cover the use of 200,000 plates per day for a three-month period, and approximately 1.5 billion cartridges to cover the use of cartridges for one month. In addition, the facilities may stockpile one or more of: 500 M sample tubes that may each include a sample swab and viral transport media, 500 M swabs that may be used with swab cartridge, sufficient raw material plastic for manufacturing plates and cartridges for a six-month period, sufficient materials for screen printing plate and cartridge electrodes for a six-month period.

The facilities 1050 may further be configured with the ability to rapidly manufacture large quantities of testing kits. For example, these facilities 1050 may be used to manufacture a sufficient number of test kits (or other consumables) to support surge testing for the deployed Tier 1, Tier 2, and Tier-3 labs as well as the deployed cartridge reader instruments. Further, under surge conditions, 1,000 Tier 1 and Tier 2 labs (or any other number of labs) may utilize approximately 200,000 plates per day and 1.4 million plates per week to provide a total of approximately 104 million tests per week. In one specific embodiment, under surge conditions, the labs may run an estimated 2 million cartridge readers, 12 hours per day, with a 30-minute time to result. Working under these assumptions, the facilities may produce 48 million cartridges per day or 8 million cartridges per manufacturing site per day, assuming six facilities 1050.

Still further, the facilities 1050 may include the ability to provide high levels of automation. For example, the manufacturing facilities 1050 may be designed to reduce the workforce to a minimum, thus minimizing the number of individuals who would need to be on-site during an outbreak. The manufacturing facilities 1050 may be automated as well, such that specialized skills may not necessarily be required to manufacture product, thus minimizing the risk of operation during a pandemic. Partial and/or complete automation of the manufacturing facilities may further decrease an amount of time required to train additional workers to staff a manufacturing facility during a pandemic, and it may further reduce the need to cross train individuals on many different aspects of the operation.

Moreover, the facilities 1050 may further be configured to provide high levels of vertical integration. Because global supply chains may be fragile during a pandemic, each manufacturing facility 1050 may be vertically integrated and able to manufacture large quantities of test kits even if supply chains break down. Further, the facilities may be configured to stockpile materials to manufacture continuously for six months (or a longer or shorter period) without receipt of additional materials.

Further, the facilities 1050 may be configured with an ability to sustain manufacturing under pandemic conditions. Each facility 1050 may be designed to support such measures as social distancing and to avoid areas where many workers need to congregate. Facilities 1050 may have pre-existing stocks of temporary partitions, to quickly segregate various manufacturing areas, which may limit the possibility of disease spread within the facility. Further, the facilities 1050 may have pre-existing memorandums of understanding with nearby hotels so that facility employees may temporarily be housed to improve and individual safety, curb the spread of disease, and minimize commute times. Moreover, facilities may be stockpiled with personal protective equipment ("PPE"), such as masks, face shields, gloves, goggles, and/or other PPE.

Additionally, the facilities 1050 may be located proximate to major transportation networks. The facilities 1050 may be strategically located to be proximate to major transportation hubs, airports, etc. Major road networks may be required for the receipt of incoming materials and distribution of test kits and other consumables. Further, a rail lines may be needed as well at each site to transport large quantities of plastic for injection molding of plates, cartridges, and other consumables.

Finally, the facilities 1050 may further leverage redundancy of utilities and communications connections. Although sites may be primarily fed by major utilities, each facility may include backup power (for example, to be provided via a natural gas pipeline to each site that will be used to power natural gas turbine generators, other through other means of power generation) and water capability in the event of interruptions of utilities. Sites may further utilize land-based internet connections that may be backed up by satellite internet connections.

Although redundancies may be built in for various utilities and communications as described above, in particular, redundancies built around multifunctional utilities may be of particular import in several embodiments. In a non-limiting example, water and power redundancies may be built into various labs, farms, and/or other facilitate the sterilization (e.g., heating water to generate steam) of equipment, instruments, facilities, etc.

Figure 9:
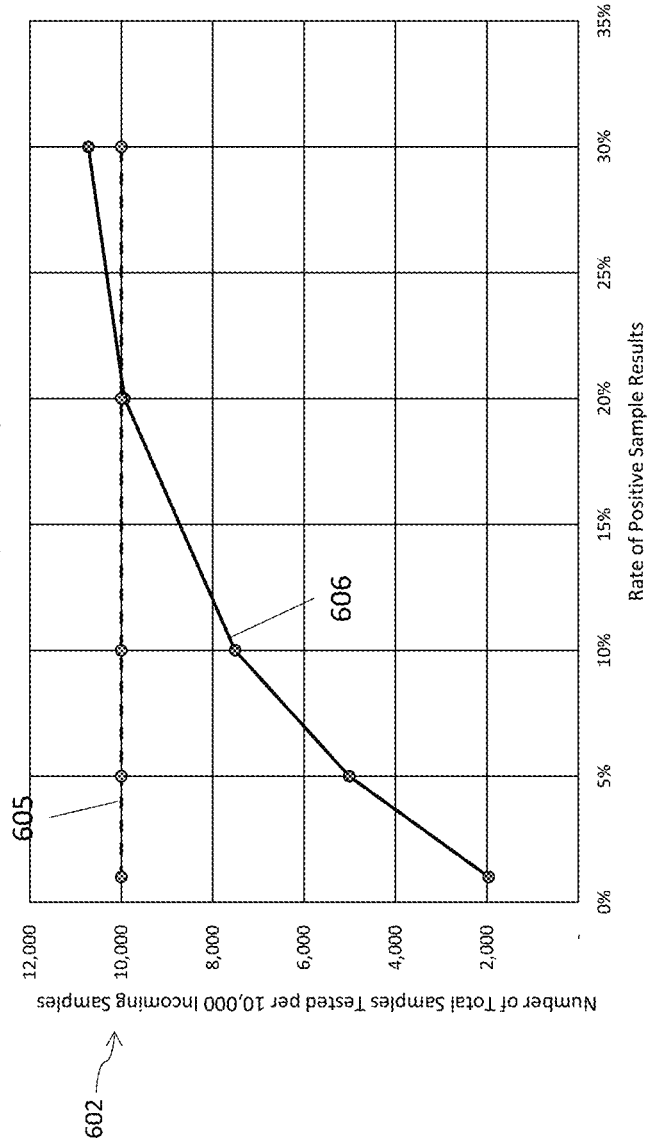
FIG. 9 depicts a graphical and tabular view of a non-limiting exemplary embodiment of sample pooling results in accordance with the certain aspects of the disclosure.

FIG. 9 illustrates an example of sample pooling in tabular and graphical formats illustrating the effect of sample pooling at various positive test rates. In embodiments, the global bio-surveillance and response system 705 may be configured to facilitate sample pooling. Sample pooling is an example of one approach to increase sample throughput, which may be particularly useful during surge conditions. By pooling 10 samples together, for example, and testing that sample as a single unit, testing throughput, depending on the results, may increase up to ten-fold. If a pooled sample tests positive, individual samples that comprise that pooled sample may be retested to identify the one or more individual samples that were positive.

The samples module 311 may be configured to support, organize, and/or facilitate pooled sample testing at various levels of pooling (e.g., 5, 10, 20, or any other integer value). For example, the samples module 311 may provide instructions to operators and bioinstrumentation devices associated with a GNL 700 to coordinate sample pooling. In embodiments, the ability to pool samples may be a function of the sensitivity of the test (e.g., assay) given that negative samples may dilute positive samples. Ultra-sensitive assays may be employed—such as, for example, those assays disclosed in U.S. Application No. PCT/US2014/026010, filed on Mar. 13, 2014, incorporated herein by reference—which may be used to result in significant increases in assay sensitivity and supporting sample pooling. When a positive result is identified within a pooled sample, e.g., via the results module 310, the samples module 311 may be employed to facilitate additional sample collection and individual testing of the individuals that contributed to the positive pooled sample.

The effectiveness of sample pooling may be a function of the rate of positive samples. For example, as the rate of positive samples increases, the number of pooled samples that may then need to be re-tested increases. The cost/benefit inflection point of sample pooling (using the 10 sample pool example described above) is approximately 20%. FIG. 9 describes an example of sample pooling in tabular and graphical formats illustrating the effect of sample pooling at various positive test rates. In FIG. 9, the dotted line 605 represents the total sample load, e.g., number of tests required per 10,000 incoming samples in an unpooled scenario. In the unpooled scenario, the total sample load is flat, as all samples are tested regardless of positivity rate. The solid line 606 represents the total sample load in a pooled scenario. As the positivity rate increases, the number of pooled samples requiring a full re-test increases. As shown in the graph and table, when the positivity rate reaches approximately 20% in this scenario (e.g., a 10 sample pool), the benefits of sample pooling are approximately eliminated. This inflection point may vary depending on the pooling factor utilized.

In embodiments, the global bio-surveillance and response system 705 may operate in multiple phases of activity during surveillance and surge conditions. For example, under non-surge conditions, Tier-1 and Tier-2 GNLs 700 (for example, as part of the sample processing subsystem (see, e.g., FIG. 1A, 103)) may perform routine testing of samples through action as the sentinel subsystem to identify a health condition against an upper respiratory panel (or any other panels) containing assays for influenza A and B, respiratory syncytial virus (RSV), adenovirus, and coronaviruses, among others. Through this testing, certain indicators may be closely scrutinized to determine whether a health condition (e.g., a new or emerging pathogen) is present and/or whether an outbreak, pandemic, endemic, etc. is potentially imminent.

In embodiments, one such way of accomplishing this may be by identifying samples that come from symptomatic patients that test negative across the panel (such as in an upper respiratory disease as in the example used above). Samples that match this pattern may indicate the presence of a newly circulating pathogen that must be identified, sequenced, etc. to mitigate the risk of infection, spread, etc. For example, Tier 1 and Tier-2 labs include the most current generation sequencing capability to rapidly interrogate these types of samples. In other examples, particular samples of interest may be retested, tested across a greater battery of tests, etc.

Upon the identification of a new pathogen (or upon one or more triggering events), a series of steps may be initiated to rapidly escalate testing capability and to move labs into a surge testing stance, e.g., Surge Mode. In embodiments, assays selected from those disclosed in U.S. Application No. PCT/US20/30754, filed on Apr. 30, 2020 and incorporated herein by reference may be employed during this phased approach; the steps may include one or more of the following phases:

Although many of the examples that follow contemplate applying this phased approach globally, in embodiments, one or more of the phases can be limited regionally and/or to one or more isolated regions (e.g., assay development under phase 1 may only require direct detection of a pathogen located in a limited geographical area). In this example, phase 1 could be applied only to that geographical region only (and/or surrounding geographical regions), or, in other embodiments, could be applied globally as well.

Turning to phase 0, in embodiments, the global bio-surveillance and response system 700 is configured to operate the GLN 702 in a phase 0 surveillance posture. Phase 0 testing may consist of routine testing against a standard panel, e.g., upper respiratory panel, to identify health conditions. A percentage of samples from patients that are symptomatic, but test negative across the respiratory panel may be sequenced using next generation sequencing to obtain a more complete understanding of one or more potential pathogens, indicating a health condition, that are present. The results module 310 may be configured to receive deidentified data from sample processing and associate such data with symptom information, demographic information, and additional non-identifying information from the individuals associated with the samples. The symptom information may include information collected by humans and/or information collected via automated systems (e.g., by questionnaire).

In embodiments, the global bio-surveillance and response system 700 is configured to operate the GLN 702 in a phase 1 surge posture. Entrance into a phase 1 surge posture may be triggered if a new pathogen or pathogen strain is detected via sequencing. Phase 1 surge posture may include an immediate stand-up of assays for the target pathogen. All Tier 1 labs within the GLN 700 may include assay development capabilities, as discussed above, allowing these labs to quickly develop new and/or unique assays for the pathogen. The Tier 1 and Tier-2 labs may also include nucleic acid synthesis capabilities allowing all labs to manufacture the nucleic acid reagents needed for assays. Phase 1 provides direct detection assays to differentiate infected patients from non-infected patients. Phase 1 detection may be deployed globally and/or regionally, as necessary. For contagious health conditions (e.g., viral infections), a global shift to phase 1 surge may be necessary to monitor the global progress of the disease. For non-contagious health conditions, including radiation exposure, exposure to bio-chemical toxins, etc., regional surge to phase 1 may be preferred.

In embodiments, the global bio-surveillance and response system 700 is configured to operate the GLN 702 in a phase 2 surge posture. In parallel with Phase 1 (or in series with, e.g., after Phase 1), Tier 1 GNLs 700 may enter phase 2 and initiate the development of serological assays for testing serum and plasma samples, among other sample types. All Tier 1 GNLs 700 may include protein manufacturing capabilities, enabling them to scale up the manufacturing of antigens associated with the pathogen based on the initial sequence information gained in Phase 0. Initially, the antigens may be tagged with nucleic acid sequences so that serology assays may be quickly built using readily available assay plates—see, for example, those disclosed in U.S. Application No. PCT/US2014/022948, filed on Mar. 11, 2014; and U.S. Application No. PCT/US2015/03092, filed on May 15, 2015, incorporated herein by reference. Another example of a suitable assay may include those assays described in U.S. Application No. PCT/US2014/010016, filed on Jan. 2, 2014, incorporated herein by reference. Phase 2 surge posture may further provide serology assays to differentiate those that have been infected and recovered against those whose immune systems are naïve to the pathogen.

In embodiments, the global bio-surveillance and response system 700 is configured to operate the GLN 702 in a phase 3 surge posture. Throughout the above-discussed phases, the personnel associated with GNLs 700 of the GLN 700, e.g., assay development teams, may be working to develop direct detection immunoassays for the pathogen. These assays may use, e.g., monoclonal antibodies, which may be placed into development as soon as antigens are available for mouse (or other non-human) immunizations. Antibody development may proceed as rapidly as possible, e.g., over a four-month timeline, which is fairly typically, although other shorter or longer timeframes are contemplated as well. Once antibodies are available, assay development may proceed and may include the various phases of antibody screening, capture and detection antibody concentration optimization, cross-reactivity testing, and diluent testing, among others. Phase 3 surge posture may result in a rapidly developed, high-quality, low-cost direct detection assay that may be used throughout the GLN 702. Additionally, the assay may be added to the routine test panel (e.g., an upper respiratory disease panel), incorporating the newly identified pathogen into the GLN's routine testing of samples through a surveillance subsystem.

In embodiments, this phased approach may be utilized for a logical progression of different tests, assays, antibody development, etc., as additional information is obtained from previous tests. For example, one or more of the above-described processes may be used for assay, antibody, and/or vaccine development. Using an emerging pathogen as an example, as the phrased approach unfolds, rapid development of serological assays may be performed, thus providing both efficient and effective screening tools for not only the emerging pathogen, but also any variations and/or mutations thereof. In particular, multiplexed nucleic acid-based testing (for example, although other tests are contemplated as well) may be used to optimize the development these assays and/or vaccines. Moreover, these and other single and/or multiplexing techniques provide the systems and subsystems described throughout the additional ability to screen for and combat variants of those now-emerged pathogens.

In embodiments, the systems, methods, and apparatuses associated with the global bio-surveillance and response system 705 may include one or more Point-of-Care devices 710 (also referred to herein as sentinel devices) arranged in a Point-of-Care (POC) network 711 to test frequently, quickly, and throughout the entire globe. POC devices 710 may be employed as part of the sample collection and test ordering subsystem (FIG. 1A, 101), the independent sample testing subsystem (FIG. 1A, 104), and/or the one or more distributed sentinel devices (FIG. 2A, 241).

Referring again to the pandemic example, specifically, this may be accomplished, for example, by placing testing capabilities as closely as possible to where the testing is needed. In one embodiment, test equipment, such as cartridge readers—for example, those disclosed in U.S. Application No. PCT/US03/041241, filed on Dec. 23, 2003; U.S. Application No. PCT/US2010/058913, filed on Dec. 3, 2010, incorporated herein by reference—may be deployed as POC devices 710 to provide direct pathogen detection and/or swab assays and serology assays in a very compact, portable package that may be widely deployed to such sites as field locations, business offices, etc. In one example, approximately one million cartridge readers may be deployed in the United States and another one million deployed worldwide (other numbers greater or fewer than these may be employed as well) to provide a global test capability that may quickly identify and control disease outbreaks and minimize the human and economic cost of disease outbreaks. In a non-limiting, exemplary embodiment, the one or more distributed POC devices 710 may be employed to carry out one or more of these tasks (see, e.g., FIG. 2A, 241).

In embodiments, POC devices 710 arranged in a POC network 711 may be configured to provide field-testing capabilities. For example, cartridge readers are lightweight (often less than 15 pounds) and may consume very little power (e.g., no more than 30 watts). These instruments are often highly compact, making them ideal to be placed into field locations where it may be critical to test individuals and to acquire results quickly (e.g., within 30 minutes). This platform may be used to test patients before instances of close contact such as dentist appointments, schools, doctor's office visits for care unrelated to health conditions associated with an emerging pandemic, air travel, and others. Similarly, it may be used in military applications where full lab capabilities may not be available such as navy ships and forwarded deployed forces, etc. In further embodiments, POC devices 710 may be deployed via vehicles to provide mobile testing capabilities.

In embodiments, POC devices 710 arranged in a POC network 711 may be configured to provide automated sample-to-answer capabilities. Cartridge readers are often easy to use and may be made compatible with at least two different cartridge types—e.g., swab-based samples and liquid-sample (such as serum or plasma, etc.). After loading the sample, the instrument may process and analyze the same through an automated process. The results may then be provided in a simple and clear positive/negative-result format to the user. All of these steps may be easily accomplished, even by individuals with little-to-no training on the instrument or cartridge. In field clinical trials, for example—both in the United States as well as at overseas locations—it took no more than 30 minutes to train a user on the use of the cartridge reader. Once complete, the system may provide a clear positive/negative result to the user. The POC devices 710 permit users to acquire high quality results with minimal training, irrespective of the user's skill level or capabilities.

In embodiments, POC devices 710 arranged in a POC network 711 may be configured to provide real-time global results reporting via IT infrastructure, for example, via the networking platform 701: POC devices 710 may further be capable of interacting with the networking platform 701 to upload geographically tagged results in real-time from the instrument to the global bio-surveillance and response system 705. These data may be made available through the system monitoring subsystem 220 feature (e.g., mission control), which is described in greater detail below, along with data coming from the GLN 702.

In embodiments, POC devices 710, such as cartridge readers, arranged in a POC network 711 may be configured to provide additional advantages that may make them highly desirable for use in field or point-of-care settings. For example, cartridge reader POC devices 710 may be designed to be compact, fully automated instruments. For example, for swab-based testing, after sample collection (e.g., nasal swap), the swab may be inserted into the cartridge and all subsequent processing steps, including swab extraction, assay processing, and presentation of results may be fully automated, without requiring additional invention. Liquid cartridge formats may be also made available for handling liquid samples such as plasma, serum, sputum, bronchoalveolar lavage (BAL), urine, whole blood, etc. The liquid cartridge typically requires only a relatively small sample of liquid (e.g., 125 µL) which may be delivered manually into the cartridge; after which the remaining steps may all be fully automated. The cartridges may be multiplexed, allowing for a single sample to be tested for multiple target analytes. The reader may produce a result in a short time period (typically 30 minutes or less) and produce automatic result evaluation. The liquid sample cartridge may be useful for serological assays for viral exposure or vaccine titer determinations, as well as for host biomarker assays that may indicate the severity of disease for an individual.

Cartridge readers may be far more sensitive in detecting certain viruses, such as influenza, as compared to rapid strip tests (up to 100 times more sensitive in accordance with head-to-head testing). Cartridge reader may offer a broad range of solutions. For example, they may be, and have been, used in programs to test for pandemic influenza, biomarkers indicative of radiation exposure, biomarkers indicative of traumatic brain injury, etc. Thus, these readers may be used to address a broad range of localized and/or global catastrophes or other events, including, for example, pandemics and/or for detecting events leading up to a pandemic, bio-defense applications, biodosimetry applications, as an epidemiological infrastructure tool, etc.

In a non-limiting, illustrative embodiment, an example of one such reader as a POC device 710 may include an instrument used for POC immune-diagnostic testing. In this example, the POC device 710 may comprise a compact immunoassay cartridge reader instrument that utilizes single-use, micro-fluidic cartridges and additional technology to enable multiplexed, electrochemiluminescence (ECL) measurements on biological and environmental samples. The instrument may process different sample types, such as nasal and environmental swabs, plasma, and whole blood, and has potential utility in applications such as infectious disease diagnostics, clinical biomarker measurements, radiation exposure, traumatic brain injury (TBI) assessment, and both clinical and environmental biothreat detection. To support the rapid scale up of use of the Cartridge Reader in outbreak scenarios, multiple versions of the cartridges may be employed and will have the ability to support flexible use of the system. Table 3 describes the various cartridge types that may be employed, located at the conclusion of the description. Under non-surge conditions (e.g., Surveillance Mode), cartridge readers may be used to perform testing of samples through the sentinel subsystem against a panel (e.g., an upper respiratory panel) containing assays for influenza A and B, respiratory syncytial virus (RSV), adenovirus, and coronaviruses, among others. In additional embodiments, the above-referenced testing may be supplemented with predictive testing as well (e.g., testing of face masks, environmental surfaces, etc. to indicate presence of a pathogen, for example).

In some embodiments, the global bio-surveillance and response system 705 may be used to recommend modifications to human interactions, alter occupational precautions, adjust testing frequencies, etc. For example, the system monitoring subsystem in operation on the networking platform 701 may be configured to provide such modifications and alterations to one or more sites in a POC network 711, one or more GNLs 700, and one or more sample collection facilities associated with the global bio-surveillance and response system 705. In embodiments, the system 705 may rely on one or more of the independent sample testing subsystem 104, the sample collection and test ordering subsystem 101, and the system monitoring subsystem 102 (FIG. 1) to perform one or more of these functions (although other subsystems described throughout are contemplated as well). In a non-limiting example, testing may performed (either of one or more individuals, environmental surface testing, testing of other safety equipment such as, for example, personal protective equipment ("PPE") (e.g., face masks, gloves, eye protection, etc.) etc. at a place of business (e.g., a law firm), government building (e.g., a public library), etc. to detect a health condition and/or biological, chemical, bio-chemical, nuclear, radiological, etc. anomaly, such as an emerging pathogen. Using the public library as an example with an emerging pathogen as the exemplary heath condition, all or a subset of individuals may be tested (e.g., detecting the presence of related antibodies, antigens, etc.) upon entering the library. Moreover, surfaces, such as computers, desks, etc. may be tested as well. Depending on the results of those tests, the global bio-surveillance and response system 705, e.g., the system monitoring subsystem 102 may recommend a modification to human interaction by placing social-distancing restrictions in place (either on all individuals who enter or just those with particular results, etc.), mandating additional safety precautions (e.g., requiring masks and/or eye protection while inside the facility, etc.). Moreover, depending on the results, the global bio-surveillance and response system 705 may use these results to adjust test frequency and/or sampling rates (e.g., no or a relatively low number of positive results obtained over a given period of time could reduce the need to perform 100% sampling of individuals, reduce the number of environmental surfaces to test, etc.), and vise-a-versa (increasing rates if rates of positive results from one or more of human and environmental surface testing increase as well).

TABLE 4

| Basic Cartridge Type | Discussion | Phase Use |
| --- | --- | --- |
| Swab | In early stages of Phase 1, NA sequences may be produced in bulk liquid. A basic NA coated cartridge may be adapted to look for the pathogen of interest. | Phase 1A |
|  | Following early stages of Phase 1, natively manufactured cartridges with the correct NA sequences on each spot may be available. | Phase 1B |
|  | In phase 0, a swab cartridge may be a standard sandwich immunoassay cartridge. Once antibodies are available for the pathogen, standard cartridges may be manufactured with assays for the new pathogen alone or the assay may be added to the normal surveillance panel, e.g., in phase 3. | Phase 0 and Phase 3 |
| Liquid Sample | In early phase 2, To support rapid scale up of serology assays on the cartridge, antigens may be produced with nucleic acids at Tier 1 labs or at manufacturing points. This approach may permit rapid manufacturing of serology cartridges in the initial phase of response. | Phase 2A-Initial serology assays using NA tagged antigens |
|  | As cartridge manufacturing ramps up, cartridges may be produced using direct printing of antigen onto electrode spots. | Phase 0 and Phase 3 |

In embodiments, additional testing and/or retesting may be performed for symptomatic patients that test negative across the test panels, such as upper respiratory disease panels, (e.g., these samples may indicate that a new pathogen is circulating). Upon identification of a new pathogen (or upon one or more triggering events), a series of steps may be initiated to rapidly escalate testing capability and to move labs into a surge testing stance, e.g., Surge Mode. In embodiments, assays selected from those disclosed in U.S. Application No. PCT/US20/30754, filed on Apr. 30, 2020, incorporated by reference herein, may be employed during this phased approach. The phased approach discussed below may be employed by a global bio-surveillance and response system 705 for use of POC devices 710. The phased approach may be employed in lieu of, in conjunction with, or simultaneous to the above-discussed phased approach described with respect to the GLN 702.

In embodiments, the global bio-surveillance and response system 705 may be configured to implement the network of POC devices 710 in a phase 0 sentinel posture. This phase may consist of routine testing against a standard upper respiratory panel, or any other testing panel. A percentage of samples from patients that are symptomatic, but test negative across the respiratory panel may be sequenced using next generation sequencing. The results module 310 may be configured to receive data from sample processing and associate such data with symptom information from the individuals associated with the samples. The symptom information may include information collected by humans and/or information collected via automated systems (e.g., by questionnaire). The prevalence of individuals presenting with symptoms and that test negative may be monitored via the one or more user devices 706 that requests information on symptoms and metrics such as body temperature, or other relevant vitals, etc. Once a new pathogen or new strain of an existing pathogen or emerging pathogen that is eluding normal testing is identified, the manufacturing of cartridges may move to Phase 1.

In embodiments, the global bio-surveillance and response system 705 may be configured to implement the POC network 711 of POC devices 710 in a phase 1 surge posture. In phase 1, the global bio-surveillance and response system is configured to establish direct testing capability via POC devices 710 in as short a time frame as possible. Early phase 1, phase 1A, may utilize large quantities of pre-stocked cartridges that may be adapted via reagent addition to test for the new pathogen. Later stage phase 1, phase 1B, may consist of newly manufactured cartridges that may test for the new pathogen.

In embodiments, the global bio-surveillance and response system 705 may be configured to implement the network of POC devices 710 in a phase 1A surge posture. Phase 1A may include the rapid stand-up of assays to the new pathogen using assay cartridges. In Phase 1A, cartridges with generic nucleic acid arrays, that have been stockpiled in large quantities, may be adapted to test for the new pathogen. The cartridges may be adapted, for example, through the addition of liquid reagents that will bind to and modify the generic nucleic acid array to one that has the correct nucleic acid sequences to test for the new pathogen.

In embodiments, the global bio-surveillance and response system 705 may be configured to implement the network of POC devices 710 in a phase 1B surge posture. In parallel with Phase 1A's sourcing of generic nucleic acid cartridges from the depot stockpiles (or in series with that phase), new cartridge manufacturing may start at various manufacturing plants. These new cartridges may be manufactured with nucleic acid arrays, for example, that may test for the specific pathogen rather than relying on the addition of liquid reagents as in Phase 1B.

In embodiments, the global bio-surveillance and response system 705 may be configured to implement the network of POC devices 710 in a phase 2 surge posture. In parallel, for example, with Phase 1, Tier 1 GNLs 700 (as discussed above), the global bio-surveillance and response system 705 may initiate the development of serological assays for testing serum and plasma samples. All Tier 1 GNLs 700 may have protein manufacturing capabilities, enabling them to scale up the manufacturing of antigens associated with the pathogen based on the initial sequence information gained in Phase 0. Phase 2 may provide serology assays to differentiate those that have been infected and recovered against those whose immune systems are naïve to the pathogen. The serology testing may also be used to facilitate in vaccine development.

In embodiments, the global bio-surveillance and response system 705 may be configured to implement the network of POC devices 710 in a phase 2A surge posture. In this phase, cartridges for serology assays may be manufactured for POC device 710 use using antigens that are tagged with nucleic acid sequences. In parallel to this phase (or, in the alternative, before, or after this phase) the use of generic cartridges with nucleic acid arrays that are then-modified with antigens tagged with complementary nucleic acid sequences may be employed to allow the quick instantiation of serological testing capability.

In embodiments, the global bio-surveillance and response system 705 may be configured to implement the network of POC devices 710 in a phase 2B surge posture. As Phase 2B proceeds, new cartridge manufacturing may be ramped-up across one or more commercial manufacturing plants. All new cartridges may use arrays of antigens (e.g., same antigens as Phase 2A) that are directly immobilized on the cartridge's capture array.

In embodiments, the global bio-surveillance and response system 705 may be configured to implement the network of POC devices 710 in a phase 3 surge posture. Throughout these phases, the GLN 702 development team may work to develop direct detection immunoassays for the pathogen. These assays may use monoclonal antibodies which will be placed into development as soon as antigens are available for mouse immunizations. Antibody development may proceed as rapidly as possible, e.g., over a four-month timeline, which is fairly typically, although other shorter or longer timeframes are contemplated as well. Once antibodies are available, assay development may proceed and may include the usual phases of antibody screening, capture, and detection antibody concentration optimization, cross-reactivity testing, and diluent testing, among others. Phase 3 may result in a high-quality, low-cost direct detection assay cartridge. Additionally, the assay may be added to the routine respiratory disease test cartridge, incorporating the newly identified pathogen into cartridges in routine POC testing. Transitions between phases, for the GNL 702, the network of POC devices 710, and for the global bio-surveillance and response system 705 as a whole may be implemented by the phase transition module 327 in operation on the networking platform 701 and in communication with the system monitoring subsystem. The phase transition module 327, in embodiments, may operate autonomously, selectively sending out instructions for phase changes to the necessary localities, autonomously with oversight, wherein phase transitions are suggested and confirmed by human operators, or entirely through human decision.

In an autonomous mode, phase transitions may be determined by the phase transition module 327 according to various mathematical rules. For example, phase transitions may be based on positivity rates, overall case-loads or counts, rate of increase of each of these, increase of rate of increase of these, etc. In embodiments, some of all of these data may be provided as part of de-identified data (as described in greater detail above. Those data may be derived internally, received externally from one or more third-party providers, or combinations thereof). Other metrics, such as morbidity rates, mortality rates, hospitalization rates, respirator requirement rates, symptom trends (e.g., average fever of positive individuals), as well as first and second derivative trends in these rates may be employed to determine phase transitions. Phase transitions between the various phases may be determined by the phase transition module 327 for specific localities, e.g., among one or more GNLs 700, across whole regions of GNLs 700, and, if necessary, globally across an entire GLN 702. When phase changes are triggered, the phase transition module may send instructions to the GNLs 700, POC devices 710, manufacturing facilities, etc., associated with the global bio-surveillance and response system 705 to implement the phases described above.

In a semi-autonomous mode, the phase transition module 327 may implement the same rules and approaches to phase changes as described above, but may provide the outcomes of such analyses as recommendations to a human operator. The human operator may then interact with the phase transition module to authorize or refuse the recommended phase transitions. The human operator may further authorize additional phase transitions. When phase changes are authorized, the phase transition module may send instructions to the GNLs 700, POC devices 710, manufacturing facilities, etc., associated with the global bio-surveillance and response system 705 to implement the phases described above.

In a fully manual mode, the phase transition module 327 may implement the same rules and approaches to phase changes as described above, but provide only raw data to a human operator. The rates, trends, and other data discussed above may be provided to one or more human operators to determine phase transitions at their discretion. When phase changes are authorized, the phase transition module may send instructions to the GNLs 700, POC devices 710, manufacturing facilities, etc., associated with the global bio-surveillance and response system 705 to implement the phases described above.

The systems, methods, and apparatus described herein may include software with Mission Control functionality. See, e.g., system monitoring subsystem (FIG. 1A, 102; FIG. 3, 342, FIG. 6, 220). This functionality may provide the software with the ability to gather and present a single unified picture of all the activity and results within the GLN 702 and among all the deployed POC devices 710 in the POC network 711 (e.g., cartridge readers). The system monitoring subsystem may further permit users to interact with and provide instructions to various operators, use, laboratories, user devices, etc., associated with the global bio-surveillance and response network 300. This single, unified picture or dashboard may be deployed and utilized at government sites as well as one or more private entities for the supervision and/or management of ongoing activities. The mission control functionality may be implemented through the networking platform 701, or through the various other networking platforms described herein.

In embodiments, and as discussed above, the data obtained from tests (e.g., performed by one or more POC devices 710, farms (e.g., FIG. 2A, 232)), etc.

Figure 10A:
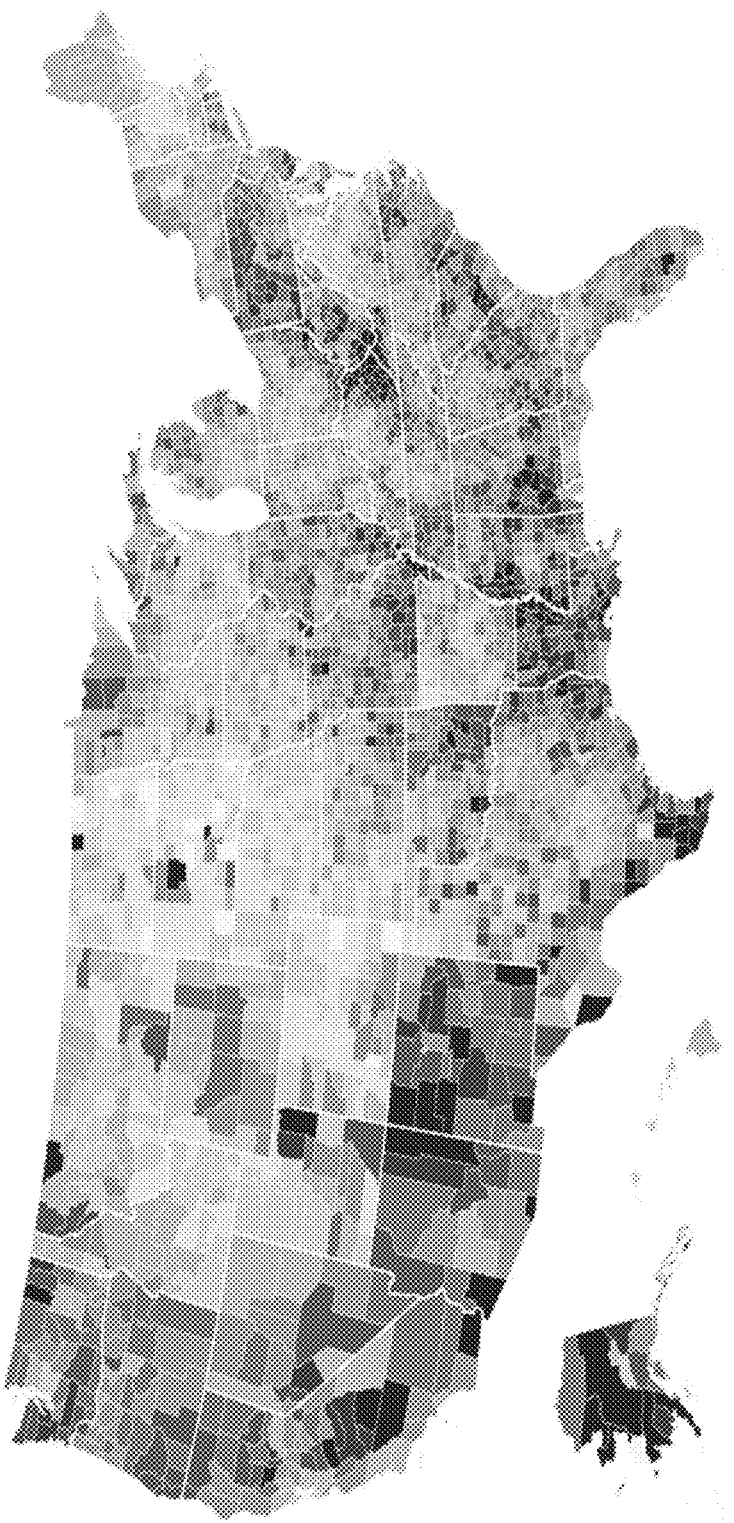
FIG. 10A depicts a map-based view of a non-limiting exemplary embodiment of the Mission Control feature in accordance with the certain aspects of the disclosure.
Figure 10B:
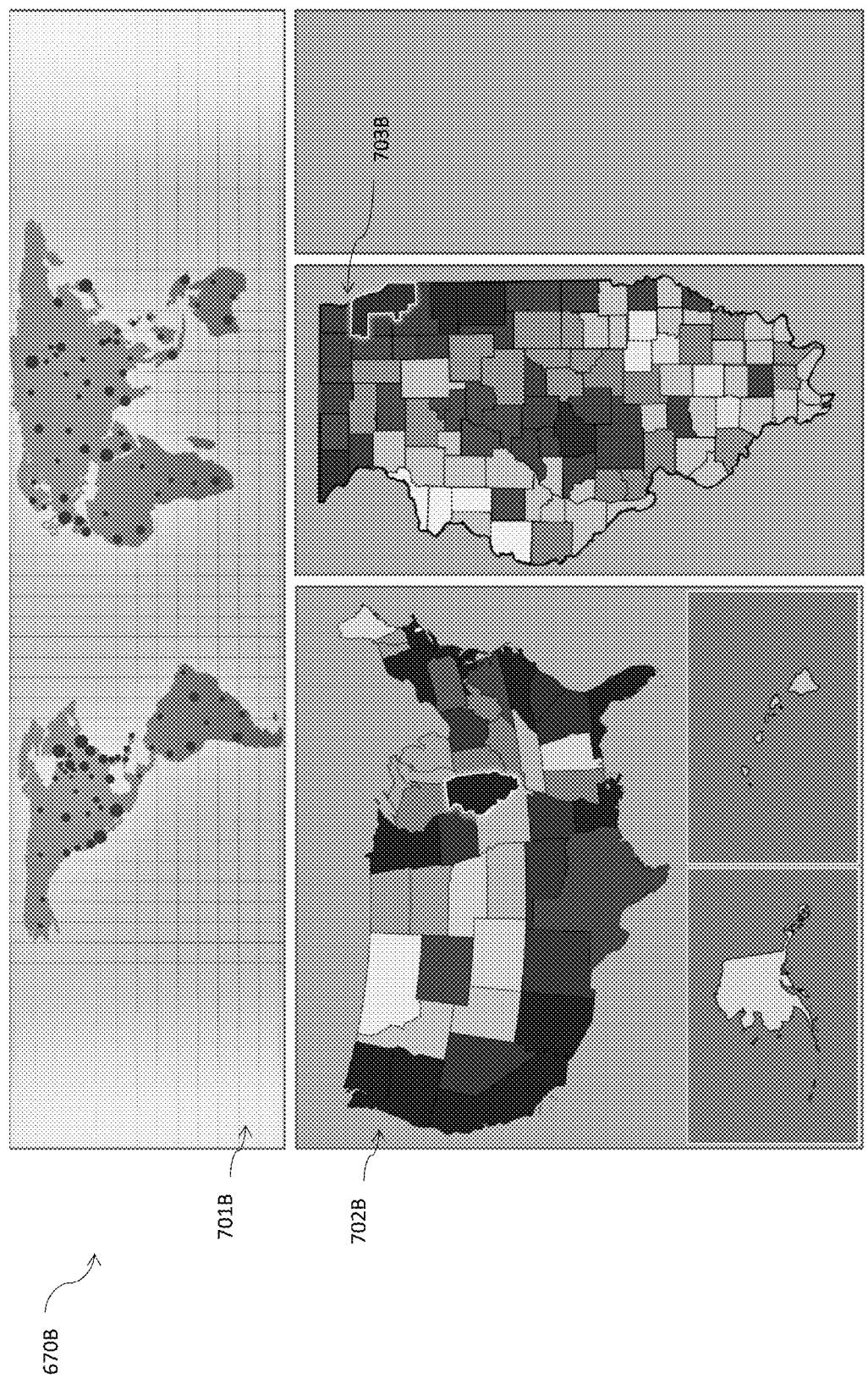
FIG. 10B depicts a map-based view of another non-limiting exemplary embodiment of the Mission Control feature in accordance with the certain aspects of the disclosure.

FIG. 10A illustrates a map-based view of a non-limiting exemplary embodiment of the Mission Control feature in accordance with the certain aspects of the disclosure. FIG. 10B illustrates a map-based view of a further non-limiting exemplary embodiment of the Mission Control feature in accordance with the certain aspects of the disclosure. As described above, the Mission Control features described below may be implemented by the system monitoring subsystems described herein, e.g., at FIG. 1A, 102, FIG. 2A, 220, FIG. 3, 342, and/or at FIG. 6, 220, for example, by one or more mission control computers 221, 342. These figures will be described in conjunction with one another.

More specifically, FIGS. 10A and 10B illustrate non-limiting embodiments of real-time results provided by the system monitoring subsystems described herein, including real-time information collected in connection with the sentinel (surveillance) subsystem regarding positive and negative samples as information is uploaded from instruments within the GLN 702. The system monitoring subsystems, operating, e.g., via the one or more mission control computers 221, 342, are configured to cause the display of sample collection results, e.g., as shown in FIGS. 10A and 10B. These examples provide various representations (e.g., map-based) within Mission Control summarizing test results (e.g., 700A, which depicts a color-coded map of the United States) as collected. Using this map-based example, Mission Control may allow users to zoom up and down through the map, providing them with the ability to examine testing results or other key data from various levels of granularity (e.g., county, city, state, country, etc.). For example, 670B depicts a multi-map map view, depicting outbreak locations globally (701B), within the United States (702B), and within a particular state—Illinois (703B).

A mission control facility may be staffed by a team of data analysts and/or other personnel that may have access to the data fed into system monitoring subsystem 220 from one or more GNL 700 instruments, and it may provide routine automated reports or the ability to drill down into specific data as warranted, through for example, the system monitoring subsystem (see, e.g., FIG. 1A, 102; FIG. 3, 342).

In embodiments, the system monitoring subsystem 220 may be configured to cause the display of at least the following non-limiting, illustrative examples of data to one or more analysts and/or other personnel of the mission control facility. In an embodiment, the system monitoring subsystem 220 may be configured to cause the display of real-time, geographical testing results from each lab in the GLN 702 and from each POC device 710 including positive test results, negative test results, and results from app symptom surveys. In embodiments, results may be for direct detection of pathogens or serology results. In embodiments, time-series tracking and trending of global testing results may be provided. In embodiments, real-time activity at sample collection sites, real-time activity related to users' usage of sample collection software on user devices 706, status of labs in the GLN 702 including, for example, inventory levels, equipment status, staffing levels. Further status information related to GLN 702 and/or POC devices 710 may include status information for instruments (e.g., cartridge readers), including: geographic location, and utilization rates. Further status information associated with the global bio-surveillance and response system 705 may include statuses for commercial manufacturing centers, including inventory levels, equipment status, staffing levels. In embodiments, the system monitoring subsystem 220 is further configured to collect and cause the display of real-time information on logistics flows to the labs in the GLN 702 and POC device 710 distribution points, real-time information on logistics flows into one or more commercial manufacturing centers. Using the pandemic example again, these data may be used, among other reasons, to positively impact a disease outbreak response.

Figure 11:
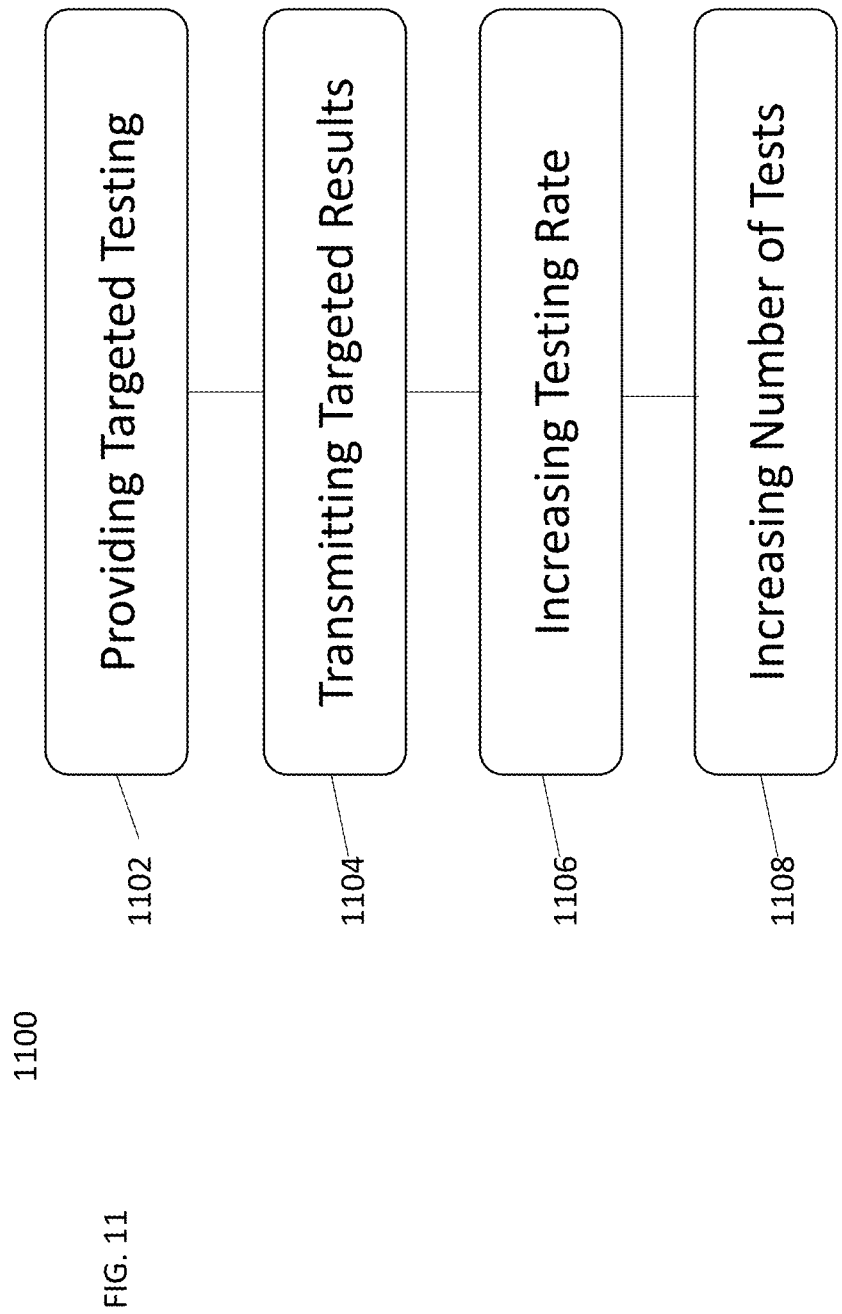
FIG. 11 illustrates a global bio-surveillance response method according to embodiments herein.

FIG. 11 illustrates a global bio-surveillance response method 1100 according to embodiments herein. The method 1100 may be carried out by a global bio-surveillance and response system, as described herein.

In an operation 1102, the method 1100 includes providing targeted testing to detect one or more health conditions among a population to obtain targeted results. Targeted testing may include conducting one or more tests selected or designed to obtain data or information about one or more specific health conditions. Targeted testing may be performed, for example, by the independent sample testing subsystem and/or by a sample collection facility in combination with a POC network or GNL.

In an operation 1104, the method 1100 includes transmitting the targeted results to a system monitoring subsystem, e.g., a mission control subsystem, in real-time across a distributed network of infrastructure, for example, the networking platform.

Responsive to the targeted results, the method 1100 includes performing one or more of operations 1106 and 1108. Operation 1106 includes increasing the rate of testing among the population to detect the presence of the one or more health conditions. Operation 1108 includes increasing the number of individuals tested among the population to detect the presence of the one or more health conditions. Operations 1106 and 1108 may include changing a phase of system operation, e.g., via a phase transition module.

Figure 12:
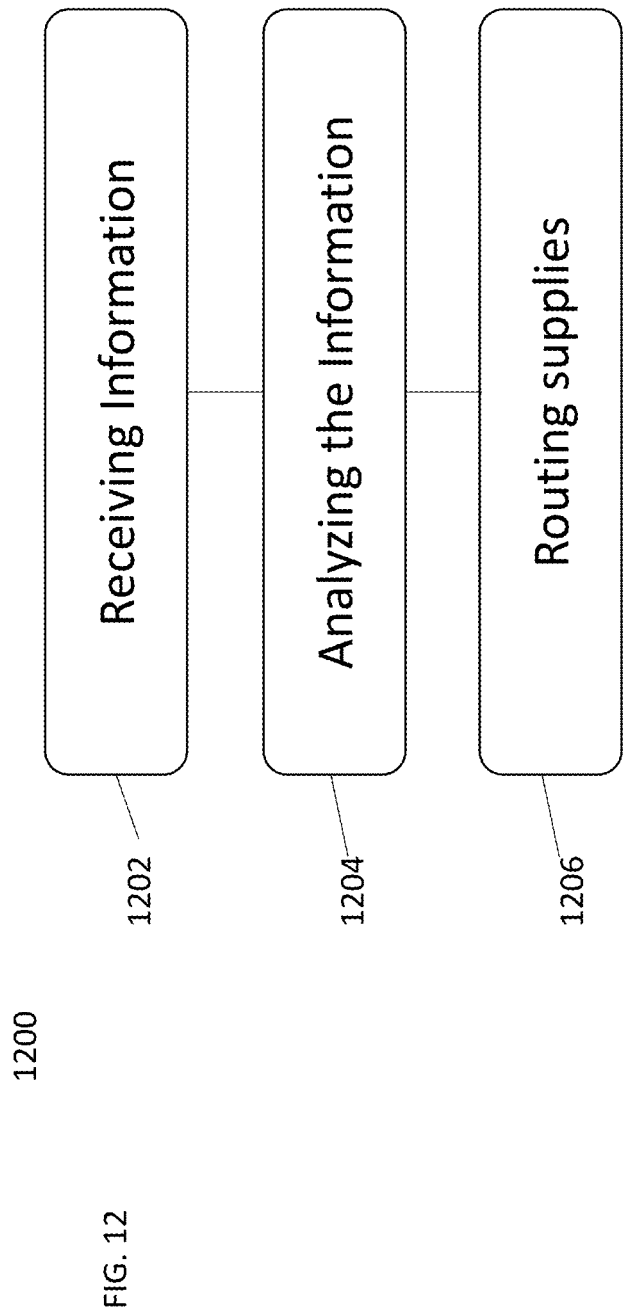
FIG. 12 illustrates a resource allocation method according to embodiments herein.

FIG. 12 illustrates a resource allocation method 1200 according to embodiments herein. The method 1200 may be carried out by a global bio-surveillance and response system, as described herein.

In an operation 1202, the method 1200 may include receiving information relating to one more available resources of a network of laboratories, such as a GLN, configured to monitor one or more health conditions in real-time. For example, available resources may include supplies, inventory, consumables, personnel, testing kits, equipment, etc. The information may be provided by, for example, a farm status module to a load balancing module and/or an inventory module.

In an operation 1204, the method 1200 may include analyzing the information based at least in part on one or more selection criteria. The analysis may be performed, for example, by an inventory module and/or a load balancing module.

In an operation 1206, the method 1200 may include routing one or more of equipment, test samples, instruments, supplies, and/or personnel to a selected laboratory among the network of laboratories responsive to analyzing the received information and based on the one or more selection criteria. The routing may be performed, for example, by a load balancing module.

Figure 13:
FIG. 13 illustrates a method for responding to a health-related triggering event according to embodiments herein.

FIG. 13 illustrates a method 1300 for responding to a health-related triggering event according to embodiments herein. The method 1300 may be carried out by a global bio-surveillance and response system, as described herein.

In an operation 1302, the method 1300 may include providing targeted testing to detect the presence of one or more health conditions among a population exhibiting a defined set of symptoms to obtain targeted testing results. Targeted testing may include conducting one or more tests selected or designed to obtain data or information about one or more specific health conditions. Targeted testing may be performed, for example, by the independent sample testing subsystem and/or by a sample collection facility in combination with a POC network or GNL.

In an operation 1304, the method 1300 may include transmitting the targeted results in real-time to a distributed infrastructure network, for example, the networking platform.

In an operation 1306, the method 1300 may include providing one or more scientific detection tools configured to analyze the one or more health conditions responsive to the targeted testing results. Scientific detection tools may include assays designed to target and/or detect pathogens related to the health condition. Scientific detection tools may further include any and all tools discussed herein to detect health conditions, including tools for radiation exposure detection, TBI assessment, etc.

In an operation 1308, the method 1300 may include developing a scientific diagnostic tool responsive to analysis of the targeted testing results from the one or more scientific detection tools. Scientific diagnostic tools may include, for example, direct detection immunoassays.

In an operation 1310, the method 1300 may include distributing one or more of test equipment, scientific detection tools, and scientific diagnostics tools to at least one location within the network of infrastructure responsive to providing the one or more scientific detection tools or developing the scientific diagnostic tool. During an emerging health condition, the global bio-surveillance and response system is configured to distribute scientific detection and diagnostic tools to the necessary locations to continue detection of the health condition. The inventory module, for example, in conjunction with the phase transition module, may be configured to coordinate and/or facilitate the distribution.

Figure 14:
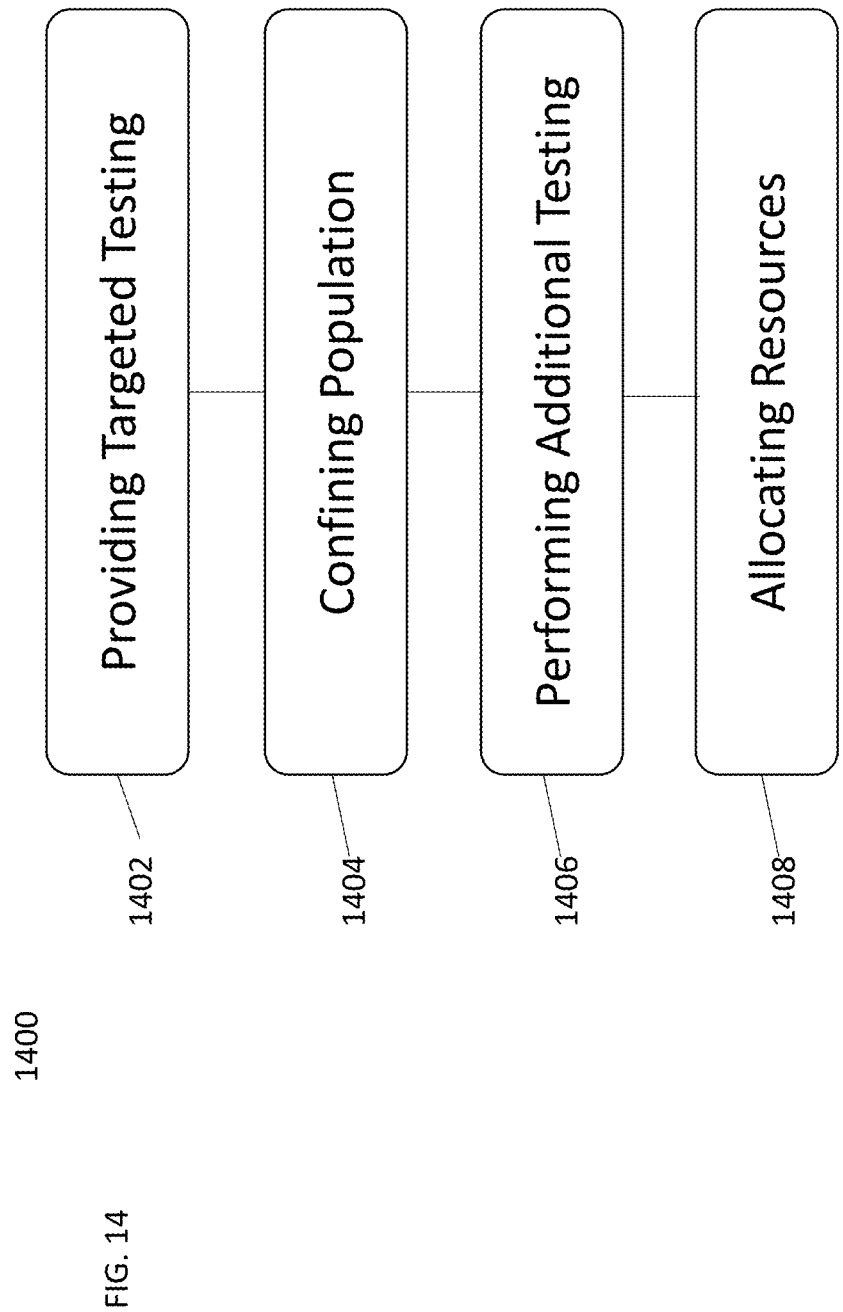
FIG. 14 illustrates a health condition containment method according to embodiments herein.

FIG. 14 illustrates a health condition containment method 1400 according to embodiments herein. The method 1400 may be carried out and/or facilitated by a global bio-surveillance and response system, as described herein.

In an operation 1402, the method 1400 may include providing targeted testing to detect one or more health conditions among a population within a geographical area, wherein the health conditions are at least one of biological, chemical, and biochemical. Targeted testing may include conducting one or more tests selected or designed to obtain data or information about one or more specific health conditions. Targeted testing may be performed, for example, by the independent sample testing subsystem and/or by a sample collection facility in combination with a POC network or GNL.

In an operation 1404, the method 1400 may include confining the population within that geographical area for a finite period of time responsive to the detection of the one or more health conditions within that geographical area. Quarantine procedures may be facilitated by the global bio-surveillance and response system, for example, via the system monitoring subsystem, to distribute appropriate information related to quarantine targeting according to specific locations.

In an operation 1406, the method 1400 may include performing additional testing of individuals within the geographical area within the finite period of time. The global bio-surveillance and response system is configured, e.g., via the orders module, to order additional testing within the quarantine or confinement area.

In an operation 1408, the method 1400 may include allocating additional resources to the geographical area for which the one or more health conditions were detected. For example, the inventory module and/or the load balancing module may operate to route supplies and/or resources to the quarantine/confinement area as required to support additional testing.

Figure 15:
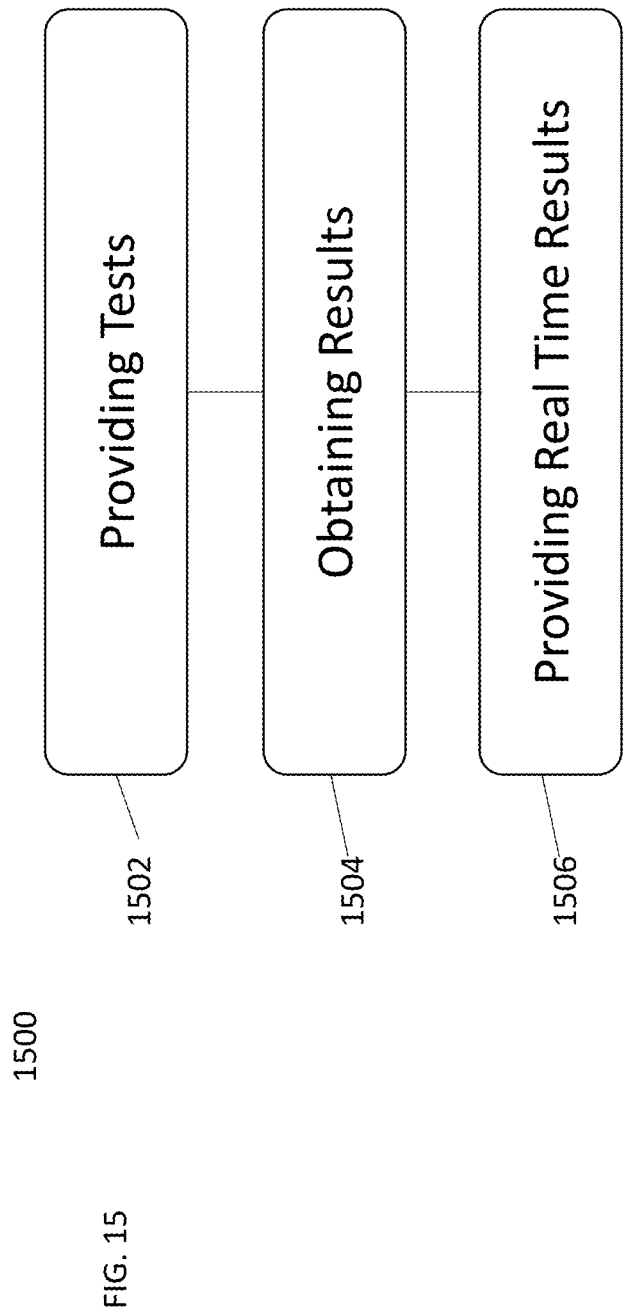
FIG. 15 illustrates a global bio-surveillance response method according to embodiments herein.

FIG. 15 illustrates a pandemic preparedness method 1500 according to embodiments herein. The method 1500 may be carried out and/or facilitated by a global bio-surveillance and response system, as described herein.

In an operation 1502, the method 1500 includes providing one or more tests to detect a set of one or more markers relating to the health condition, e.g., a known, unknown, and/or emerging pathogen. As described herein, the tests may be created by operators at a Tier-1 Lab and distributed as facilitated by, e.g., an inventory module, as described herein.

In an operation 1504, the method 1500 includes obtaining results from the one or more tests. Results may be obtained, for example, by one or more instruments associated with the GLN, the POC network, and/or an independent sample testing subsystem.

In an operation 1506, the method 1500 includes providing the results in real-time across a global network of infrastructure configured to identify and respond to a known, unknown, or emerging risk to health. The results may be provided responsive to the detection of the health condition and/or pathogen. The results may be communicated across the global bio-surveillance and response system by, for example, a results module as described herein.

In various embodiments described herein, one or more aspects of the disclosure may be embodied as a computer program product that may include a computer readable storage medium (or media) and/or a computer readable storage device. Such computer readable storage medium or device may store computer readable program instructions for causing a processor to carry out one or more methodologies described here. In one embodiment, the computer readable storage medium or device includes a tangible device that may retain and store instructions for use by an instruction execution device. Examples of the computer readable storage medium or device may include, but is not limited to, an electronic storage device, a magnetic storage device, an optical storage device, an electromagnetic storage device, a semiconductor storage device, or any suitable combination thereof, for example, such as a computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, but not limited to only those examples. The computer readable medium may comprise both computer readable storage media (as described above) or computer readable transmission media, which may include, for example, coaxial cables, copper wire, and fiber optics. Computer readable transmission media may also take the form of acoustic or light waves, such as those generated during radio frequency, infrared, wireless, or other media including electric, magnetic, or electromagnetic waves.

The terms "computer system," "computing device," and "computer" as may be used in the present application may include a variety of combinations of fixed and/or portable computer hardware, software, peripherals, mobile, and storage devices. These may include a plurality of individual components that are networked or otherwise linked to perform collaboratively or may include one or more stand-alone components. The hardware and software components of the computer system, computing device, and computer of the present application may include and may be included within fixed and portable devices such as desktop, laptop, and/or server. A module may be a component of a device, software, program, or system that implements some "functionality," which may be embodied as software, hardware, firmware, electronic circuitry, or etc.

Further embodiments include:

Embodiment 1 is a global bio-surveillance and response system, using: a first subsystem configured to perform monitoring of one or more health conditions; a second subsystem configured to perform one or more scientific functions in response to the first subsystem's detection of the one or more health conditions; and a networking platform, wherein the networking platform is configured to communicate information in real-time to and/or from one or both of the first and second subsystems.

Embodiment 2 is the system of embodiment 1, wherein the networking platform is a web-based platform.

Embodiment 3 is the system of embodiments 1 or 2, wherein the web-based platform is a cloud platform.

Embodiment 4 is the system of embodiments 1 to 3, wherein the first subsystem includes a plurality of cartridge reader testing devices distributed among a geographical area.

Embodiment 5 is the system of embodiments 1 to 4, wherein the first subsystem includes a plurality of Point of Care (POC) devices distributed among a geographical area.

Embodiment 6 is the system of embodiment 5, wherein the POC devices are configured for location and use at doctor offices, urgent care facilities, and/or other medical field locations.

Embodiment 7 is the system of embodiments 5 to 6, wherein the POC devices are configured to screen individuals for military applications, air travel, and/or sporting events.

Embodiment 8 is the system of embodiments 1 to 7, further including a system monitoring subsystem.

Embodiment 9 is the system of embodiments 1 to 8, wherein the first subsystem further includes an independent sample testing subsystem including one or more, computers, servers, tablets, and/or mobile devices and bio-instrumentation and configured to report test results.

Embodiment 10 is the system of embodiments 1 to 9, wherein the system further includes a sample collection and testing ordering subsystem including one or more computers, servers, tablets, and/or mobile devices configured to operate as part of the first subsystem or the second subsystem and configured to perform one or more of the following functions: placing orders on samples to be tested, sending samples to a testing location, and reviewing results of testing.

Embodiment 11 is the system of embodiments 1 to 10, wherein the second subsystem further includes a sample processing subsystem including one or more, computers, servers, tablets, and/or mobile devices and bio-instrumentation, and configured to perform testing of samples.

Embodiment 12 is the system of embodiments 1 to 11, wherein the second subsystem further includes scientific equipment including one or more of high throughput testing, ultrahigh throughput testing, sequencing, assay development, vaccine development, and/or scientific development instrumentation and equipment.

Embodiment 13 is the system of embodiment 12, wherein the scientific equipment is centralized in relation to one or more major metropolitan areas.

Embodiment 14 is the system of embodiments 12 to 13, wherein the sequencing includes next generation sequencing and/or nucleic acid sequencing.

Embodiment 15 is the system of embodiments 12 to 14, wherein the high throughput testing can include performing at least 100 million tests per week.

Embodiment 16 is the system of embodiments 1 to 15, wherein the second subsystem further includes one or more of partially automated and fully automated test equipment.

Embodiment 17 is the system of embodiment 16, wherein the test equipment is arranged into one or more farms, each including a plurality of instruments.

Embodiment 18 is the system of embodiments 16 to 17, wherein the instruments with each farm are adapted be configured in one or more of a research mode and a clinical mode, wherein the clinical mode locks out one or more operators from a plurality of features of the instruments that are otherwise available in research mode.

Embodiment 19 is the system of embodiments 1 to 18, wherein the real-time results are provided across a global laboratory network of infrastructure.

Embodiment 20 is the system of embodiments 1 to 19, wherein the system is configured to facilitate a response to a pandemic, epidemic, and/or endemic.

Embodiment 21 is the system of embodiments 1 to 20, wherein the system is configured to provide an epidemiological-based infrastructure for biodosimetry testing and/or radiological events.

Embodiment 22 is the system of embodiments 1 to 21, wherein the radiological events include a nuclear plant meltdown.

Embodiment 23 is the system of embodiments 1 to 22, wherein the system is configured to provide a biological- and/or chemical-defense-based infrastructure for responding to a chemical and/or biological-related attack.

Embodiment 24 is the system of embodiments 1 to 23, wherein the system is configured to utilize one or more ride-share services to facilitate the transportation of samples between collection and testing locations.

Embodiment 25 is the system of embodiment 24, wherein samples can be tracked through a barcode and/or QR code.

Embodiment 26 is the system of embodiment 25, wherein the tracked samples can be used to determine a manner in which to allocate testing resources within the network.

Embodiment 27 is the system of embodiments 1 to 25, wherein tracking of samples is configured to be monitored and/or controlled by the system monitoring subsystem.

Embodiment 28 is the system of embodiment 27, wherein the system monitoring subsystem is configured to communicate with one or more biometric devices for determining vitals of individuals including one or more of body temperature, blood pressure, and/or oxygen saturation values.

Embodiment 29 is the system of embodiments 1 to 28, wherein the first subsystem is configured to perform predictive testing on one or more of face masks, test equipment, and/or environmental surfaces to determine the presence of one or more pathogens.

Embodiment 30 is the system of embodiments 1 to 29, wherein the monitoring of one or more health conditions includes monitoring for one or more biological, chemical, and/or biochemical anomalies.

Embodiment 31 is the system of embodiment 30, wherein the monitoring includes performing luminescence testing.

Embodiment 32 is the system of embodiment 31, wherein the luminescence testing includes chemiluminescence testing.

Embodiment 33 is the system of embodiment 31 and 32, wherein the luminescence testing includes electrochemiluminescence testing.

Embodiment 34 is a method for responding to a known, unknown, or emerging health condition, including: providing targeted testing to detect one or more health conditions among a population to obtain targeted results; transmitting the targeted results to a system monitoring subsystem, wherein the targeted results are transmitted in real-time across a distributed network of infrastructure; responsive to the targeted results, performing one or more of the following steps: increasing the rate of testing among the population to detect the presence of the one or more health conditions, and increasing the number of individuals tested among the population to detect the presence of the one or more health conditions.

Embodiment 35 is the method of embodiment 34, further including performing an analysis of the targeted results.

Embodiment 36 is the method of embodiments 34 and 35, wherein one or more of increasing the rate of testing and increasing the number of individuals tested are performed with high-throughput testing.

Embodiment 37 is the method of embodiments 34 to 36, wherein one or more of increasing the rate of testing and increasing the number of individuals tested are performed with ultra-high-throughput testing.

Embodiment 38 is the method of embodiments 34 to 37, wherein the targeted testing further includes identifying individuals with negative test results that are exhibiting a particular set of symptoms.

Embodiment 39 is the method of embodiments 34 to 38, wherein the targeted testing is performed by a cartridge reader network distributed among a geographical area.

Embodiment 40 is the method of embodiment 39, wherein the targeted testing is performed by one or more Point of Care (POC) devices distributed among a geographical area.

Embodiment 41 is the method of embodiment 40, wherein the POC devices are configured to be located at doctor offices, urgent care facilities, and/or other medical field locations.

Embodiment 42 is the method of embodiments 40 and 41, wherein the POC devices can be used to screen individuals for military applications, air travel, and/or sporting events.

Embodiment 43 is the method of embodiments 34 to 42, further including monitoring one or more individuals through a user device configured for user monitoring.

Embodiment 44 is the method of embodiments 34 to 43, wherein the monitoring subsystem further includes identifying trends in positive test results.

Embodiment 45 is the method of embodiments 34 to 44, wherein the targeted testing further includes detecting antibodies, antigens, and/or nucleic acids.

Embodiment 46 is the method of embodiments 34 to 45, wherein the targeted results are transmitted via a cloud platform.

Embodiment 47 is the method of embodiments 34 to 46, wherein increasing the rate of testing and increasing the number of individuals tested are configured to facilitate a response to a pandemic, epidemic, and/or endemic.

Embodiment 48 is the method of embodiments 34 to 47, wherein the targeted testing to detect one or more health conditions further includes detecting one or more biological, chemical, and biochemical anomalies.

Embodiment 49 is the method of embodiment 48, wherein the detecting one or more anomalies includes performing luminescence testing.

Embodiment 50 is the method of embodiment 49, wherein the luminescence testing includes chemiluminescence testing.

Embodiment 51 is the method of embodiments 49 to 50, wherein the luminescence testing includes electrochemiluminescence testing.

Embodiment 52 is a method of allocating resources within a global bio-surveillance and response system, the method including: receiving information relating to one more available resources of a network of laboratories configured to monitor one or more health conditions in real-time; analyzing the received information based at least in part on one or more selection criteria; and routing one or more of equipment, test samples, instruments, supplies, and/or personnel to a selected laboratory among the network of laboratories responsive to analyzing the received information and based on the one or more selection criteria.

Embodiment 53 is the method of embodiment 52, wherein the one or more available resources include testing capacity, current inventory, current supplies, and/or a total number of instruments of a networked laboratory.

Embodiment 54 is the method of embodiments 52 and 53, wherein the routing step further includes re-routing one or more of equipment, test samples, instruments, supplies, and personnel that have been previously routed based on the one or more selection criteria.

Embodiment 55 is the method of embodiments 52 to 54, further including scheduling, via a scheduler module, one or more of testing, personnel allocation, and/or sample transportation within laboratories of the network of laboratories.

Embodiment 56 is the method of embodiment 55, wherein the scheduler includes a global scheduler configured to receive commands for establishing rules to allocate resources and/or schedule tasks on a global scale.

Embodiment 57 is the method of embodiments 55 and 56, wherein the scheduler includes a regional scheduler configured to receive commands for establishing rules to allocate resources and/or schedule tasks on a regional scale.

Embodiment 58 is the method of embodiment 57, wherein the regional scheduler further includes allocating resources and/or scheduling tasks within one or more farms of instruments.

Embodiment 59 is the method of embodiments 55 to 58, wherein the scheduler further includes receiving as an input one or more of a type of test results to be processed and/or frequency to be performed by one or more test sites when determining how to allocate resources and/or schedule tasks.

Embodiment 60 is the method of embodiments 55 to 59, wherein the scheduler further includes receiving as an input one or more of staffing schedules and/or performance metrics of one or more facilities and/or sites when determining how to allocate resources and/or schedule tasks.

Embodiment 61 is the method of embodiments 55 to 60, wherein the scheduler further includes receiving as an input one or more of staffing schedules and/or performance metrics of one or more facilities and/or sites when determining how to allocate resources and/or schedule tasks.

Embodiment 62 is the method of embodiments 52 to 61, wherein the scheduler further includes receiving customer orders for equipment, supplies, and/or other resources and managing an allocation of the same within the network of laboratories.

Embodiment 63 is the method of embodiment 62, wherein dispatching further includes procuring and/or distributing inventory and/or equipment between the network of laboratories.

Embodiment 64 is the method of embodiment 52 to 63, further including load balancing the network of laboratories, via a load balancing module, wherein the load balancing module employs a combination of real-time algorithms and human analysis to optimize resource allocation and/or task scheduling within the network of laboratories.

Embodiment 65 is the method of embodiment 64, wherein the real-time algorithms evaluate one or more of staff levels, supply inventory levels, and/or testing throughput of one or more laboratories and/or other facilities to optimize resource allocation and/or task scheduling within the network of laboratories.

Embodiment 66 is the method of embodiments 64 to 65, wherein the load balancer further includes minimizing workloads of operators at one or more testing facilities.

Embodiment 67 is the method of embodiments 64 to 66, wherein the load balancer further includes predicting timing for inventory replenishment of one or more laboratories and/or other facilities within the network of laboratories.

Embodiment 68 is the method of embodiments 64 to 67, wherein the load balancer further includes optimizing resource allocation and/or task scheduling based on considerations of proximity of resources to laboratories and/or other facilities.

Embodiment 69 is the method of embodiments 64 to 68, wherein the real-time algorithm further includes adjusting dynamically based on a change of circumstances, including a site being taken off line and/or a region being made temporarily unavailable.

Embodiment 70 is the method of embodiments 52 to 69, wherein the monitoring of one or more health conditions includes monitoring for one or more biological, chemical, and biochemical anomalies.

Embodiment 71 is the method of embodiment 70, wherein the monitoring further includes performing luminescence testing.

Embodiment 72 is the method of embodiment 71, wherein the luminescence testing includes chemiluminescence testing.

Embodiment 73 is the method of embodiments 71 and 72, wherein the luminescence testing includes electrochemiluminescence testing.

Embodiment 74 is a method for responding to a health-related triggering event, the method including: providing targeted testing to detect the presence of one or more health conditions among a population exhibiting a defined set of symptoms to obtain targeted testing results; transmitting the targeted testing results in real-time to a distributed infrastructure network; providing one or more scientific detection tools configured to analyze the one or more health conditions responsive to the targeted testing results; and developing a scientific diagnostic tool responsive to analysis of the targeted testing results from the one or more scientific detection tools; and distributing one or more of test equipment, scientific detection tools, and scientific diagnostics tools to at least one location within the network of infrastructure responsive to providing the one or more scientific detection tools or developing the scientific diagnostic tool.

Embodiment 75 is the method of embodiment 74, wherein the one or more scientific detection tools include one or more assays.

Embodiment 76 is the method of embodiment 74, wherein the one or more health conditions includes at least at detected pathogen.

Embodiment 77 is the method of embodiment 76, wherein the scientific diagnostic tool is configured for creation of direct detection immunoassays of the detected pathogen.

Embodiment 78 is the method of embodiments 76 and 77, wherein the scientific diagnostic tool is configured for sequencing of the detected pathogen.

Embodiment 79 is the method of embodiments 74 to 78, further including assessing the one or more health conditions.

Embodiment 80 is the method of embodiments 74 to 79, further including providing the targeted testing results in real-time across a global network of infrastructure.

Embodiment 81 is the method of embodiments 74 to 80, wherein the one or more scientific detection tools includes cartridge-based assays.

Embodiment 82 is the method of embodiments 74 to 81, wherein the one or more scientific detection tools include cartridge-based serological testing.

Embodiment 83 is the method of embodiments 74 to 82, wherein the one or more scientific detection tools include cartridge-based assays including antigens tagged with complementary nucleic acid sequences.

Embodiment 84 is the method of embodiments 74 to 83, further including manufacturing cartridge-based assays for testing for the presence of one or more specific pathogens.

Embodiment 85 is the method of embodiments 74 to 84, further including manufacturing cartridge-based assays for performing serological testing.

Embodiment 86 is the method of embodiment 85, wherein the cartridge-based assays include an array of antigens directly immobilized on a capture array.

Embodiment 87 is the method of embodiments 74 to 86, further including manufacturing proteins and/or antigens related to assays.

Embodiment 88 is the method of embodiments 74 to 87, further including developing direct detection immunoassays.

Embodiment 89 is the method of embodiments 74 to 88, wherein the targeted testing includes testing against a standard upper respiratory panel.

Embodiment 90 is the method of embodiments 74 to 89, further including sequencing negative results obtained during the targeted testing with sequencing instrumentation.

Embodiment 91 is the method of embodiments 74 to 90, wherein the one or more of the scientific tools can be applied at an increased frequencies as compared to the targeted testing.

Embodiment 92 is the method of embodiments 74 to 91, wherein the targeted testing further includes pooling of samples, wherein the pooling pool includes at least ten samples.

Embodiment 93 is the method of embodiment 92, further including re-testing individual samples within a pooled sample in response to the pooled sample testing positive.

Embodiment 94 is the method of embodiments 74 to 93, wherein the targeted testing further includes detecting one or more biological, chemical, and biochemical anomalies.

Embodiment 95 is the method of embodiment 94, wherein the monitoring further includes performing luminescence testing.

Embodiment 96 is the method of embodiment 95, wherein the luminescence testing includes chemiluminescence testing.

Embodiment 97 is the method of embodiments 94 and 95, wherein the luminescence testing includes electrochemiluminescence testing.

Embodiment 98 is a device for managing a global bio-surveillance and response system, including at least one processor configured to execute software instructions to provide: an information subsystem configured to receive information from at least one subsystem and to facilitate the analysis of the information for providing a response to a potential health risk to a population; and a command subsystem configured to provide commands to the at least one subsystem for carrying out the response, wherein the information subsystem and the command subsystem are configured to receive real-time communications from the at least one subsystem through a web-based platform.

Embodiment 99 is the device of embodiments 98, wherein the response includes providing one or more of equipment, instruments, supplies, and/or personnel to the at least one subsystem.

Embodiment 100 is the device of embodiments 98 and 99, wherein the at least one processor is further configured to execute software instructions to output information to a display in a graphical and/or tabular format.

Embodiment 101 is the device of embodiments 98 to 100, wherein the at least one processor is further configured to execute software instructions to provide one or more map-based views of real-time results received by one or more of the first subsystem and a second subsystem.

Embodiment 102 is the device of embodiment 101, wherein the one or more map-based views includes views by country, state, province, and/or county.

Embodiment 103 is the device of embodiments 101 and 102, wherein the one or more map-based views provides an aggregated view of testing facilities within the global bio-surveillance and response system.

Embodiment 104 is the device of embodiments 101 to 103, wherein the one or more map-based views provides an aggregated view of testing equipment within the global bio-surveillance and response system.

Embodiment 105 is the device of embodiments 98 to 104, wherein the device is configured to be employed by one or more of local, state, federal government, or other governmental agencies.

Embodiment 106 is the device of embodiments 98 to 105, wherein the information subsystem is configured to provide information access to one or more of hospitals, universities, schools, public and/or private research organizations, governmental agencies, and/or other commercial entities.

Embodiment 107 is the device of embodiments 98 to 106, wherein the real-time communications include real-time test results received from a first subsystem of the at least one subsystem.

Embodiment 108 is the device of embodiments 98 to 107, wherein the real-time communications include time-series tracking and trending of global test results.

Embodiment 109 is the device of embodiments 98 to 108, wherein the real-time communications include information for performing real-time tracking of collection site activities.

Embodiment 110 is the device of embodiments 98 to 109, wherein the real-time communications include status information related to one or more laboratories located within one or more of a first subsystem of the at least one subsystem and a second subsystem.

Embodiment 111 is the device of embodiment 98 to 110, wherein the real-time communications include instrument information relating to the status of one or more instruments located within one or more of a first subsystem of the at least one subsystem and a second subsystem.

Embodiment 112 is the device of embodiments 98 to 111, wherein the real-time communications include manufacturing information relating to the status of one or more manufacturing locations located within one or more of a first subsystem of the at least one subsystem and a second subsystem.

Embodiment 113 is the device of embodiments 98 to 112, wherein the real-time communications include logistic information relating to one or more logistical flow processes occurring within one or more of a first subsystem of the at least one subsystem and a second subsystem.

Embodiment 114 is the device of embodiments 98 to 113, wherein the information includes one or more of real-time geographical test results, time-series tracking, real-time activity at sample collection sites, real-time activities related to use of an app, status of laboratories in the global bio-surveillance and response system, status information of cartridge readers, status information for manufacturing facilities, real-time info on logistics flow in the global bio-surveillance and response system, cartridge distribution points, and/or location of manufacturing centers.

Embodiment 115 is the device of embodiments 98 to 114, wherein the information subsystem and the command subsystems communicate via a networking platform.

Embodiment 116 is the device of embodiments 98 to 115, wherein the at least one processor is further configured to execute software instructions to analyze and/or reporting the information.

Embodiment 117 is the device of embodiments 98 to 116, wherein the at least one processor is further configured to execute software instructions to facilitate data sharing among testing facilities.

Embodiment 118 is the device of embodiments 98 to 117, wherein the command subsystem is configured to facilitate placement of supply and/or equipment orders.

Embodiment 119 is the device of embodiments 98 to 118, wherein the command subsystem is configured to provide commands for relocating resources among the global bio-surveillance and response system.

Embodiment 120 is the device of embodiments 98 to 119, wherein the information received by the information subsystem includes luminescence testing information.

Embodiment 121 is the device of embodiments 120, wherein the luminescence testing includes chemiluminescence testing.

Embodiment 122 is the device of embodiments 120 and 121, wherein the luminescence testing includes electrochemiluminescence testing.

Embodiment 123 is a global bio-surveillance and response system, including: a subsystem configured to perform monitoring of one or more health conditions, wherein the subsystem includes a plurality of portable testing devices distributed among a geographical area; a system monitoring subsystem configured to: receive inputs from the subsystem and send outputs to the subsystem in real-time, facilitate analysis of the inputs, and determine the outputs, responsive to the inputs; and a networking platform configured to communicate with a plurality of the portable testing devices in real time.

Embodiment 124 is the system of embodiment 123, wherein the system monitoring subsystem is further configured to determine the outputs within a predetermined time period after receiving the inputs.

Embodiment 125 is the system of embodiment 124, wherein the predetermined time period is less than five minutes.

Embodiment 126 is the system of embodiment 123 to 125, wherein the subsystem is configured to perform tests to screen for one or more known, unknown, and/or emerging pathogens.

Embodiment 127 is the system of embodiment 123 to 126, wherein the networking platform is a cloud platform.

Embodiment 128 is the system of embodiment 123 to 127, wherein the subsystem includes a plurality of cartridge reader testing devices distributed among a geographical area.

Embodiment 129 is the system of embodiment of 128, wherein the plurality of cartridge reader testing devices includes one or more Point of Care (POC) devices distributed among a geographical area.

Embodiment 130 is the system of embodiment 129, wherein the POC devices are configured to be located at doctor offices, urgent care facilities, and/or other medical field locations.

Embodiment 131 is the system of embodiment 128 and 129, wherein the POC devices can be used to screen individuals for military applications, air travel, and/or sporting events.

Embodiment 132 is the system of embodiment 123 to 131, wherein the system monitoring subsystem is configured to provide one or more map-based views of real-time results received from the subsystem.

Embodiment 133 is the system of embodiment 132, wherein the one or more map-based views includes views by country, state, province, and/or county.

Embodiment 134 is the system of embodiment 132 and 133, wherein the one or more map-based views provide an aggregated view of testing facilities within the global bio-surveillance and response system.

Embodiment 135 is the system of embodiment 132 to 134, wherein the one or more map-based views provide an aggregated view of testing equipment within the global bio-surveillance and response system.

Embodiment 136 is the system of embodiment 123 to 135, wherein the system monitoring subsystem is configured to provide access to the one or more of the inputs and the outputs by one or more of hospitals, universities, public and/or private research organizations, governmental agencies, and/or other commercial entities.

Embodiment 137 is the system of embodiment 123 to 136, further including an independent sample testing subsystem including one or more, computers, servers, tablets, and/or mobile devices and bio-instrumentation, and is configured to report test results.

Embodiment 138, is the system of embodiment 123 to 137, wherein subsystem configured to perform monitoring of one or more health conditions is further configured to perform monitoring of one or more Embodiment 139 is the system of embodiment 138, wherein the monitoring includes performing luminescence testing.

Embodiment 140 is the system of embodiment 139, wherein the luminescence testing information includes chemiluminescence testing.

Embodiment 141 is the system of embodiment 138 and 139, wherein the luminescence testing includes electrochemiluminescence testing.

Embodiment 142 is a global bio-surveillance and response system, including: a first subsystem configured to perform one or more scientific functions in response to a detection by a second subsystem of one or more health conditions, wherein the subsystem includes a plurality of scientific diagnostic equipment; a system monitoring subsystem configured to: receive inputs from the first subsystem and the second subsystem and sending outputs to the first subsystem and the second subsystem in real-time, and facilitate analysis of the inputs to determine the outputs to send to the first subsystem; and a networking platform, wherein the networking platform is configured to communicate with the scientific diagnostic equipment in real time.

Embodiment 143 is the system of embodiment 142, wherein the first subsystem and the second subsystem are the same subsystem.

Embodiment 144 is the system of embodiments 142 and 143, wherein the first subsystem and the second subsystem are different subsystems.

Embodiment 145 is the system of embodiments 142 to 144, wherein the outputs include allocation of resources to the subsystem.

Embodiment 146 is the system of embodiment 145, wherein the resources include one or more of equipment, instruments, supplies, and/or personnel.

Embodiment 147 is the system of embodiments 142 to 146, wherein the first subsystem is configured to increase the frequency and/or amount of testing and/or assay development in response to the detection of the one or more health conditions.

Embodiment 148 is the system of embodiments 142 to 147, wherein the networking platform is a cloud platform.

Embodiment 149 is the system of embodiments 142 to 148, further including a sample processing subsystem, including one or more, computers, servers, tablets, and/or mobile devices and bio-instrumentation, and is configured to perform testing.

Embodiment 150 is the system of embodiment 142 to 149, wherein the second subsystem further includes scientific equipment including one or more of high throughput testing, ultrahigh throughput testing, sequencing, assay development, vaccine development, and/or scientific development instrumentation and equipment.

Embodiment 151 is the system of embodiment 150, wherein the scientific equipment is centralized in relation to one or more major metropolitan areas.

Embodiment 152 is the system of embodiments 150 and 151, wherein the sequencing includes next-generation sequencing and/or nucleic acid sequencing.

Embodiment 153 is the system of embodiments 150 to 152, wherein the high throughput testing includes performing at least 100 million tests per week.

Embodiment 154 is the system of embodiments 142 to 153, wherein the second subsystem further includes one or more of partially automated and fully automated test equipment.

Embodiment 155 is the system of embodiment 154, wherein the test equipment is arranged into one or more farms, each including a plurality of instruments.

Embodiment 156 is the system of embodiment 155, wherein the instruments with each farm are adapted be configured in one or more of a research mode and a clinical mode, wherein the clinical mode locks out one or more operators from a plurality of features of the instruments that are otherwise available in research mode.

Embodiment 157 is the system of embodiments 142 to 156, wherein the detection of one or more health conditions includes detecting one or more biological, chemical, and/or biochemical anomalies.

Embodiment 158 is the system of embodiments 157, wherein detecting one or more anomalies includes performing luminescence testing.

Embodiment 159 is the system of embodiment 158, wherein the luminescence testing information includes chemiluminescence testing.

Embodiment 160 is the system of embodiments 158 and 159, wherein the luminescence testing includes electrochemiluminescence testing.

Embodiment 161 is a method of minimizing the spread of a health condition in a population, the method including: providing targeted testing to detect one or more health conditions among a population within a geographical area, wherein the health conditions are at least one of biological, chemical, and biochemical; confining the population within that geographical area for a finite period of time responsive to the detection of the one or more health conditions within that geographical area; performing additional testing of individuals within the geographical area within the finite period of time; and allocating additional resources to the geographical area for which the one or more health conditions were detected.

Embodiment 162 is the method of embodiment 161, wherein the additional resources include one or more of equipment, instruments, supplies, and/or personnel.

Embodiment 163 is the method of embodiments 161 and 162, further including performing contact tracing to minimize the spread of the one or more health conditions.

Embodiment 164 is the method of embodiments 161 to 163, further including performing predictive and/or artificial intelligence/machine-based learning to predict locations and/or groups of individuals more likely to test positive for the one or more health conditions.

Embodiment 165 is the method of embodiments 161 to 164, further including performing recursive testing and/or real-time data analysis of infected and/or potentially affected individuals.

Embodiment 166 is the method of embodiments 161 to 165, wherein performing additional testing further includes one or more of: increasing a rate of testing among the population to detect the presence of the one or more anomalies, and increasing a number of individuals tested among the population to detect the presence of the one or more anomalies.

Embodiment 167 is the method of embodiments 161 to 166, wherein the targeted testing is performed by a plurality of cartridge reader testing devices distributed among a geographical area.

Embodiment 168 is the method of embodiments 161 to 167, wherein the targeted testing is performed by a plurality of Point of Care (POC) devices distributed among the geographical area.

Embodiment 169 is the method of embodiments 161 to 168, further including performing predictive testing on one or more of face masks, test equipment, and/or environmental surfaces to determine the presence of one or more pathogens.

Embodiment 170 is the method of embodiments 161 to 169, wherein results from the targeted testing and the additional testing are reported in real-time over a web-based platform.

Embodiment 171 is the method of embodiment 170, wherein the web-based platform is a cloud-based platform.

Embodiment 172 is the method of embodiments 161 to 171, wherein the providing targeted testing of one or more health conditions includes performing luminescence testing.

Embodiment 173 is the method of embodiment 172, wherein the luminescence testing information includes chemiluminescence testing.

Embodiment 174 is the method of embodiments 172 and 173, herein the luminescence testing includes electrochemiluminescence testing.

Embodiment 175 is a global laboratory network, including: a plurality of networked laboratories having a geographical distribution and configured to provide continuous monitoring of populations, targeted testing, and/or scientific functions, wherein each one of the plurality of networked laboratory is configured to communicate with one or more other ones of the plurality of networked laboratories; and a system monitoring subsystem configured to: receive inputs from the plurality of networked laboratories, and send outputs to one or more of the plurality of networked laboratories in real-time, allocate resources among the plurality of networked laboratories based at least in part on the inputs from the or more laboratories.

Embodiment 176 is the network of embodiment 175, wherein the resources include one or more of equipment instruments, supplies, and/or personnel.

Embodiment 177 is the network of embodiments 175 and 176, wherein the plurality of networked laboratories is configured to continuously monitor one or more populations for the presence of unknown pathogens.

Embodiment 178 is the network of embodiments 175 to 177, wherein the plurality of networked laboratories is configured to identify and/or sequence emerging pathogens.

Embodiment 179 is the network of embodiments 175 to 178, wherein the plurality of networked laboratories is configured to communicate with one or more user devices to pair one or more samples with one or more individuals from whom the samples were collected.

Embodiment 180 is the network of embodiments 175 to 179, wherein the samples include one or more serum, plasma, urine, saliva, csf, fecal, cell supernatants, and/or nasal swab samples.

Embodiment 181 is the network of embodiments 175 to 180, wherein at least one of the plurality of networked laboratories include preexisting commercial laboratories and/or public health facilities.

Embodiment 182 is the network of embodiments 175 to 181, wherein the plurality of networked laboratories includes at least 1,000 geographically distributed laboratories.

Embodiment 183 is the network of embodiments 175 to 182, wherein the plurality of networked laboratories includes tier-1 facilities and tier-2 facilities, further wherein the tier-2 facilities are configured to provide routine and increased-frequency testing.

Embodiment 184 is the network of embodiment 183, wherein the tier-1 facilities are further configured to provide all services performed by the tier-2 laboratories and assay development services.

Embodiment 185 is the network of embodiment 183 to 184, wherein the tier-1 and/or tier-2 facilities are configured to manufacture assay reagents.

Embodiment 186 is the network of embodiments 175 to 185, wherein the plurality of networked laboratories further includes one or more satellite sites, wherein the one or more satellite sites include one or more of patient testing offices, pharmacies, and urgent care facilities.

Embodiment 187 is the network of embodiments 175 to 186, wherein the locations of the plurality of networked laboratories are selected according to proximity to one or more of population centers, transportation facilities, airports, public utility systems, and/or internet infrastructure sites.

Embodiment 188 is the network of embodiments 175 to 187, wherein the locations of the plurality of networked laboratories are selected according to proximity to one or more regions of potential outbreak.

Embodiment 189 is the network of embodiments 175 to 188, wherein the locations of the plurality of networked laboratories are selected according to proximity to one or more regions of potential outbreak.

Embodiment 190 is the network of embodiments 175 to 189, wherein the plurality of networked laboratories can be configured to be used as biobanks.

Embodiment 191 is the network of embodiments 175 to 190, wherein the network can further include one or more inventory centers configured to provide supplies and/or equipment to the plurality of networked laboratories located within the network.

Embodiment 192 is the network of embodiments 175 to 191, wherein the targeted testing includes performing luminescence testing.

Embodiment 193 is the network of embodiment 192, wherein the luminescence testing information includes chemiluminescence testing.

Embodiment 194 is the network of embodiments 192 and 193, wherein the luminescence testing includes electrochemiluminescence testing.

Embodiment 195 is a method of pandemic preparedness, including: providing one or more tests to detect a known, unknown, or emerging pathogen; and providing, responsive to detection of an unknown or emerging pathogen, real-time results across a global network of infrastructure, the global network of infrastructure being configured to provide testing for the unknown or emerging pathogen and respond to the unknown or emerging pathogen.

Embodiment 196 is the method of embodiment 195, further including providing the one or more tests are by cartridge-based assays.

Embodiment 197 is the method of embodiments 195 and 196, further including providing one or more scientific detections tools for responding to the unknown or emerging pathogen.

Embodiment 198 is the method of embodiment of 197, wherein the one or more scientific detection tools include cartridge-based serological testing.

Embodiment 199 is the method of embodiments of 197 and 198, wherein the one or more scientific detection tools include cartridge-based assay that include antigens tagged with complementary nucleic acid sequences.

Embodiment 200 is the method of embodiments of 197 to 199, wherein the one or more scientific detection tools are configured for application at an increased frequency as compared to the frequency of providing the one or more tests.

Embodiment 201 is the method of embodiments 195 to 200, further including communicating the real-time results over a networking platform.

Embodiment 202 is the method of embodiments 201, wherein the networking platform is a cloud-based platform.

Embodiment 203 is the method of embodiments 195 to 202, further including providing the one or more tests via a plurality of cartridge reader testing devices distributed across a geographical area.

Embodiment 204 is the method of embodiments 195 to 203, further including providing the one or more tests via a Point of Care (POC) device network distributed among a geographical area.

Embodiment 205 is the method of embodiments 195 to 204, wherein the POC devices are configured to be located at doctor offices, urgent care facilities, and/or other medical field locations.

Embodiment 206 is the method of embodiments 204, wherein the POC devices can be used to screen individuals for military applications, air travel, and/or sporting events.

Embodiment 207 is the method of embodiments 195 to 206, further including providing a system monitoring subsystem for facilitating communication of test results and/or response to the unknown or emerging pathogen.

Embodiment 208 is the method of embodiments 195 to 207, further including providing one or more tests including performing luminescence testing.

Embodiment 209 is the method of embodiment 208, wherein the luminescence testing information includes chemiluminescence testing.

Embodiment 210 is the method of embodiment 208 and 209, wherein the luminescence testing includes electrochemiluminescence testing.

Embodiment 211 is a method of tracking a health condition in a population, including: providing one or more tests to detect a set of one or more markers relating to the health condition; obtaining results from the one or more tests; and providing the results in real-time across a global network of infrastructure configured to identify and respond to a known, unknown, or emerging risk to health.

Embodiment 212 is the method of embodiment 211, wherein the infrastructure includes a plurality of networked laboratories.

Embodiment 213 is the method of embodiments 211 and 212, wherein the results are provided over a networking platform.

Embodiment 214 is the method of embodiment 213, wherein the networking platform is a cloud platform.

Embodiment 215 is the method of embodiments 211 to 214, wherein providing the one or more tests includes distributing a plurality of cartridge reader testing devices across a geographical area.

Embodiment 216 is the method of embodiment 211 to 215, wherein providing the one or more tests includes distributing a plurality of Point of Care (POC) devices across a geographical area.

Embodiment 217 is the method of embodiment 216, wherein the POC devices are configured to be located at doctor offices, urgent care facilities, and/or other medical field locations.

Embodiment 218 is the method of embodiments 216 and 217, wherein the POC devices can be used to screen individuals for military applications, air travel, and/or sporting events.

Embodiment 219 is the method of embodiments 211 to 218, wherein providing the tests includes performing the tests on one or more of partially automated and fully automated test equipment.

Embodiment 220 is the method of embodiment 219, wherein the test equipment is arranged into one or more networked farms, each farm including a plurality of instruments.

Embodiment 221 is the method of embodiments 211 to 220, further including facilitating a response to a pandemic, epidemic, and/or endemic.

Embodiment 222 is the method of embodiments 211 to 221, further including providing an epidemiological-based infrastructure for biodosimetry testing and/or radiological events.

Embodiment 223 is the method of embodiment 222, wherein the radiological events include a nuclear plant meltdown.

Embodiment 224 is the method of embodiments 211 to 223, further including providing a biological- and/or chemical-defense-based infrastructure for responding to a chemical and/or biological-related attack.

Embodiment 225 is the method of embodiments 211 to 224, wherein performing the one or more tests includes performing predictive testing on one or more of face masks, test equipment, and/or environmental surfaces to determine the presence of one or more pathogens.

Embodiment 226 is the method of embodiments 211 to 225, wherein providing the one or more tests includes performing luminescence testing.

Embodiment 227 is the method of embodiment 226, wherein the luminescence testing information includes chemiluminescence testing.

Embodiment 228 is the method of embodiments 226 and 227, wherein the luminescence testing includes electrochemiluminescence testing.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The embodiments described above are illustrative examples and it should not be construed that the present invention is limited to these particular embodiments. It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the methods or processes). In addition, while certain features of embodiments hereof are described as being performed by a single module or unit for purposes of clarity, it should be understood that the features and functions described herein may be performed by any combination of units or modules. Thus, various changes and modifications may be affected by one skilled in the art without departing from the spirit or scope of the invention as defined in the appended claim.

What is claimed is:

1. A method of allocating resources within a global bio-surveillance and response system to be carried out by at least one server having at least one processor, the method comprising:
   receiving information from a farm status module relating to one or more available resources of a network of laboratories configured to monitor one or more health conditions in real-time;
   analyzing the information via an inventory module and/or a load balancing module of the at least one server based at least in part on one or more selection criteria, the load balancing module further including a local collection of services and software configured to balance sample processing loads and inventory loads across the network of laboratories;
   balancing, via the load balancing module and according to the analyzing, sample processing loads and inventory loads across the network of laboratories; and
   causing, via the load balancing module, a routing of one or more of equipment, test samples, instruments, supplies, and/or personnel to a selected laboratory among the network of laboratories responsive to analyzing the received information and based on the one or more selection criteria, the routing including:
      engaging a delivery service and scheduling pick-up and delivery of the one or more of equipment, test sample, instruments, supplies, and/or personnel;
      printing shipping labels; and
      paying shipping charges.

2. The method of claim 1, wherein the one or more available resources include testing capacity, current inventory, current supplies, and/or a total number of instruments of a networked laboratory.

3. The method of claim 1, wherein the routing caused by the load balancing module further includes re-routing one or more of the equipment, test samples, instruments, supplies, and/or personnel that have been previously routed based on the one or more selection criteria.

4. The method of claim 1, further comprising scheduling one or more of testing, personnel allocation, and/or sample transportation within laboratories of the network of laboratories.

5. The method of claim 4, wherein scheduling further comprises receiving commands for establishing rules to allocate resources and/or schedule tasks on a global scale via a global scheduler.

6. The method of claim 4, wherein scheduling further comprises receiving commands for establishing rules to allocate resources and/or schedule tasks on a regional scale via a regional scheduler.

7. The method of claim 6, wherein the regional scheduler further includes allocating resources and/or scheduling tasks within one or more farms of instruments.

8. The method of claim 4, further comprising receiving as an input one or more of a type of test results to be processed and/or frequency to be performed by one or more test sites when determining how to allocate resources and/or schedule tasks.

9. The method of claim 4, further comprising receiving as an input one or more of staffing schedules and/or performance metrics of one or more facilities and/or sites when determining how to allocate resources and/or schedule tasks.

10. The method of claim 4, further comprising receiving and managing an allocation of customer orders for equipment, supplies, and/or other resources within the network of laboratories.

11. The method of claim 1, further comprising dispatching one or more of supplies, test samples, equipment, and/or samples within the network of laboratories.

12. The method of claim 11, wherein dispatching further includes procuring and/or distributing inventory and/or equipment between the network of laboratories.

13. The method of claim 1, wherein the load balancing module employs a combination of real-time algorithms and human analysis to optimize resource allocation and/or task scheduling within the network of laboratories.

14. The method of claim 13, wherein the real-time algorithms evaluate one or more of staff levels, supply inventory levels, and/or testing throughput of one or more laboratories and/or other facilities to optimize resource allocation and/or task scheduling within the network of laboratories.

15. The method of claim 13, wherein the load balancing module further includes minimizing workloads of operators at one or more testing facilities.

16. The method of claim 13, wherein the load balancing module further includes predicting timing for inventory replenishment of one or more laboratories and/or other facilities within the network of laboratories.

17. The method of claim 13, wherein the load balancing module further includes optimizing resource allocation and/or task scheduling based on considerations of proximity of resources to laboratories and/or other facilities.

18. The method of claim 13, wherein the real-time algorithms further includes adjusting dynamically based on a change of circumstances, including a site being taken off line and/or a region being made temporarily unavailable.

19. The method of claim 1, wherein monitoring the one or more health conditions includes monitoring for one or more biological, chemical, and biochemical anomalies.

20. The method of claim 19, wherein the monitoring further includes performing luminescence testing.

21. The method of claim 20, wherein the luminescence testing includes chemiluminescence testing.

22. The method of claim 20, wherein the luminescence testing includes electrochemiluminescence testing.

23. The method of claim 1 wherein the information received from the farm status module includes a plurality of load balancing scorecards, each associated with a networked laboratory and including information defining an operational status of the associated network laboratory.

24. The method of claim 1, wherein analyzing the information further includes projecting future sample processing times and future inventory needs according to enroute resources.

25. The method of claim 1 wherein routing caused via the load balancing module of the at least one server is performed to address inventory management issues identified across regional deployments of the network of laboratories, and to facilitate inventory management across multiple regions.

26. The method of claim 1 wherein the at least one server is a global services server.

* * * * *